US011780893B2

(12) United States Patent
Munch et al.

(10) Patent No.: US 11,780,893 B2
(45) Date of Patent: *Oct. 10, 2023

(54) KV1.3 BLOCKERS

(71) Applicant: Zealand Pharma A/S, Søborg (DK)

(72) Inventors: Henrik Fischer Munch, Søborg (DK); Rasmus Bugge Jensen, Søborg (DK); Jens Kvist Madsen, Søborg (DK)

(73) Assignee: Zealand Pharma A/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/679,925

(22) Filed: Feb. 24, 2022

(65) Prior Publication Data
US 2022/0251151 A1 Aug. 11, 2022

Related U.S. Application Data

(63) Continuation of application No. 17/356,354, filed on Jun. 23, 2021, now Pat. No. 11,292,820, which is a continuation of application No. PCT/EP2020/076187, filed on Sep. 18, 2020.

(30) Foreign Application Priority Data

Sep. 20, 2019 (EP) .................... 19198763
May 5, 2020 (EP) .................... 20172989

(51) Int. Cl.
*A61K 38/17* (2006.01)
*C07K 14/435* (2006.01)
*A61K 38/00* (2006.01)
*C07K 1/00* (2006.01)

(52) U.S. Cl.
CPC ........ *C07K 14/43522* (2013.01); *A61K 38/00* (2013.01); *C07K 1/00* (2013.01)

(58) Field of Classification Search
None
See application file for complete search history.

(56) References Cited

FOREIGN PATENT DOCUMENTS

| WO | WO-98/11125 A1 | 3/1998 |
| WO | WO-2006/002850 A2 | 1/2006 |
| WO | WO-2006/042151 A2 | 4/2006 |
| WO | WO-2006/116156 A2 | 11/2006 |
| WO | WO-2008/088422 A2 | 7/2008 |
| WO | WO-2010/105184 A2 | 9/2010 |
| WO | WO-2014/116937 A1 | 7/2014 |
| WO | WO-2015/013330 A2 | 1/2015 |
| WO | WO-2016/112208 A2 | 7/2016 |

OTHER PUBLICATIONS

Reynaud, Steve et al; "A venomics approach coupled to high throughput toxin production strategies identifies the first venom derived melanocortin receptor agonists" J. Med. Chem. (2020) 63 p. 8250-8264.*
Abdel-Mottaleb et al., "OdK2, a Kv1.3 channel-selective toxin from the venom of the Iranian scorpion *Odonthobuthus doriae*," Toxicon 51:1424-30 (2008).
Abdul et al., "Activity of Potassium Channel-blockers in Breast Cancer," Anticancer Res 23:3347-3351 (2003).
Bartok et al., "An engineered scorpion toxin analogue with improved Kv1.3 selectivity displays reduced conformational flexibility," Scientific Reports, 5(1), 13 pages (2015).
Beeton et al., "Kv1.3 channels are a therapeutic target for T cell-mediated autoimmune disease," Proc. Natl. Acad. Sci. U S A. 103:17414-9 (2006).
Beeton et al., "Targeting Effector Memory T Cells with a Selective Peptide Inhibitor of Kv1.3 Channels for Therapy of Autoimmune Dieases," Mol Pharmacol 67:1369-1381 (2005).
Bielanska et al., "Voltage-Dependent Potassium Channels Kv1.3 and Kv1.5 in Human Cancer," Curr. Cancer Drug Targets 9:904-14 (2009).
Cahalan et al., "The functional network of ion channels in T lymphocytes," Immunol. Rev. 231:59-87 (2009).
Chandy et al., "K+channels as targets for specific immunomodulation," Trends in Pharmacol. Sci. 25(5):280-289 (2004).
Cheong et al., "Potent suppression of vascular smooth muscle cell migration and human neointimal hyperplasia by Kv1.3 channel blockers," Cardiovasc. Res. 89:282-9 (2011).
Fields et al., "Principles and Practice of Solid-Phase Peptide Synthesis", In Synthetic Peptides (2nd Edition), Chapter 3:93-219 (2002).
Fraser et al., "Predominant expression of Kv1.3 voltage-gated K+ channel subunit in rat prostate cancer cell lines: electrophysiological, pharmacological and molecular characterisation," Pflugers Arch 446:559-571 (2003).
Hyodo et al., "Voltage-gated potassium channel Kv1.3 blocker as a potential treatment for rat anti-glomerular basement membrane glomerulonephritis," Am. J. Physiol. Renal Physiol. 299:F1258-69 (2010).
International Search Report and Written Opinion from International Application No. PCT/EP2020/076187 dated Mar. 1, 2021.
Khanna et al., "K+channels and the microglial respiratory burst," Am. J. Physiol. Cell Physiol. 280:C796-806 (2001).
Koo et al., "Blockade of the Voltage-Gated Potassium Channel Kv1.3 Inhibits Immune Responses in Vivo," J. Immunol. 158:5120-5128 (1997).
Koo et al., "Correolide and Derivatives are Novel Immunosuppressants Blocking the Lymphocyte Kv1.3 Potassium Channels," Cellular Immunology, 197:99-107 (1999).
Mouhat et al., "K+channel types targeted by synthetic OSK1, a toxin from *Orthochrius scrobiculosus* scorpion venom," Biochem. J. 385:95-104 (2005).

(Continued)

*Primary Examiner* — Fred H Reynolds
(74) *Attorney, Agent, or Firm* — MARSHALL, GERSTEIN & BORUN LLP

(57) ABSTRACT

The present invention provides novel blockers of the potassium channel Kv1.3, polynucleotides encoding them, and methods of making and using them.

14 Claims, No Drawings

Specification includes a Sequence Listing.

(56) References Cited

OTHER PUBLICATIONS

Rangaraju et al., "Kv1.3 potassium channels as a therapeutic target in multiple sclerosis," Expert Opin. Ther. Targets 13:909-24 (2009).
Tarcha et al., "Durable Pharmacological Responses from the Peptide ShK-186, a Specific Kv1.3 Channel Inhibitor that Suppresses T Cell Mediators of Autoimmune Disease," J. Pharmacol. Exp. Ther. 342(3):642-653 (2012).
Tschritter et al., "A New Variant in the Human Kv1.3 Gene is Associated with Low Insulin Sensitivity and Impaired Glucose Tolerance," Clin Endocrinol Metab 91:654-8 (2006).
Valverde et al., "Selective Blockade of Voltage-Gated Potassium Channels Reduces Inflammatory Bone Resorption in Experimental Periodontal Disease," J Bone Mineral Res 19:155-164 (2004).
Wang et al., "Activated T-Cells Inhibit Neurogenesis by Releasing Granzyme B: Rescue by Kv1.3 Blockers," J. Neurosci. 30:5020-7 (2010).
Wang et al., "Rational design of a Kv1.3 channel-blocking antibody as a selective immunosuppressant," Proc. Natl. Acad. Sci. USA 113(41):11501-11506 (2016).
Xu et al., "The voltage-gated potassium channel Kv1.3 regulates energy homeostasis and body weight," Hum. Mol. Genet. 12:551-9 (2003).
Xu et al., "The voltage-gated potassium channel Kv1.3 regulates peripheral insulin sensitivity," Proc Natl Acad Sci 101:3112-3117 (2004).
Yuan et al., "Jingzhaotoxin-XII, a gating modifier specific for Kv4.1 channels," Toxicon, 50(5):646-652 (2007).

\* cited by examiner

SEQUENCE LISTING

```
<160> NUMBER OF SEQ ID NOS: 180

<210> SEQ ID NO 1
<211> LENGTH: 37
<212> TYPE: PRT
<213> ORGANISM: Unknown
<220> FEATURE:
<223> OTHER INFORMATION: Parabuthus transvaalicus toxin (PaT1)

<400> SEQUENCE: 1

Gln Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 2
<211> LENGTH: 37
<212> TYPE: PRT
<213> ORGANISM: Unknown
<220> FEATURE:
<223> OTHER INFORMATION: Parabuthus transvaalicus toxin (PaT2)

<400> SEQUENCE: 2

Gln Met Asp Met Arg Cys Ser Ala Ser Val Glu Cys Lys Gln Lys Cys
1               5                   10                  15

Leu Lys Ala Ile Gly Arg Gly Phe Gly Lys Cys Met Asn Lys Lys Cys
            20                  25                  30

Lys Cys Tyr Pro Arg
        35

<210> SEQ ID NO 3
```

-continued

```
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 3

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 4
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 4

Asn Met Asp Met Arg Cys Ser Ala Ser Val Glu Cys Lys Gln Lys Cys
1               5                   10                  15

Leu Lys Ala Ile Gly Arg Gly Phe Gly Lys Cys Met Asn Lys Lys Cys
            20                  25                  30

Lys Cys Tyr Pro Arg
        35

<210> SEQ ID NO 5
<211> LENGTH: 36
<212> TYPE: PRT
<213> ORGANISM: Artificial Sequence
<220> FEATURE:
<223> OTHER INFORMATION: Modified SEQ ID NO 1

<400> SEQUENCE: 5

Met Asp Met Arg Cys Ser Ala Ser Val Glu Cys Lys Gln Lys Cys Leu
1               5                   10                  15

Lys Ala Ile Gly Ser Ile Phe Gly Lys Cys Met Asn Lys Lys Cys Lys
            20                  25                  30

Cys Tyr Pro Arg
        35

<210> SEQ ID NO 6
<211> LENGTH: 35
<212> TYPE: PRT
<213> ORGANISM: Artificial Sequence
<220> FEATURE:
<223> OTHER INFORMATION: Modified SEQ ID NO 1

<400> SEQUENCE: 6

Asp Met Arg Cys Ser Ala Ser Val Glu Cys Lys Gln Lys Cys Leu Lys
1               5                   10                  15

Ala Ile Gly Ser Ile Phe Gly Lys Cys Met Asn Lys Lys Cys Lys Cys
            20                  25                  30

Tyr Pro Arg
        35

<210> SEQ ID NO 7
<211> LENGTH: 37
<212> TYPE: PRT
<213> ORGANISM: Artificial Sequence
```

<220> FEATURE:
<223> OTHER INFORMATION: Modified SEQ ID NO 1

<400> SEQUENCE: 7

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 8
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 8

Asn Ile Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 9
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 9

Asn Met Asp Val Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 10
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 10

Asn Met Asp Met Arg Cys Ser Ala Ser Val Glu Cys Lys Gln Lys Cys
1               5                   10                  15

Lys Asp Ala Ile Gly Ser Ile Phe Gly Lys Cys Met Asn Lys Lys Cys
            20                  25                  30

Lys Cys Tyr Pro Arg
        35

<210> SEQ ID NO 11
<211> LENGTH: 39
<212> TYPE: PRT
<213> ORGANISM: Artificial Sequence
<220> FEATURE:
<223> OTHER INFORMATION: Modified SEQ ID NO 1

```
<400> SEQUENCE: 11

Gly Gly Asn Met Asp Met Arg Cys Ser Ala Ser Val Glu Cys Lys Gln
1               5                   10                  15

Lys Cys Leu Lys Ala Ile Gly Ser Ile Phe Gly Lys Cys Met Asn Lys
            20                  25                  30

Lys Cys Lys Cys Tyr Pro Arg
        35

<210> SEQ ID NO 12
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 12

Asn Met Glu Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 13
<211> LENGTH: 39
<212> TYPE: PRT
<213> ORGANISM: Artificial Sequence
<220> FEATURE:
<223> OTHER INFORMATION: Modified SEQ ID NO 1

<400> SEQUENCE: 13

Ser Gly Asn Met Asp Met Arg Cys Ser Ala Ser Val Glu Cys Lys Gln
1               5                   10                  15

Lys Cys Leu Lys Ala Ile Gly Ser Ile Phe Gly Lys Cys Met Asn Lys
            20                  25                  30

Lys Cys Lys Cys Tyr Pro Arg
        35

<210> SEQ ID NO 14
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine

<400> SEQUENCE: 14

Asn Xaa Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 15
<211> LENGTH: 37
<212> TYPE: PRT
<213> ORGANISM: Artificial Sequence
<220> FEATURE:
<223> OTHER INFORMATION: Modified SEQ ID NO 1
```

```
<220> FEATURE:
<221> NAME/KEY: MISC_FEATURE
<222> LOCATION: (4)..(4)
<223> OTHER INFORMATION: Xaa is norleucine

<400> SEQUENCE: 15

Asn Met Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 16
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (28)..(28)
<223> OTHER INFORMATION: Xaa is norleucine

<400> SEQUENCE: 16

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 17
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 17

Asn Met Asp Met Arg Cys Ser Ala Ser Val Glu Cys Lys Val Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 18
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 18

Asn Met Asp Met Arg Cys Ser Ala Ser Val Glu Cys Lys Gln Leu Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 19
```

<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 19

Asn Met Asp Met Arg Cys Ser Ala Ser Val Glu Cys Lys Gln Lys Cys
1               5                   10                  15

Lys Lys Ala Ile Gly Ser Ile Phe Gly Lys Cys Met Asn Lys Lys Cys
            20                  25                  30

Lys Cys Tyr Pro Arg
        35

<210> SEQ ID NO 20
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 20

Asn Met Asp Met Arg Cys Ser Ala Ser Val Glu Cys Lys Gln Lys Cys
1               5                   10                  15

Leu Asp Ala Ile Gly Ser Ile Phe Gly Lys Cys Met Asn Lys Lys Cys
            20                  25                  30

Lys Cys Tyr Pro Arg
        35

<210> SEQ ID NO 21
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 21

Asn Met Asp Met Arg Cys Ser Ala Ser Val Glu Cys Lys Gln Lys Cys
1               5                   10                  15

Leu Lys Ala Ile Arg Ser Ile Phe Gly Lys Cys Met Asn Lys Lys Cys
            20                  25                  30

Lys Cys Tyr Pro Arg
        35

<210> SEQ ID NO 22
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 22

Asn Met Asp Met Arg Cys Ser Ala Ser Val Glu Cys Lys Gln Lys Cys
1               5                   10                  15

Leu Lys Ala Ile Glu Ser Ile Phe Gly Lys Cys Met Asn Lys Lys Cys
            20                  25                  30

Lys Cys Tyr Pro Arg
        35

<210> SEQ ID NO 23
<211> LENGTH: 41
<212> TYPE: PRT
<213> ORGANISM: Artificial Sequence

```
<220> FEATURE:
<223> OTHER INFORMATION: Modified SEQ ID NO 1

<400> SEQUENCE: 23

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg Arg Arg Thr Ala
            35                  40

<210> SEQ ID NO 24
<211> LENGTH: 41
<212> TYPE: PRT
<213> ORGANISM: Artificial Sequence
<220> FEATURE:
<223> OTHER INFORMATION: Modified SEQ ID NO 1

<400> SEQUENCE: 24

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg His Arg Arg Lys
            35                  40

<210> SEQ ID NO 25
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 25

Asn Met Asp Met Arg Cys Lys Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
            35

<210> SEQ ID NO 26
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 26

Asn Met Asp Met Arg Cys Ser Ile Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
            35

<210> SEQ ID NO 27
<211> LENGTH: 37
<212> TYPE: PRT
<213> ORGANISM: Artificial Sequence
<220> FEATURE:
<223> OTHER INFORMATION: Modified SEQ ID NO 1
```

<400> SEQUENCE: 27

Asn Met Asp Met Arg Cys Ser Ala Ser Arg Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 28
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 28

Asn Met Asp Met Arg Cys Ser Ala Ser Val Gln Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 29
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 29

Asn Met Asp Met Arg Cys Ser Ala Ser Val Glu Cys Leu Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 30
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 30

Asn Met Asp Met Arg Cys Ser Ala Ser Val Glu Cys Ala Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 31
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 31

Asn Met Asp Met Arg Cys Ser Ala Ser Val Glu Cys Lys Glu Lys Cys

```
 1               5                   10                  15
Leu Lys Ala Ile Gly Ser Ile Phe Gly Lys Cys Met Asn Lys Cys
            20                  25                  30

Lys Cys Tyr Pro Arg
        35

<210> SEQ ID NO 32
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 32

Asn Met Asp Met Arg Cys Ser Ala Ser Val Glu Cys Lys Leu Lys Cys
1               5                   10                  15

Leu Lys Ala Ile Gly Ser Ile Phe Gly Lys Cys Met Asn Lys Cys
            20                  25                  30

Lys Cys Tyr Pro Arg
        35

<210> SEQ ID NO 33
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 33

Asn Met Asp Met Arg Cys Ser Ala Ser Val Glu Cys Lys Gln Lys Cys
1               5                   10                  15

Leu Lys Ala Ile His Ser Ile Phe Gly Lys Cys Met Asn Lys Cys
            20                  25                  30

Lys Cys Tyr Pro Arg
        35

<210> SEQ ID NO 34
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 34

Asn Met Asp Met Arg Cys Ser Ala Ser Val Glu Cys Lys Gln Lys Cys
1               5                   10                  15

Leu Lys Ala Ile Gly Ser Lys Phe Gly Lys Cys Met Asn Lys Cys
            20                  25                  30

Lys Cys Tyr Pro Arg
        35

<210> SEQ ID NO 35
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 35

Asn Met Asp Met Arg Cys Ser Ala Ser Val Glu Cys Lys Gln Lys Cys
1               5                   10                  15

Leu Lys Ala Ile Gly Ser Arg Phe Gly Lys Cys Met Asn Lys Cys
```

```
                20                  25                  30

Lys Cys Tyr Pro Arg
        35

<210> SEQ ID NO 36
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 36

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Gly Lys Cys
            20                  25                  30

Lys Cys Tyr Pro Arg
        35

<210> SEQ ID NO 37
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 37

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

His Cys Tyr Pro Arg
        35

<210> SEQ ID NO 38
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 38

Asn Met Asp Met Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Val Cys Tyr Pro Arg
        35

<210> SEQ ID NO 39
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 39
```

Asn Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 40
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 40

Asn Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 41
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 41

Pro Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 42
<211> LENGTH: 37
<212> TYPE: PRT
<213> ORGANISM: Artificial Sequence
<220> FEATURE:
<223> OTHER INFORMATION: Modified SEQ ID NO 1

```
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 42

Asn Xaa Asp Xaa Arg Cys Arg Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 43
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 43

Asn Xaa Asp Xaa Arg Cys Ser Ala Ser Val Glu Cys Glu Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 44
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 44

Asn Xaa Asp Xaa Arg Cys Ser Ala Ser Val Glu Cys Gln Gln Lys Cys
1               5                   10                  15
```

-continued

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 45
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 45

Asn Xaa Asp Xaa Arg Cys Ser Ala Ser Val Glu Cys Lys Lys Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 46
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 46

Asn Xaa Ser Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 47
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)

```
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 47

Asn Xaa Asp Xaa Arg Cys Ser His Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 48
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 48

Asn Xaa Asp Xaa Arg Cys Ser Ala Ser Val Glu Cys Lys Gln Ser Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 49
<211> LENGTH: 36
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (27)..(27)
<223> OTHER INFORMATION: Xaa is norleucine

<400> SEQUENCE: 49

Asn Xaa Asp Xaa Arg Cys Ser Ala Ser Val Glu Cys Lys Gln Lys Cys
1               5                   10                  15

Lys Ala Ile Gly Ser Ile Phe Gly Lys Cys Xaa Asn Lys Lys Cys Lys
            20                  25                  30
```

Cys Tyr Pro Arg
        35

<210> SEQ ID NO 50
<211> LENGTH: 37
<212> TYPE: PRT
<213> ORGANISM: Artificial Sequence
<220> FEATURE:
<223> OTHER INFORMATION: Modified EQ ID NO 1

<400> SEQUENCE: 50

Asn Met Asp Met Arg Cys Ser Ala Ser Val Glu Cys Lys Gln Lys Cys
1               5                   10                  15

Tyr Lys Ala Ile Gly Ser Ile Phe Gly Lys Cys Met Asn Lys Lys Cys
            20                  25                  30

Lys Cys Tyr Pro Arg
        35

<210> SEQ ID NO 51
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 51

Asn Met Asp Met Arg Cys Ser Ala Ser Val Glu Cys Lys Gln Lys Cys
1               5                   10                  15

Arg Lys Ala Ile Gly Ser Ile Phe Gly Lys Cys Met Asn Lys Lys Cys
            20                  25                  30

Lys Cys Tyr Pro Arg
        35

<210> SEQ ID NO 52
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 52

Asn Met Asp Met Arg Cys Ser Ala Ser Val Glu Cys Lys Gln Lys Cys
1               5                   10                  15

Leu Ala Ala Ile Gly Ser Ile Phe Gly Lys Cys Met Asn Lys Lys Cys
            20                  25                  30

Lys Cys Tyr Pro Arg
        35

<210> SEQ ID NO 53
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 53

Asn Met Asp Met Arg Cys Ser Ala Ser Val Glu Cys Lys Gln Lys Cys
1               5                   10                  15

Leu Tyr Ala Ile Gly Ser Ile Phe Gly Lys Cys Met Asn Lys Lys Cys
            20                  25                  30

Lys Cys Tyr Pro Arg
        35

<210> SEQ ID NO 54
<211> LENGTH: 36
<212> TYPE: PRT
<213> ORGANISM: Artificial Sequence
<220> FEATURE:
<223> OTHER INFORMATION: Modified SEQ ID NO 1

<400> SEQUENCE: 54

Asn Met Asp Met Arg Cys Ser Ala Ser Val Glu Cys Lys Gln Lys Cys
1               5                   10                  15

Leu Ala Ile Gly Ser Ile Phe Gly Lys Cys Met Asn Lys Lys Cys Lys
            20                  25                  30

Cys Tyr Pro Arg
        35

<210> SEQ ID NO 55
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 55

Asn Met Asp Met Arg Cys Ser Ala Ser Val Glu Cys Lys Gln Lys Cys
1               5                   10                  15

Leu Lys Tyr Ile Gly Ser Ile Phe Gly Lys Cys Met Asn Lys Lys Cys
            20                  25                  30

Lys Cys Tyr Pro Arg
        35

<210> SEQ ID NO 56
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 56

Asn Met Asp Met Arg Cys Ser Ala Ser Val Glu Cys Lys Gln Lys Cys
1               5                   10                  15

Leu Lys Arg Ile Gly Ser Ile Phe Gly Lys Cys Met Asn Lys Lys Cys
            20                  25                  30

Lys Cys Tyr Pro Arg
        35

<210> SEQ ID NO 57
<211> LENGTH: 36
<212> TYPE: PRT
<213> ORGANISM: Artificial Sequence
<220> FEATURE:
<223> OTHER INFORMATION: Modified SEQ ID NO 1

<400> SEQUENCE: 57

Asn Met Asp Met Arg Cys Ser Ala Ser Val Glu Cys Lys Gln Lys Cys
1               5                   10                  15

Leu Lys Ile Gly Ser Ile Phe Gly Lys Cys Met Asn Lys Lys Cys Lys
            20                  25                  30

Cys Tyr Pro Arg
        35

<210> SEQ ID NO 58

<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 58

Asn Met Asp Met Arg Cys Ser Ala Ser Val Glu Cys Lys Gln Lys Cys
1               5                   10                  15

Leu Lys Ala Tyr Gly Ser Ile Phe Gly Lys Cys Met Asn Lys Lys Cys
            20                  25                  30

Lys Cys Tyr Pro Arg
        35

<210> SEQ ID NO 59
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 59

Asn Met Asp Met Arg Cys Ser Ala Ser Val Glu Cys Lys Gln Lys Cys
1               5                   10                  15

Leu Lys Ala Glu Gly Ser Ile Phe Gly Lys Cys Met Asn Lys Lys Cys
            20                  25                  30

Lys Cys Tyr Pro Arg
        35

<210> SEQ ID NO 60
<211> LENGTH: 37
<212> TYPE: PRT
<213> ORGANISM: Artificial Sequence
<220> FEATURE:
<223> OTHER INFORMATION: Modified SEQ ID NO 1

<400> SEQUENCE: 60

Asn Met Asp Met Arg Cys Ser Ala Ser Val Glu Cys Lys Gln Lys Cys
1               5                   10                  15

Leu Lys Ala Arg Gly Ser Ile Phe Gly Lys Cys Met Asn Lys Lys Cys
            20                  25                  30

Lys Cys Tyr Pro Arg
        35

<210> SEQ ID NO 61
<211> LENGTH: 36
<212> TYPE: PRT
<213> ORGANISM: Artificial Sequence
<220> FEATURE:
<223> OTHER INFORMATION: Modified SEQ ID NO 1

<400> SEQUENCE: 61

Asn Met Asp Met Arg Cys Ser Ala Ser Val Glu Cys Lys Gln Lys Cys
1               5                   10                  15

Leu Lys Ala Gly Ser Ile Phe Gly Lys Cys Met Asn Lys Lys Cys Lys
            20                  25                  30

Cys Tyr Pro Arg
        35

<210> SEQ ID NO 62
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 62

Asn Xaa Asp Xaa Arg Cys Ser Ala Ser Val Glu Cys Lys Gln Lys Cys
1               5                   10                  15

Leu Lys Ala Ile Gly Ser Pro Phe Gly Lys Cys Xaa Asn Lys Lys Cys
            20                  25                  30

Lys Cys Tyr Pro Arg
        35

<210> SEQ ID NO 63
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 63

Asn Xaa Asp Xaa Arg Cys Ser Ala Ser Lys Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 64
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 64

```
His Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 65
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 65

Tyr Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 66
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 66

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 67
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
```

```
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 67

Val Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 68
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (9)..(9)
<223> OTHER INFORMATION: Xaa is alpha-aminobutyric acid (homo-alanine)

<400> SEQUENCE: 68

Ser Xaa Asp Xaa Arg Cys Ser Ala Xaa Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 69
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (26)..(26)
<223> OTHER INFORMATION: Xaa is homo-lysine

<400> SEQUENCE: 69

Ser Xaa Asp Xaa Arg Cys Ser Ala Ser Val Glu Cys Lys Gln Lys Cys
1               5                   10                  15
```

Leu Lys Ala Ile Gly Ser Ile Phe Gly Xaa Cys Met Asn Lys Lys Cys
            20                  25                  30

Lys Cys Tyr Pro Arg
        35

<210> SEQ ID NO 70
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (35)..(35)
<223> OTHER INFORMATION: Xaa is 4-amino-phenylalanine

<400> SEQUENCE: 70

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Xaa Pro Arg
        35

<210> SEQ ID NO 71
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 71

Ser Xaa Asp Xaa Arg Cys Ser Ala Ser Val Glu Cys Gly Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 72
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 72

Ser Xaa Asp Xaa Arg Cys Ser Ala Ser Val Glu Cys Val Gln Lys Cys
1               5                   10                  15

Leu Lys Ala Ile Gly Ser Ile Phe Gly Lys Cys Met Asn Lys Lys Cys
                20                  25                  30

Lys Cys Tyr Pro Arg
            35

<210> SEQ ID NO 73
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (14)..(14)
<223> OTHER INFORMATION: Xaa is 2-amino-5-carboxypentanoyl

<400> SEQUENCE: 73

Ser Xaa Asp Xaa Arg Cys Ser Ala Ser Val Glu Cys Lys Xaa Lys Cys
1               5                   10                  15

Leu Lys Ala Ile Gly Ser Ile Phe Gly Lys Cys Met Asn Lys Lys Cys
                20                  25                  30

Lys Cys Tyr Pro Arg
            35

<210> SEQ ID NO 74
<211> LENGTH: 36
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 74

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
                20                  25                  30

Lys Cys Tyr Gln
            35

<210> SEQ ID NO 75
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE

```
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 75

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Arg Cys Tyr Pro Arg
            35

<210> SEQ ID NO 76
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine

<400> SEQUENCE: 76

Ser Xaa Asp Glu Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
            35

<210> SEQ ID NO 77
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 77

Ser Xaa Asp Xaa Arg Cys Ser Ala Ser Val Glu Cys Lys Gln Lys Cys
1               5                   10                  15

Leu Gly Ala Ile Gly Ser Ile Phe Gly Lys Cys Met Asn Lys Lys Cys
            20                  25                  30

Lys Cys Tyr Pro Arg
            35

<210> SEQ ID NO 78
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
```

<220> FEATURE:
<221> NAME/KEY: MISC_FEATURE
<222> LOCATION: (4)..(4)
<223> OTHER INFORMATION: Xaa is norleucine

<400> SEQUENCE: 78

Ser Xaa Asp Xaa Arg Cys Ser Ala Ser Val Glu Cys Lys Gln Lys Cys
1               5                   10                  15

Leu Val Ala Ile Gly Ser Ile Phe Gly Lys Cys Met Asn Lys Lys Cys
            20                  25                  30

Lys Cys Tyr Pro Arg
        35

<210> SEQ ID NO 79
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 79

Ser Xaa Asp Xaa Arg Cys Ser Ala Ser Val Glu Cys Ala Gln Ser Cys
1               5                   10                  15

Leu Lys Ala Ile Gly Ser Ile Phe Gly Lys Cys Met Asn Lys Lys Cys
            20                  25                  30

Lys Cys Tyr Pro Arg
        35

<210> SEQ ID NO 80
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 80

Ser Xaa Asp Xaa Arg Cys Ser Ala Ser Val Glu Cys Ala Gln Lys Cys
1               5                   10                  15

Leu Ala Ala Ile Gly Ser Ile Phe Gly Lys Cys Met Asn Lys Lys Cys
            20                  25                  30

Lys Cys Tyr Pro Arg
        35

<210> SEQ ID NO 81
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE

```
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 81

Ser Xaa Asp Xaa Arg Cys Ser Ala Ser Val Glu Cys Ala Gln Leu Cys
1               5                   10                  15

Leu Ala Ala Ile Gly Ser Ile Phe Gly Lys Cys Met Asn Lys Lys Cys
            20                  25                  30

Lys Cys Tyr Pro Arg
        35

<210> SEQ ID NO 82
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 82

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 83
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 83

Pro Xaa Asp Xaa Arg Cys Ser Ala Ser Val Glu Cys Lys Gln Lys Cys
1               5                   10                  15

Leu Lys Ala Ile Gly Cys Ile Phe Gly Lys Cys Xaa Asn Lys Lys Cys
            20                  25                  30

Lys Cys Tyr Pro Cys
        35
```

<210> SEQ ID NO 84
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 84

Ser Xaa Asp Xaa Arg Cys Ser Ala Ser Val Glu Cys Lys Glu Lys Cys
1               5                   10                  15

Leu Gln Ala Ile Gly Ser Ile Phe Gly Lys Cys Xaa Asn Lys Lys Cys
            20                  25                  30

Lys Cys Tyr Pro Arg
        35

<210> SEQ ID NO 85
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (18)..(18)
<223> OTHER INFORMATION: Xaa is homo-glutamine
<220> FEATURE:
<221> NAME/KEY: MISC_FEATURE
<222> LOCATION: (28)..(28)
<223> OTHER INFORMATION: Xaa is norleucine

<400> SEQUENCE: 85

Pro Xaa Asp Xaa Arg Cys Ser Ala Ser Val Glu Cys Lys Glu Lys Cys
1               5                   10                  15

Leu Xaa Ala Ile Gly Ser Ile Phe Gly Lys Cys Xaa Asn Lys Lys Cys
            20                  25                  30

Lys Cys Tyr Pro Arg
        35

<210> SEQ ID NO 86
<211> LENGTH: 32
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (23)..(23)
<223> OTHER INFORMATION: Xaa is norleucine

<400> SEQUENCE: 86

Cys Ser Ala Ser Val Glu Cys Lys Gln Lys Cys Leu Lys Ala Ile Gly
1               5                   10                  15

Cys Ile Phe Gly Lys Cys Xaa Asn Lys Lys Cys Lys Cys Tyr Pro Cys
            20                  25                  30

<210> SEQ ID NO 87
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 87

Ser Xaa Asp Xaa Arg Cys Ser Ala Ser Val Glu Cys Lys Gln Lys Cys
1               5                   10                  15

Leu Ala Ala Ile Gly Cys Ile Phe Gly Lys Cys Xaa Asn Lys Lys Cys
            20                  25                  30

Lys Cys Tyr Pro Cys
            35

<210> SEQ ID NO 88
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 88

Pro Xaa Asp Xaa Arg Cys Ser Ala Ser Val Glu Cys Lys Gln Lys Cys
1               5                   10                  15

Leu Lys Ala Ile Gly Cys Ile Phe Gly Lys Cys Xaa Asn Lys Lys Cys
            20                  25                  30

Lys Cys Tyr Pro Cys
            35

<210> SEQ ID NO 89
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE

```
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 89

Ser Xaa Asp Xaa Arg Cys Ser Ala Leu Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
            35

<210> SEQ ID NO 90
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 90

Ser Xaa Asp Xaa Arg Cys Ser Ala Val Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Tyr Pro Arg
            35

<210> SEQ ID NO 91
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (35)..(35)
<223> OTHER INFORMATION: Xaa is 4-fluoro-phenylalanine

<400> SEQUENCE: 91

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Xaa Pro Arg
            35

<210> SEQ ID NO 92
<211> LENGTH: 37
```

```
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (35)..(35)
<223> OTHER INFORMATION: Xaa is 4-nitro-phenylalanine

<400> SEQUENCE: 92

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Xaa Pro Arg
        35

<210> SEQ ID NO 93
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (35)..(35)
<223> OTHER INFORMATION: Xaa is 4-methyl-phenylalanine

<400> SEQUENCE: 93

Ser Xaa Asp Xaa Arg Cys Ser Ala Ser Val Glu Cys Lys Gln Lys Cys
1               5                   10                  15

Leu Lys Ala Ile Gly Ser Ile Phe Gly Lys Cys Met Asn Lys Lys Cys
            20                  25                  30

Lys Cys Xaa Pro Arg
        35

<210> SEQ ID NO 94
<211> LENGTH: 36
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (1)..(1)
<223> OTHER INFORMATION: Xaa is norleucine
<220> FEATURE:
<221> NAME/KEY: MISC_FEATURE
<222> LOCATION: (3)..(3)
<223> OTHER INFORMATION: Xaa is norleucine
<220> FEATURE:
<221> NAME/KEY: MISC_FEATURE
<222> LOCATION: (27)..(27)
<223> OTHER INFORMATION: Xaa is norleucine
```

```
<400> SEQUENCE: 94

Xaa Asp Xaa Arg Cys Ser Ala Ser Val Glu Cys Lys Gln Lys Cys Leu
1               5                   10                  15

Lys Ala Ile Gly Ser Ile Phe Gly Lys Cys Xaa Asn Lys Lys Cys Lys
            20                  25                  30

Cys Tyr Pro Arg
        35

<210> SEQ ID NO 95
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 95

Asn Ile Asp Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 96
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 96

Pro Ile Glu Xaa Arg Cys Ser Ala Ser Val Glu Cys Lys Gln Lys Cys
1               5                   10                  15

Leu Lys Ala Ile Gly Ser Ile Phe Gly Lys Cys Xaa Asn Lys Lys Cys
            20                  25                  30

Lys Cys Tyr Pro Arg
        35

<210> SEQ ID NO 97
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
```

<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 97

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 98
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 98

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 99
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 99

Pro Xaa Glu Xaa Arg Cys Ser Ala Ser Val Glu Cys Lys Gln Lys Cys
1               5                   10                  15

Leu Leu Ala Ile Gly Ser Ile Phe Gly Lys Cys Xaa Asn Lys Lys Cys
            20                  25                  30

Lys Cys Tyr Pro Arg
        35

```
<210> SEQ ID NO 100
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (28)..(28)
<223> OTHER INFORMATION: Xaa is norleucine

<400> SEQUENCE: 100

Pro Ile Asp Glu Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 101
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 101

Pro Ile Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 102
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine

<400> SEQUENCE: 102

Pro Xaa Asp Xaa Arg Cys Ser Ala Ser Val Glu Cys Ala Gln Lys Cys
1               5                   10                  15

Leu Ala Ala Ile Gly Ser Ile Phe Gly Lys Cys Met Asn Lys Lys Cys
            20                  25                  30

Lys Cys Tyr Pro Arg
        35

<210> SEQ ID NO 103
```

```
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 103

Pro Xaa Glu Xaa Arg Cys Ser Ala Ser Val Glu Cys Ala Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 104
<211> LENGTH: 32
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (23)..(23)
<223> OTHER INFORMATION: Xaa is norleucine

<400> SEQUENCE: 104

Cys Ser Ala Ser Val Glu Cys Lys Gln Lys Cys Leu Lys Ala Ile Gly
1               5                   10                  15

Ser Ile Phe Gly Lys Cys Xaa Asn Lys Lys Cys Lys Cys Tyr Pro Arg
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (23)..(23)
<223> OTHER INFORMATION: Xaa is norleucine

<400> SEQUENCE: 105

Cys Ser Ala Ser Val Glu Cys Lys Gln Lys Cys Leu Lys Ala Ile Gly
1               5                   10                  15

Ser Ile Phe Gly Lys Cys Xaa Asn Lys Lys Cys Lys Cys Tyr Pro Arg
            20                  25                  30

<210> SEQ ID NO 106
<211> LENGTH: 33
<212> TYPE: PRT
<213> ORGANISM: Artificial Sequence
<220> FEATURE:
```

```
<223> OTHER INFORMATION: Modified SEQ ID NO 1
<220> FEATURE:
<221> NAME/KEY: MISC_FEATURE
<222> LOCATION: (24)..(24)
<223> OTHER INFORMATION: Xaa is norleucine

<400> SEQUENCE: 106

Arg Cys Ser Ala Ser Val Glu Cys Lys Gln Lys Cys Leu Lys Ala Ile
1               5                   10                  15

Gly Ser Ile Phe Gly Lys Cys Xaa Asn Lys Lys Cys Lys Cys Tyr Pro
            20                  25                  30

Arg

<210> SEQ ID NO 107
<211> LENGTH: 34
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (25)..(25)
<223> OTHER INFORMATION: Xaa is norleucine

<400> SEQUENCE: 107

Ser Lys Cys Ser Ala Ser Val Glu Cys Lys Gln Lys Cys Leu Lys Ala
1               5                   10                  15

Ile Gly Ser Ile Phe Gly Lys Cys Xaa Asn Lys Lys Cys Lys Cys Tyr
            20                  25                  30

Pro Arg

<210> SEQ ID NO 108
<211> LENGTH: 34
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (25)..(25)
<223> OTHER INFORMATION: Xaa is norleucine

<400> SEQUENCE: 108

Leu Arg Cys Ser Ala Ser Val Glu Cys Lys Gln Lys Cys Leu Lys Ala
1               5                   10                  15

Ile Gly Ser Ile Phe Gly Lys Cys Xaa Asn Lys Lys Cys Lys Cys Tyr
            20                  25                  30

Pro Arg

<210> SEQ ID NO 109
<211> LENGTH: 32
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (23)..(23)
<223> OTHER INFORMATION: Xaa is norleucine

<400> SEQUENCE: 109

Cys Ser Ala Ser Val Glu Cys Lys Gln Lys Cys Leu Lys Ala Ile Gly
1               5                   10                  15

Ser Ile Phe Gly Lys Cys Xaa Asn Lys Lys Cys Lys Cys Tyr Pro Ser
            20                  25                  30

<210> SEQ ID NO 110
<211> LENGTH: 31
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (23)..(23)
<223> OTHER INFORMATION: Xaa is norleucine

<400> SEQUENCE: 110

Cys Ser Ala Ser Val Glu Cys Lys Gln Lys Cys Leu Lys Ala Ile Gly
1               5                   10                  15

Ser Ile Phe Gly Lys Cys Xaa Asn Lys Lys Cys Lys Cys Tyr Ser
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (23)..(23)
<223> OTHER INFORMATION: Xaa is norleucine

<400> SEQUENCE: 111

Cys Ser Ala Ser Val Glu Cys Lys Gln Lys Cys Leu Lys Ala Ile Gly
1               5                   10                  15

Ser Ile Phe Gly Lys Cys Xaa Asn Lys Lys Cys Lys Cys Tyr Gly
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Modified SEQ ID No 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (23)..(23)
<223> OTHER INFORMATION: Xaa is norleucine

<400> SEQUENCE: 112
```

-continued

```
Cys Ser Ala Ser Val Glu Cys Lys Gln Lys Cys Leu Lys Ala Ile Gly
1               5                   10                  15
Ser Ile Phe Gly Lys Cys Xaa Asn Lys Lys Cys Lys Cys Tyr
            20                  25                  30

<210> SEQ ID NO 113
<211> LENGTH: 33
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (24)..(24)
<223> OTHER INFORMATION: Xaa is norleucine

<400> SEQUENCE: 113

Arg Cys Ser Ala Ser Val Glu Cys Lys Gln Lys Cys Leu Lys Ala Ile
1               5                   10                  15
Gly Ser Ile Phe Gly Lys Cys Xaa Asn Lys Lys Cys Lys Cys Tyr Pro
            20                  25                  30
Arg

<210> SEQ ID NO 114
<211> LENGTH: 34
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (25)..(25)
<223> OTHER INFORMATION: Xaa is norleucine

<400> SEQUENCE: 114

Leu Arg Cys Ser Ala Ser Val Glu Cys Lys Gln Lys Cys Leu Lys Ala
1               5                   10                  15
Ile Gly Ser Ile Phe Gly Lys Cys Xaa Asn Lys Lys Cys Lys Cys Tyr
            20                  25                  30
Pro Arg

<210> SEQ ID NO 115
<211> LENGTH: 34
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (25)..(25)
<223> OTHER INFORMATION: Xaa is norleucine

<400> SEQUENCE: 115

Leu Arg Cys Ser Ala Ser Val Glu Cys Lys Gln Lys Cys Leu Ala Ala
1               5                   10                  15
Ile Gly Ser Ile Phe Gly Lys Cys Xaa Asn Lys Lys Cys Lys Cys Tyr
            20                  25                  30
Pro Arg
```

<210> SEQ ID NO 116
<211> LENGTH: 34
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MOD_RES
<222> LOCATION: (1)..(1)
<223> OTHER INFORMATION: ACETYLATION

<400> SEQUENCE: 116

Leu Arg Cys Ser Ala Ser Val Glu Cys Lys Gln Lys Cys Leu Ala Ala
1               5                   10                  15

Ile Gly Ser Ile Phe Gly Lys Cys Met Asn Lys Lys Cys Lys Cys Tyr
                20                  25                  30

Pro Arg

<210> SEQ ID NO 117
<211> LENGTH: 32
<212> TYPE: PRT
<213> ORGANISM: Artificial Sequence
<220> FEATURE:
<223> OTHER INFORMATION: Modified SEQ ID NO 1

<400> SEQUENCE: 117

Cys Ser Ala Ser Val Glu Cys Lys Gln Lys Cys Leu Lys Ala Ile Gly
1               5                   10                  15

Ser Ile Phe Gly Lys Cys Met Asn Lys Lys Cys Lys Cys Tyr Pro Arg
                20                  25                  30

<210> SEQ ID NO 118
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 118

Pro Xaa Glu Xaa Arg Cys Ser Ala Ser Val Glu Cys Lys Glu Lys Cys
1               5                   10                  15

Leu Ala Ala Ile Gly Ser Ile Phe Gly Lys Cys Xaa Asn Lys Lys Cys
                20                  25                  30

Lys Cys Tyr Pro Arg
            35

<210> SEQ ID NO 119
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE

```
<222> LOCATION: (1)..(1)
<223> OTHER INFORMATION: D-proline
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 119

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 120
<211> LENGTH: 36
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 120

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Arg
        35

<210> SEQ ID NO 121
<211> LENGTH: 36
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (1)..(1)
<223> OTHER INFORMATION: Xaa is norleucine
<220> FEATURE:
<221> NAME/KEY: MISC_FEATURE
<222> LOCATION: (3)..(3)
<223> OTHER INFORMATION: Xaa is norleucine
<220> FEATURE:
<221> NAME/KEY: MISC_FEATURE
<222> LOCATION: (27)..(27)
<223> OTHER INFORMATION: Xaa is norleucine

<400> SEQUENCE: 121
```

```
Xaa Glu Xaa Arg Cys Ser Ala Ser Val Glu Cys Lys Gln Lys Cys Leu
1               5                   10                  15

Ala Ala Ile Gly Ser Ile Phe Gly Lys Cys Xaa Asn Lys Cys Lys
            20                  25                  30

Cys Tyr Pro Arg
        35

<210> SEQ ID NO 122
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 122

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Cys
            20                  25                  30

Lys Cys Tyr Pro Arg Arg
        35

<210> SEQ ID NO 123
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 123

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Cys
            20                  25                  30

Lys Cys Tyr Pro Arg Tyr
        35

<210> SEQ ID NO 124
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
```

```
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 124

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Leu
        35

<210> SEQ ID NO 125
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 125

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg His
        35

<210> SEQ ID NO 126
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 126

Pro Xaa Glu Xaa Arg Cys Ser Ala Ser Val Glu Cys Lys Gln Lys Cys
1               5                   10                  15
```

Leu Ala Ala Ile Gly Ser Ile Phe Gly Lys Cys Xaa Asn Lys Lys Cys
            20                  25                  30

Lys Cys Tyr Pro Arg Glu
        35

<210> SEQ ID NO 127
<211> LENGTH: 39
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 127

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Lys Ser
        35

<210> SEQ ID NO 128
<211> LENGTH: 39
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 128

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Phe Glu
        35

<210> SEQ ID NO 129
<211> LENGTH: 39
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine

```
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 129

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg His Arg
        35

<210> SEQ ID NO 130
<211> LENGTH: 39
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 130

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Ala Lys
        35

<210> SEQ ID NO 131
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine
<220> FEATURE:
<221> NAME/KEY: MISC_FEATURE
<222> LOCATION: (37)..(37)
<223> OTHER INFORMATION: Xaa is (4-amino-5-hydroxypentyl)guanidine

<400> SEQUENCE: 131

Pro Xaa Glu Xaa Arg Cys Ser Ala Ser Val Glu Cys Lys Gln Lys Cys
1               5                   10                  15
```

-continued

```
Leu Ala Ala Ile Gly Ser Ile Phe Gly Lys Cys Xaa Asn Lys Lys Cys
            20                  25                  30

Lys Cys Tyr Pro Xaa
        35

<210> SEQ ID NO 132
<211> LENGTH: 38
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine
<220> FEATURE:
<221> NAME/KEY: MISC_FEATURE
<222> LOCATION: (38)..(38)
<223> OTHER INFORMATION: Xaa is 4-amino-5-hydroxypentanamide

<400> SEQUENCE: 132

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Xaa
        35

<210> SEQ ID NO 133
<211> LENGTH: 39
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 133

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Ser Thr
        35

<210> SEQ ID NO 134
<211> LENGTH: 39
<212> TYPE: PRT
<213> ORGANISM: Artificial Sequence
<220> FEATURE:
```

<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 134

Pro Xaa Glu Xaa Arg Cys Ser Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg Arg Tyr
            35

<210> SEQ ID NO 135
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 135

Pro Xaa Glu Xaa Arg Cys Ser Ser Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
            35

<210> SEQ ID NO 136
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 136

Pro Xaa Glu Xaa Arg Cys Ser Leu Ser Val Glu Cys Lys Gln Lys Cys

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 137
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 137

Pro Xaa Glu Xaa Arg Cys Ser Ala Pro Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 138
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 138

Pro Xaa Glu Xaa Arg Cys Ser Ala Ser Pro Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 139
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 139

Pro Xaa Glu Xaa Arg Cys Ser Ala Ser Gln Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 140
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 140

Pro Xaa Glu Xaa Arg Cys Ser Ala Ser Val Glu Cys Leu Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 141
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 141

Pro Xaa Glu Xaa Arg Cys Ser Ala Ser Val Glu Cys Lys Gln Pro Cys
1               5                   10                  15

Leu Ala Ala Ile Gly Ser Ile Phe Gly Lys Cys Xaa Asn Lys Lys Cys

Lys Cys Tyr Pro Arg
        35

<210> SEQ ID NO 142
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 142

Pro Xaa Glu Xaa Arg Cys Glu Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 143
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 143

Pro Xaa Glu Xaa Arg Cys Phe Ala Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 144
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:

```
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 144

Pro Xaa Glu Xaa Arg Cys Ser Tyr Ser Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 145
<211> LENGTH: 37
<212> TYPE: PRT
<213> ORGANISM: Artificial Sequence
<220> FEATURE:
<223> OTHER INFORMATION: Modified SEQ ID NO 1
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (4)..(4)
<223> OTHER INFORMATION: Xaa is norleucine
<220> FEATURE:
<221> NAME/KEY: MISC_FEATURE
<222> LOCATION: (28)..(28)
<223> OTHER INFORMATION: Xaa is norleucine

<400> SEQUENCE: 145

Pro Xaa Glu Xaa Arg Cys Ser Ala Phe Val Glu Cys Lys Gln Lys Cys
1               5                   10                  15

Leu Ala Ala Ile Gly Ser Ile Phe Gly Lys Cys Xaa Asn Lys Lys Cys
            20                  25                  30

Lys Cys Tyr Pro Arg
        35

<210> SEQ ID NO 146
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 146

Arg Arg Thr Ala
1

<210> SEQ ID NO 147
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 147

His Arg Arg Lys
1

<210> SEQ ID NO 148
<211> LENGTH: 4
```

```
<212> TYPE: PRT
<213> ORGANISM: Artificial Sequence
<220> FEATURE:
<223> OTHER INFORMATION: Additional C-terminal sequence

<400> SEQUENCE: 148

Gln Ser Lys Ala
1

<210> SEQ ID NO 149
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 149

Ala Gly Pro Arg
1

<210> SEQ ID NO 150
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 150

Arg Ser Arg Thr
1

<210> SEQ ID NO 151
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 151

Arg His Lys Arg
1

<210> SEQ ID NO 152
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 152

Gly Gly Lys Arg
1

<210> SEQ ID NO 153
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 153

Pro Lys Thr Ala
1

<210> SEQ ID NO 154
<211> LENGTH: 4
<212> TYPE: PRT
```

-continued

```
<213> ORGANISM: Artificial Sequence
<220> FEATURE:
<223> OTHER INFORMATION: Additional C-terminal sequence

<400> SEQUENCE: 154

Thr Asp Ala Arg
1

<210> SEQ ID NO 155
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 155

His Arg Gln Gln
1

<210> SEQ ID NO 156
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 156

Arg Pro Arg His
1

<210> SEQ ID NO 157
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 157

Ala Arg Asn Ala
1

<210> SEQ ID NO 158
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 158

Thr Gly Arg Lys
1

<210> SEQ ID NO 159
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 159

His Glu Arg Thr
1

<210> SEQ ID NO 160
<211> LENGTH: 4
<212> TYPE: PRT
<213> ORGANISM: Artificial Sequence
```

```
<220> FEATURE:
<223> OTHER INFORMATION: Additional C-terminal sequence

<400> SEQUENCE: 160

Asn Thr Arg Thr
1

<210> SEQ ID NO 161
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 161

Gln Arg Asn Gly
1

<210> SEQ ID NO 162
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 162

Ala His Arg Asn
1

<210> SEQ ID NO 163
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 163

Pro Arg Ser Ala
1

<210> SEQ ID NO 164
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 164

Gln Arg Gln Ser
1

<210> SEQ ID NO 165
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 165

Gln Arg Arg Lys
1

<210> SEQ ID NO 166
<211> LENGTH: 4
<212> TYPE: PRT
<213> ORGANISM: Artificial Sequence
<220> FEATURE:
```

```
<223> OTHER INFORMATION: Additional C-terminal sequence

<400> SEQUENCE: 166

Ala Arg Ala Lys
1

<210> SEQ ID NO 167
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 167

Ala Lys Arg Asp
1

<210> SEQ ID NO 168
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 168

Arg Asp Lys Thr
1

<210> SEQ ID NO 169
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 169

His Arg Arg Lys
1

<210> SEQ ID NO 170
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 170

Arg Ala Lys Arg
1

<210> SEQ ID NO 171
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 171

Gln Arg Thr Arg
1

<210> SEQ ID NO 172
<211> LENGTH: 4
<212> TYPE: PRT
<213> ORGANISM: Artificial Sequence
<220> FEATURE:
<223> OTHER INFORMATION: Additional C-terminal sequence
```

```
<400> SEQUENCE: 172

Ala Thr Arg His
1

<210> SEQ ID NO 173
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 173

Ala Arg Arg Ser
1

<210> SEQ ID NO 174
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 174

Ala Lys Thr Arg
1

<210> SEQ ID NO 175
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 175

Asn Arg Gln Arg
1

<210> SEQ ID NO 176
<211> LENGTH: 4
<212> TYPE: PRT
<213> ORGANISM: Artificial Sequence
<220> FEATURE:
<223> OTHER INFORMATION: Additional C-terminal sequence

<400> SEQUENCE: 176

Pro Arg Asn Thr
1

<210> SEQ ID NO 177
<211> LENGTH: 35
<212> TYPE: PRT
<213> ORGANISM: Stichodactyla helianthus

<400> SEQUENCE: 177

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 178
<211> LENGTH: 37
<212> TYPE: PRT
```

```
<213> ORGANISM: Artificial Sequence
<220> FEATURE:
<223> OTHER INFORMATION: Modified SEQ ID NO 177 (ShK-186)
<220> FEATURE:
<221> NAME/KEY: MISC_FEATURE
<222> LOCATION: (1)..(1)
<223> OTHER INFORMATION: Xaa is phosphotyrosyl
<220> FEATURE:
<221> NAME/KEY: MISC_FEATURE
<222> LOCATION: (2)..(2)
<223> OTHER INFORMATION: Xaa is 8-amino-3,6-dioxaoctanoyl

<400> SEQUENCE: 178

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
                20                  25                  30

Thr Cys Gly Thr Cys
            35

<210> SEQ ID NO 179
<211> LENGTH: 34
<212> TYPE: PRT
<213> ORGANISM: Artificial Sequence
<220> FEATURE:
<223> OTHER INFORMATION: Mokatoxin1 (Moka1)

<400> SEQUENCE: 179

Ile Asn Val Lys Cys Ser Leu Pro Gln Gln Cys Ile Lys Pro Cys Lys
1               5                   10                  15

Asp Ala Gly Met Arg Phe Gly Lys Cys Met Asn Lys Lys Cys Arg Cys
                20                  25                  30

Tyr Ser

<210> SEQ ID NO 180
<211> LENGTH: 36
<212> TYPE: PRT
<213> ORGANISM: Unknown
<220> FEATURE:
<223> OTHER INFORMATION: Vaejovis mexicanus toxin (Vm24)

<400> SEQUENCE: 180

Ala Ala Ala Ile Ser Cys Val Gly Ser Pro Glu Cys Pro Pro Lys Cys
1               5                   10                  15

Arg Ala Gln Gly Cys Lys Asn Gly Lys Cys Met Asn Arg Lys Cys Lys
                20                  25                  30

Cys Tyr Tyr Cys
            35
```

KV1.3 BLOCKERS

CROSS-REFERENCE TO RELATED APPLICATIONS

This application is a Continuation of International Application No. PCT/EP2020/076187, filed Sep. 18, 2020, which claims priority to European Application No. 19198763.5, filed Sep. 20, 2019 and European Application No. 20172989.4, filed May 5, 2020.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "56632A_Seqlisting.txt", which was created on Jun. 23, 2021 and is 88,627 bytes in size. The subject matter of the Sequence Listing is incorporated herein in its entirety by reference.

FIELD OF THE INVENTION

The present invention provides novel blockers of the potassium channel Kv1.3, polynucleotides encoding them, and methods of making and using them.

BACKGROUND OF THE INVENTION

Ion channels are membrane proteins which form pores in biological membranes, permitting (and regulating) the flow of ions across the relevant membrane. There are numerous different types of ion channel, which may be classified in various ways, such as by the species of ions to which they provide passage, the way in which passage of ions is regulated or "gated" (e.g. "ligand-gated" or "voltage-gated"), and their cellular or sub-cellular localisation.

Potassium channels fall into four major classes, namely voltage-gated potassium channels, calcium-activated potassium channels, inwardly rectifying potassium channels, and tandem pore domain potassium channels.

The voltage-gated potassium channels, like other voltage gated channels, open or close in response to transmembrane voltages. They represent a complex family with diverse biological functions, including the regulation of neurotransmitter release, heart rate, insulin secretion, neuronal excitability, epithelial electrolyte transport, smooth muscle contraction, and cell volume.

The Kv1.3 (potassium voltage-gated channel subfamily A member 3) channel is expressed on T cells and plays a role in regulating T cell activation. Blockers of Kv1.3 have been shown to inhibit proliferation of activated T cells in vitro (reviewed in Cahalan and Chandy, Immunol. Rev. 231:59-87, 2009), and to inhibit T cell-dependent disease progression in various experimental models of autoimmune disease including experimental autoimmune encephalomyelitis (EAE), experimental arthritis, delayed-type hypersensitivity (DTH), allergic contact dermatitis and glomerulonephritis. See, for example, Rangaraju et al. (Expert Opin. Ther. Targets 13:909-24, 2009); Beeton et al. (Proc. Natl. Acad. Sci. USA. 103:17414-9, 2006); Koo et al. (J. Immunol. 158:5120-8, 1997); Hyodo et al. (Am. J. Physiol. Renal Physiol. 299: F1258-69, 2010). WO 2016/112208 describes topical application of Kv1.3 blockers for the treatment of skin and mucosal inflammation.

Thus, Kv1.3 blockers have considerable potential for use in treatment of inflammatory disorders, including autoimmune disorders.

WO 2015/013330 proposes use of Kv1.3 blocker peptides for treatment of ophthalmic conditions, such as dry eye and uveitis, including when caused by autoimmune conditions such as Sjogren's syndrome.

Blockers of Kv1.3 may also have beneficial metabolic effects, e.g. in relation to energy homeostasis, body weight regulation, and glucose control. Kv1.3 knock-out (Kv1.3 (−/−)) mice exhibit reduced weight gain, higher insulin sensitivity, and reduced plasma glucose levels in response to a high fat diet as compared to control littermates (Xu et al., Hum. Mol. Genet. 12:551-9, 2003). Further, Kv1.3 blockers have been shown to increase expression in skeletal muscle and adipose tissue of glucose transporter 4 (GLUT4), to increase insulin sensitivity in normal and ob/ob obese mice, and to increase glucose uptake in primary adipocytes in vitro (Xu et al., Proc. Natl. Acad. Sci. USA 101:3112-7, 2004). In humans, a single nucleotide polymorphism (SNP) in the Kv1.3 gene has also been associated with decreased insulin sensitivity and impaired glucose tolerance (Tschritter, Clin Endocrinol Metab 91: 654-8, 2006).

Kv1.3 is also expressed in proliferating human and mouse smooth muscle cells. Blockers of Kv1.3 may be effective in smooth muscle proliferative disorders such as restenosis, e.g. in patients following vascular surgery (e.g. angioplasty). Kv1.3 blockers have been shown to inhibit calcium entry, reduce smooth muscle cell migration, and inhibit neointimal hyperplasia in ex vivo human vein samples (Cheong et al., Cardiovasc. Res. 89:282-9, 2011).

Further evidence suggests that Kv1.3 channels are involved in the activation and/or proliferation of many types of cells, including tumor cells (Bielanska et al., Curr. Cancer Drug Targets 9:904-14, 2009), microglia (Khanna et al., Am. J. Physiol. Cell Physiol. 280: C796-806, 2001) and differentiation of neuronal progenitor cells (Wang et al., J. Neurosci. 30:5020-7, 2010). Kv1.3 blockers may therefore be beneficial in the treatment of neuroinflammatory and neurodegenerative disorders, and cancers.

Kv1.3 is part of a sub-family of closely related potassium channels, designated Kv1.1 to Kv1.8. When dealing with large homologous families, it is always desirable for a blocker to be as selective and specific as possible for the desired target, to improve efficacy and safety, and avoid undesirable off-target effects. The most specific Kv1.3 blockers identified to date are venom peptides derived from various types of venomous organisms, such as snakes, arachnids (such as scorpions and spiders), sea anemones, etc. Such Kv1.3 blockers include the peptides ShK, OskI, margatoxin and kaliotoxin, reviewed by Chandy et al., Trends in Pharmacol. Sci. 25:280-9, 2004. See also Abdel-Mottaleb et al., Toxicon 51:1424-30, 2008, and Mouhat et al., Biochem. J. 385(Pt 1):95-104, 2005.

Various attempts to engineer toxin peptides for particular properties, including specificity or potency, have been described, e.g. in WO2006/002850, WO2006/042151, WO2008/088422, WO2006/116156, WO2010/105184 and WO2014/116937.

However, there remains a need for alternative Kv1.3 blockers. Blockers having improved specificity compared to known blockers may be particularly desirable, although improvements in other properties such as stability and potency may also be useful.

SUMMARY OF THE INVENTION

The invention relates to ion channel blockers from the scorpion Parabuthus transvaalicus, having the amino acid sequences:

(PaT1)

(SEQ ID NO. 1)
QMDMRCSASVECKQKCLKAIGSIFGKCMNKKCKCYPR;

and (PaT2)

(SEQ ID NO. 2)
QMDMRCSASVECKQKCLKAIGRGFGKCMNKKCKCYPR;

and variants thereof.

Amongst other desirable properties, these molecules have been found to be extremely selective blockers for Kv1.3 over other voltage-gated potassium channels, and typically also have high potency at the Kv1.3 channel.

The invention therefore provides an ion-channel blocker comprising a Kv1.3 inhibitor component, said Kv1.3 inhibitor component comprising:

the sequence of PaT1:

(SEQ ID NO. 1)
QMDMRCSASVECKQKCLKAIGSIFGKCMNKKCKCYPR;

or a variant thereof which differs from PaT1 by up to 9 substitutions, insertions or deletions, wherein any substitutions or deletions are at amino acid positions selected from positions 1-5, 7-11, 13-15, 17-23, 25, 28-31, 33 and 35-37; and wherein said Kv1.3 inhibitor component has Kv1.3 inhibitor activity and is selective for Kv1.3;

or a pharmaceutically acceptable salt thereof.

Thus, the Kv1.3 inhibitor component of the ion channel blocker can contain up to 9 amino acid changes compared to the sequence of PaT1. Except where otherwise specified, each those 9 changes can independently be selected from a single amino acid insertion, deletion or substitution. In an embodiment, the Kv1.3 inhibitor component of the ion channel blocker may contain 9, 8, 7, 6, 5, 4, 3, 2 or 1 amino acid changes compared to the sequence of PaT1. In an embodiment, the Kv1.3 inhibitor component of the ion channel blocker contains 6 amino acid changes compared to the sequence of PaT1.

The amino acid residues of PaT1 are numbered from 1 to 33, in the conventional direction of N- to C-terminus. Throughout this specification, amino acid positions in variants of PaT1 are numbered according to the corresponding position in PaT1 when optimally aligned therewith. Thus, especially for inhibitors which contain one or more insertions or deletions compared to PaT1, the numbering of any given residue reflects the corresponding residue in PaT1 and does not necessarily reflect its linear position in the relevant sequence.

The residue present at a specific position may be indicated by the number of the relevant position alongside the single letter code or three letter code for the residue present. Thus, 1Q or Q1 (the two formats are interchangeable) indicates a glutamine (Q) residue at position 1, while 2Nle, 2[Nle], Nle2 or [Nle]2 indicates a norleucine residue at position 2.

An asterisk may be used to denote the position of a deletion relative to the sequence of PaT1. For example, "1*" indicates a deletion of the residue at position 1 as compared to PaT1.

An insertion may be indicated by a string of consecutive residues at a single position, e.g. "1QA" indicates an insertion of an alanine (A) residue after the glutamine (Q) residue at position 1.

In some embodiments, it may be desirable that one or more of positions 28, 31, 34, 35, 36 or 37 are identical to the corresponding position in PaT1, i.e. the residue present in the relevant position(s) is identical to the residue present in PaT1 at the corresponding position. For example, one or more of positions 28, 31, 34 and 35 may be identical to the corresponding position in PaT1. In some embodiments, all of positions 28, 31, 34 and 35 are identical to the corresponding positions in PaT1, e.g. all of positions 28, 31, 34, 35, 36 and 37 are identical to the corresponding positions in PaT1.

It may be desirable that any substitutions compared to PaT1 are conservative substitutions. However, any substitution listed in any of the generic formulae provided below may be introduced at the respective position.

The Kv1.3 inhibitor component of the molecule may comprise the sequence of PaT1:

(SEQ ID NO. 1)
QMDMRCSASVECKQKCLKAIGSIFGKCMNKKCKCYPR or may differ from PaT1 by up to 9 substitutions, insertions or deletions, wherein any substitutions or deletions are made only at the following positions wherein, if different from PaT1:

the residue at position 1 is selected from N, P, I, V, H, Y and S or is deleted;

the residue at position 2 is selected from Nle, I, V, L, T, Q and E or is deleted;

the residue at position 3 is selected from E, S and N or is deleted;

the residue at position 4 is selected from Nle, I, V, L, A, E and S or is deleted;

the residue at position 5 is selected from K, Q, A, L, E and D or is deleted;

the residue at position 7 is selected from K, R, Q, E, F and A;

the residue at position 8 is selected from I, H, S, L, Y and G;

the residue at position 9 is selected from A, Abu, P, F, V and L;

the residue at position 10 is selected from R, K, P, A, Q and L;

the residue at position 11 is selected from Q and D;

the residue at position 13 is selected from L, A, E, Q, I, K, H, D, V and G;

the residue at position 14 is selected from V, K, E, L, D and 2-amino-5-carboxypentanoyl;

the residue at position 15 is selected from S, L and P;

the residue at position 17 is selected from K, Y, R, Q, D, V and E or is deleted;

the residue at position 18 is selected from D, A, Y, G, V, Q, hQ and L or is deleted;

the residue at position 19 is selected from R, Y and Q or is deleted;

the residue at position 20 is selected from Y, E and R or is deleted;

the residue at position 21 is selected from R, H, E and D;

the residue at position 22 is selected from R, M, D, L and C;

the residue at position 23 is selected from R, K, hK, P, G and H;

the residue at position 26 is homo-lysine;

the residue at position 28 is selected from Nle, A and L;

the residue at position 29 is V;

the residue at position 30 is selected from G and D;

the residue at position 31 is selected from D, Q, E and H;

the residue at position 33 is selected from H, V, D, Q and R;

the residue at position 35 is selected from T, F(4-NH$_2$), F(4-F), F(4-NO$_2$) and F(4-CH$_3$);

the residue at position 36 is selected from Q, S and G or is deleted;

the residue at position 37 is selected from K, E, S and C or is deleted.

The Kv1.3 inhibitor component of the molecule may comprise the sequence of PaT1:

(SEQ ID NO. 1)
QMDMRCSASVECKQKCLKAIGSIFGKCMNKKCKCYPR or may differ from PaT1 by up to 9 substitutions, insertions or deletions, wherein any substitutions or deletions are made only at the following positions wherein, if different from PaT1:

the residue at position 1 is selected from N, P, I, V, H, Y and S or is deleted;

the residue at position 2 is selected from Nle, I, V, L, T, Q and E or is deleted;

the residue at position 3 is selected from E, S and N or is deleted;

the residue at position 4 is selected from Nle, I, V, L, A, E and S or is deleted;

the residue at position 5 is selected from K, Q, A, L, E and D or is deleted;

the residue at position 7 is selected from K, R, Q and A;

the residue at position 8 is selected from I, H and G;

the residue at position 9 is selected from A, Abu and L;

the residue at position 10 is selected from R, K, P, A and L;

the residue at position 11 is selected from Q and D;

the residue at position 13 is selected from L, A, E, Q, I, K, H, D, V and G;

the residue at position 14 is selected from V, K, E, L, D and 2-amino-5-carboxypentanoyl;

the residue at position 15 is selected from S, L and P;

the residue at position 17 is selected from K, Y, R, Q, D, V and E or is deleted;

the residue at position 18 is selected from D, A, Y, G, V, Q, hQ and L or is deleted;

the residue at position 19 is selected from R, Y and Q or is deleted;

the residue at position 20 is selected from Y, E and R or is deleted;

the residue at position 21 is selected from R, H, E and D;

the residue at position 22 is selected from R, M, D, L and C;

the residue at position 23 is selected from R, K, hK, P, G and H;

the residue at position 28 is selected from Nle, A and L;

the residue at position 29 is V;

the residue at position 30 is selected from G and D;

the residue at position 31 is selected from D, Q, E and H;

the residue at position 33 is selected from H, V, D, Q and R;

the residue at position 35 is selected from T, F(4-NH$_2$), F(4-F), F(4-NO$_2$) and F(4-CH$_3$);

the residue at position 36 is selected from Q, S and G or is deleted;

the residue at position 37 is selected from K, E, S and C or is deleted.

In some embodiments, the Kv1.3 inhibitor component may differ from PaT1 by up to 9 substitutions, insertions or deletions, wherein any substitutions or deletions are made only at the following positions wherein, if different from PaT1:

the residue at position 1 is selected from N, P, I, V, H, Y and S or is deleted;

the residue at position 2 is selected from Nle, I, V, L, T, Q and E or is deleted;

the residue at position 3 is selected from E, S and N or is deleted;

the residue at position 4 is selected from Nle, I, V, L, A, E and S or is deleted;

the residue at position 5 is selected from K, Q, A and L or is deleted;

the residue at position 7 is selected from K, R and Q;

the residue at position 8 is selected from I, H, S, L, Y and G;

the residue at position 9 is selected from A, Abu, P, F, V and L;

the residue at position 10 is selected from R, K and P;

the residue at position 11 is Q;

the residue at position 13 is selected from L, A, E, Q, I, K, H and G;

the residue at position 14 is selected from V, K, E, L and 2-amino-5-carboxypentanoyl;

the residue at position 15 is selected from S and L;

the residue at position 17 is selected from K, Y, R, Q and D or is deleted;

the residue at position 18 is selected from D, A, Y, G, V, Q, hQ and L or is deleted;

the residue at position 19 is selected from R, Y and Q or is deleted;

the residue at position 20 is selected from Y, E and R or is deleted;

the residue at position 21 is selected from R, H and E;

the residue at position 22 is selected from R, M, D, L and C;

the residue at position 23 is selected from R, K, hK, P and G;

the residue at position 28 is Nle;

the residue at position 30 is selected from G and D;

the residue at position 31 is selected from D, Q, E and H;

the residue at position 33 is selected from H, V, D, Q and R;

the residue at position 35 is selected from T, F(4-NH$_2$), F(4-F), F(4-NO$_2$) and F(4-CH$_3$);

the residue at position 36 is selected from Q, S and G or is deleted;

the residue at position 37 is selected from K, S and C or is deleted.

In some embodiments, the Kv1.3 inhibitor component may differ from PaT1 by up to 9 substitutions, insertions or deletions, wherein any substitutions or deletions are made only at the following positions wherein, if different from PaT1:

the residue at position 1 is selected from N, P, I, V, H, Y and S or is deleted;

the residue at position 2 is selected from Nle, I, V, L, T, Q and E or is deleted;

the residue at position 3 is selected from E, S and N or is deleted;

the residue at position 4 is selected from Nle, I, V, L, A, E and S or is deleted;

the residue at position 5 is selected from K, Q, A and L or is deleted;

the residue at position 7 is selected from K, R and Q;

the residue at position 8 is selected from I, H and G;

the residue at position 9 is selected from A, Abu and L;

the residue at position 10 is selected from R, K and P;
the residue at position 11 is Q;
the residue at position 13 is selected from L, A, E, Q, I, K, H and G;
the residue at position 14 is selected from V, K, E, L and 2-amino-5-carboxypentanoyl;
the residue at position 15 is selected from S and L;
the residue at position 17 is selected from K, Y, R, Q and D or is deleted;
the residue at position 18 is selected from D, A, Y, G, V, Q, hQ and L or is deleted;
the residue at position 19 is selected from R, Y and Q or is deleted;
the residue at position 20 is selected from Y, E and R or is deleted;
the residue at position 21 is selected from R, H and E;
the residue at position 22 is selected from R, M, D, L and C;
the residue at position 23 is selected from R, K, hK, P and G;
the residue at position 28 is Nle;
the residue at position 30 is selected from G and D;
the residue at position 31 is selected from D, Q, E and H;
the residue at position 33 is selected from H, V, D, Q and R;
the residue at position 35 is selected from T, F(4-NH$_2$), F(4-F), F(4-NO$_2$) and F(4-CH$_3$);
the residue at position 36 is selected from Q, S and G or is deleted;
the residue at position 37 is selected from K, S and C or is deleted.

The Kv1.3 inhibitor component of the molecule may comprise the sequence of PaT1:

(SEQ ID NO. 1)
QMDMRCSASVECKQKCLKAIGSIFGKCMNKKCKCYPR or may differ from PaT1 by up to 9 substitutions, insertions or deletions, wherein any substitutions or deletions are made only at the following positions wherein, if different from PaT1:
the residue at position 1 is selected from N, P, V, H, Y and S or is deleted;
the residue at position 2 is selected from Nle, I, V and L or is deleted;
the residue at position 3 is selected from E and S or is deleted;
the residue at position 4 is selected from Nle, I, V, L, E and S or is deleted;
the residue at position 5 is K or is deleted;
the residue at position 7 is selected from K and R;
the residue at position 8 is selected from I and H;
the residue at position 9 is selected from Abu and L;
the residue at position 10 is selected from R and K;
the residue at position 11 is Q;
the residue at position 13 is selected from L, A, E, Q, V and G;
the residue at position 14 is selected from V, K, E, L and 2-amino-5-carboxypentanoyl;
the residue at position 15 is selected from S and L;
the residue at position 17 is selected from K, Y and R or is deleted;
the residue at position 18 is selected from D, A, Y, G, V, Q, hQ and L or is deleted;
the residue at position 19 is selected from R and Y or is deleted;
the residue at position 20 is selected from Y, E and R or is deleted;
the residue at position 21 is selected from R, H and E;
the residue at position 22 is selected from R and C;
the residue at position 23 is selected from R, K, hK, P and G;
the residue at position 28 is Nle;
the residue at position 30 is G;
the residue at position 33 is selected from H, V and R;
the residue at position 35 is selected from F(4-NH$_2$), F(4-F), F(4-NO$_2$) and F(4-CH$_3$);
the residue at position 36 is selected from Q, S and G or is deleted;
the residue at position 37 is selected from S and C or is deleted.

In some embodiments, the Kv1.3 inhibitor component of the molecule comprises the sequence of PaT1:

(SEQ ID NO. 1)
QMDMRCSASVECKQKCLKAIGSIFGKCMNKKCKCYPR or differs from PaT1 by up to 9 substitutions, insertions or deletions, wherein any substitutions or deletions are made only at the following positions wherein, if different from PaT1:
the residue at position 1 is selected from N and P or is deleted;
the residue at position 2 is Nle, I, V and L;
the residue at position 3 is selected from E and S;
the residue at position 4 is Nle, I, V and L;
the residue at position 8 is I;
the residue at position 10 is R;
the residue at position 11 is Q;
the residue at position 13 is A;
the residue at position 14 is V;
the residue at position 18 is selected from D, Y and A;
the residue at position 19 is R;
the residue at position 20 is Y;
the residue at position 21 is R;
the residue at position 22 is selected from R and C;
the residue at position 23 is selected from R and G;
the residue at position 28 is Nle;
the residue at position 30 is G;
the residue at position 33 is H;
the residue at position 37 is C.

In some embodiments the invention provides an ion-channel blocker comprising a Kv1.3 inhibitor component, said Kv1.3 inhibitor component comprising: the sequence of PaT1:

(SEQ ID NO. 1)
QMDMRCSASVECKQKCLKAIGSIFGKCMNKKCKCYPR;

or a sequence which has at least 75% identity with the sequence of PaT1, wherein any differences from the sequence of PaT1 are at amino acid positions selected from positions 1-5, 7-11, 13-15, 17-23, 25, 28-31, 33 and 35-37; and
wherein said Kv1.3 inhibitor component has Kv1.3 inhibitor activity and is selective for Kv1.3;
or a pharmaceutically acceptable salt thereof.

In some embodiments the Kv1.3 inhibitor component has at least 75% identity with the sequence of PaT1. In some embodiments the Kv1.3 inhibitor component has at least 80% identity with the sequence of PaT1. In some embodiments the Kv1.3 inhibitor component has at least 85% identity with the sequence of PaT1. In some embodiments the Kv1.3 inhibitor component has at least 90% identity with the sequence of PaT1. In some embodiments the Kv1.3 inhibitor component has at least 95% identity with the sequence of PaT1. In some embodiments the Kv1.3 inhibitor component has at least 97% identity with the sequence of PaT1.

The Kv1.3 inhibitor component may comprise one or more insertions or deletions as compared to the sequence of PaT1.

Typically, the Kv1.3 inhibitor component comprises a maximum of three insertions as compared to the sequence of PaT1, e.g. precisely 3 insertions, precisely 2 insertions, or precisely 1 insertion.

Typically, only a single amino acid is inserted at any given site, although insertions of multiple amino acids may be tolerated. For the avoidance of doubt, an insertion of two amino acids at the same site is considered as two insertions and hence as two of the permitted differences from the sequence of PaT1.

Typically, the Kv1.3 inhibitor component contains no more than 7 deletions compared to the sequence of PaT1, e.g. no more than 6, no more than 5, no more than 5, no more than 4, no more than 3, no more than 2 deletions, no more than one deletion, or no deletions at all.

In order to preserve the spacing of the cysteine residues, and hence the pattern of disulphide bonding, it may be desirable that any insertions and deletions are not located between the cysteine residue at position 6 (6C) and the cysteine residue at position 34 (34C). Thus, any insertion or deletion may preferably be located N-terminal of 6C or C-terminal of 34C.

However, if the Kv1.3 inhibitor component contains one or more insertions or deletions between 6C and 34C, then it may be desirable to incorporate the same number of both insertions and deletions within that region. e.g. to restore the relative spacing of the cysteine residues.

In many embodiments the Kv1.3 inhibitor component has no insertions as compared to the sequence of PaT1.

If a deletion is present between 6C and 34C, it may be desirable that only one such deletion is present. It may, for example, be at position 17, 18, 19 or 20, especially if the molecule does not contain a corresponding insertion to maintain the spacing of the cysteine residues.

Without wishing to be bound by theory, it is believed that multiple deletions may be better tolerated in the N-terminal sequence (residues 1-5) and C-terminal sequence (residues 36-37). Multiple deletions may be tolerated in these regions. For deletions in the N-terminal sequence (positions 1-5), if a residue at position X is deleted, it may be desirable that all residues N-terminal of that residue are also deleted. Thus, for example, residues 1, 1 and 2, 1 to 3, 1 to 4 or 1 to 5 may be deleted. For deletions at the C-terminus (positions 36-37), if the residue at position 36 is deleted, it may be desirable that the residue at position 37 is also deleted. Thus, for example, residues 37, or 36 and 37, may be deleted.

For the avoidance of doubt, a deletion of two consecutive amino acids is considered as two amino acid deletions and hence as two of the permitted differences from the sequence of PaT1.

Glutamine (Q) residues can be unstable, either in vivo or in vitro, e.g. during storage in aqueous solution. This may be of particular relevance when the glutamine residue is located at the N-terminus of the molecule, as the side chain is sterically capable of interacting with the free alpha amino group, resulting in dehydration to pyroglutamate. Thus it may be desirable that the residue at position 1 is not Q, especially if the ion channel blocker does not contain any additional sequence N-terminal of the Kv1.3 inhibitor. For example, the residue at position 1 may be N or P, or may be deleted; i.e. the Kv1.3 inhibitor may comprise 1N, 1P or 1*.

Additionally or alternatively, it may be desirable that one, two or all three of the residues at positions 2, 4 and 28 are not M, since methionine (M) residues are susceptible to oxidation. Preferably one, two or all three methionine residues are either individually substituted with a residue having a non-oxidisable side chain, or are deleted. Any suitable residue with a non-oxidisable residue may be used, with Nle. I, V and L being particularly suitable.

Suitable combinations of residues at some or all of positions 2, 4 and 28 include:
2*+4Nle, 4I, 4V or 4L;
2Nle+4Nle, 4I, 4V or 4L;
2I+4Nle, 4I, 4V or 4L;
2V+4Nle, 4I, 4V or 4L;
2L+4Nle, 4I, 4V or 4L.
Any of the above may be combined with 28Nle.
2Nle+4Nle+28Nle may be particularly preferred.

In some embodiments, the Kv1.3 inhibitor component contains the residues 22S+23I or 22R+23G.

In addition to any differences at positions 1, 2, 4 and 28, it may be desirable that the Kv1.3 inhibitor component contains only 4 further differences, only 3 further differences, only 2 further differences, or only 1 further difference from the sequence of PaT1.

The Kv1.3 inhibitor component may be identical to PaT1 or PaT2 at all positions apart from positions 1, 2, 4 and 28.

Additionally or alternatively, the Kv1.3 inhibitor component may comprise the residues 13A and/or 18A.

For example, it may comprise
2Nle+13A;
2Nle+18A, or
2Nle+13A+18A.
For example, it may comprise
2Nle+4Nle+13A+28Nle;
2Nle+4Nle+18A+28Nle; or
2Nle+4Nle+13A+18A+28Nle.
Any of the above may be combined with 1*.

The Kv1.3 inhibitor component may be identical to PaT1 or PaT2 at all positions apart from positions 2, 3 and 4.

Additionally or alternatively, the Kv1.3 inhibitor component may comprise the residues 1P and/or 18A.

For example it may comprise
2Nle+4Nle+28Nle;
2Nle+3E+4Nle+28Nle;
2Nle+3E+4Nle+18A+28Nle;
1P+2Nle+4Nle+28Nle;
1P+2Nle+3E+4Nle+28Nle; or
1P+2Nle+3E+4Nle+18A+28Nle.

Additionally or alternatively, any of the above may be combined with 22C+37C, i.e. residues at positions 22 and 37 capable of forming a disulphide bond.

The ion channel blocker may comprise additional amino acid sequences N-terminal and/or C-terminal of the Kv1.3 inhibitor component. For example, the ion channel blocker may be a fusion protein comprising the Kv1.3 inhibitor and one or more heterologous peptide or polypeptide sequences, which may be referred to as heterologous components. The heterologous components may serve, for example, to facilitate recombinant expression, increase solubility or extend half life in vivo. Suitable heterologous components include human serum albumin (HSA), an antibody Fc domain, etc.

Other heterologous components include tags such as a polyhistidine tag, FLAG tag or Myc tag.

The ion channel blocker may comprise a linker peptide located between the Kv1.3 inhibitor and the heterologous component.

The various components may be in any appropriate orientation. For example, the Kv1.3 inhibitor may be located N-terminal of the heterologous component, or the heterologous component may be located N-terminal of the Kv1.3 inhibitor, with the linker (where present) between them.

A peptide linker is typically between 3 and 30 amino acids in length, with a high proportion of small and hydrophilic amino acid residues (e.g. glycine and serine) to provide the required flexibility without compromising aqueous solubility of the molecule. For example, it may comprise at least 50% glycine and serine residues, at least 60% glycine and serine residues, at least 70% glycine and serine residues, at least 80% glycine and serine residues, or at least 90% glycine and serine residues. It may also contain a protease cleavage site to enable separation of the Kv1.3 inhibitor and heterologous component.

The Kv1.3 inhibitor may also be inserted within a heterologous polypeptide, which may be regarded as a "scaffold" for the Kv1.3 inhibitor. In such cases, the ion channel blocker may be considered to comprise heterologous components N- and C-terminal of the Kv1.3 inhibitor, wherein the heterologous components are derived from the same molecule and interact with one another, e.g. to fold into a scaffold, having the Kv1.3 inhibitor displayed at its surface. Thus, the Kv1.3 inhibitor may be inserted within a surface loop of a heterologous protein, e.g. into the CDR sequence of an antibody or a fragment thereof containing the antigen binding domain. It has been demonstrated that a Kv1.3 inhibitor retains activity when inserted into a CDR (e.g. CDR3L) of a humanised immunoglobulin designated "Syn", directed against respiratory syncytial virus. (Wang et al., Proc. Natl. Acad. Sci. USA 113(41), 11501-11506, 2016.) The Syn antibody, or a fragment thereof containing the antigen binding domain, may therefore be used as a scaffold. If the antibody scaffold contains an Fc domain, it may be desirable that this is functionally "Fc-null", i.e. it is not capable of binding to the Fc receptor. Such mutations are described by Wang et al., op cit.

In some embodiments, the ion channel blocker may have a maximum length of 200 amino acids, e.g. of 150 amino acids, 125 amino acids, 100 amino acids, 75 amino acids or 50 amino acids, e.g. 49, 48, 47, 46, 45, 44, 43, 42, 41, 40, 39, 38 or 37 amino acids, or even shorter where the Kv1.3 inhibitor component contains one or more deletions compared to the sequence of PaT1.

The ion channel blocker may further comprise up to 10 additional residues at the N-terminus, e.g. 1, 2, 3, 4, 5, 6, 7, 8, 9 or 10 additional residues at the N-terminus. Additionally or alternatively, the ion channel blocker may further comprise up to 10 residues at the C-terminus, e.g. 1, 2, 3, 4, 5, 6, 7, 8, 9 or 10 additional residues at the C-terminus, within the constraint that the molecule is not more than 50 amino acids in length.

For example, the additional sequence at the N-terminus may comprise or consist of the sequence GG or SG. Additionally or alternatively, the additional sequence at the C-terminus may comprise or consist of the sequence RRTA (SEQ ID NO. 146), HRRK (SEQ ID NO. 147), QSKA (SEQ ID NO. 148), AGPR (SEQ ID NO. 149), RSRT (SEQ ID NO. 150), RHKR (SEQ ID NO. 151), GGKR (SEQ ID NO. 152), PKTA (SEQ ID NO. 153), TDAR (SEQ ID NO. 154), HRQQ (SEQ ID NO. 155), RPRH (SEQ ID NO. 156), ARNA (SEQ ID NO. 157), TGRK (SEQ ID NO. 158), HERT (SEQ ID NO. 159), NTRT (SEQ ID NO. 160), QRNG (SEQ ID NO. 161), AHRN (SEQ ID NO. 162), PRSA (SEQ ID NO. 163), QRQS (SEQ ID NO. 164), QRRK (SEQ ID NO. 165), ARAK (SEQ ID NO. 166), AKRD (SEQ ID NO. 167), RDKT (SEQ ID NO. 168), HRRK (SEQ ID NO. 169), RAKR (SEQ ID NO. 170), QRTR (SEQ ID NO. 171), ATRH (SEQ ID NO. 172), ARRS (SEQ ID NO. 173), AKTR (SEQ ID NO. 174), NRQR (SEQ ID NO. 175), PRNT (SEQ ID NO. 176), e.g. RRTA (SEQ ID NO. 146) or HRRK (SEQ ID NO. 174). All of these sequences have been shown to be compatible with Kv1.3 inhibitor activity and selectivity when added to the C-terminus of Odk2 analogues (see WO 12014/116937).

Thus the invention also provides an ion channel blocker having the formula:

$$R^1-Z^1-X-Z^2-R^2$$

where
$R^1$ is hydrogen, C1-4 alkyl, acetyl, formyl, benzoyl or trifluoroacetyl; $R^2$ is OH, $NH_2$ or $CH_2OH$,
X is a Kv1.3 inhibitor having the sequence of PaT1 or a variant thereof as described above, and
$Z^1$ and $Z^2$ are independently sequences of up to 10 amino acid residues;
with the proviso that the ion channel blocker have a maximum length of 50 amino acids;
or a pharmaceutically acceptable salt thereof.

As set out above, $Z^1$ may comprise or consist of the sequence GG or SG.

Additionally or alternatively, $Z^2$ may comprise or consist of the sequence RRTA (SEQ ID NO. 146), HRRK (SEQ ID NO. 147), QSKA (SEQ ID NO. 148), AGPR (SEQ ID NO. 149), RSRT (SEQ ID NO. 150), RHKR (SEQ ID NO. 151), GGKR (SEQ ID NO. 152), PKTA (SEQ ID NO. 153), TDAR (SEQ ID NO. 154), HRQQ (SEQ ID NO. 155), RPRH (SEQ ID NO. 156), ARNA (SEQ ID NO. 157), TGRK (SEQ ID NO. 158), HERT (SEQ ID NO. 159), NTRT (SEQ ID NO. 160), QRNG (SEQ ID NO. 161), AHRN (SEQ ID NO. 162), PRSA (SEQ ID NO. 163), QRQS (SEQ ID NO. 164), QRRK (SEQ ID NO. 165), ARAK (SEQ ID NO. 166), AKRD (SEQ ID NO. 167), RDKT (SEQ ID NO. 168), HRRK (SEQ ID NO. 169), RAKR (SEQ ID NO. 170), QRTR (SEQ ID NO. 171), ATRH (SEQ ID NO. 172), ARRS (SEQ ID NO. 173), AKTR (SEQ ID NO. 174), NRQR (SEQ ID NO. 175), PRNT (SEQ ID NO. 176), e.g. RRTA (SEQ ID NO. 146) or HRRK (SEQ ID NO. 147).

Additionally or alternatively, $R^2$ can be $CH_2OH$ and can be comprised in (4-amino-5-hydroxypentyl)guanidine or 4-amino-5-hydroxypentanamide.

The Kv1.3 inhibitor component of the molecule contains 6 cysteine (C) residues which together form three disulphide bonds, between residues 6C and 27C, residues 12C and 32C, and residues 16C and 34C. It is believed that these bonds are important for the conformation and activity of the Kv1.3 inhibitor.

The disulphide bonds may be indicated graphically as follows by reference to PaT1:

```
                                                (SEQ ID NO. 1)
QMDMR[C(1)]SASVE[C(2)]KQK[C(3)]LKAIGSIFGK[C(1)]

MNKK[C(2)]K[C(3)]YPR
``` where a pair of cysteine residues which participate together in a disulphide bond are indicated by the same numeral in parentheses. Similar notation can be applied to any of the other sequences in this application. Except where the context demands otherwise, it should be understood that an active inhibitor compound includes appropriate disulphide bonding.

It may be desirable that no other cysteine residues are introduced into the Kv1.3 inhibitor component by substitution. Additionally or alternatively, it may be desirable that no cysteine residues are present in any N- or C-terminal additional sequence. Thus, in some embodiments, the molecule contains no other cysteine residues apart from those at positions 6, 12, 16, 27, 32 and 34 of PaT1.

However, in some embodiments, the inhibitor component comprises 8 cysteine residues, which together form four disulphide bonds, between residues 6C and 27C, residues 12C and 32C, residues 16C and 34C, and cysteine residues at positions corresponding to positions 22 and 37 of Pat1. Compound 87 is an example of such a molecule, and the disulphide bonding may be indicated graphically as follows:

(SEQ ID NO. 87)
H—S[Nle]D[Nle]R[C(1)]SASVE[C(2)]KQK[C(3)]LAAIG

[C(4)]IFGK[C(1)][Nle]NKK[C(2)]K[C(3)]YP[C(4)]-NH₂

Similar notation may be applied to other compounds having four pairs of disulphide bonds.

Thus, an inhibitor typically has cysteine residues at positions 22 and 37, or neither of positions 22 and 37 is a cysteine residue (i.e. both positions 22 and 37 are not cysteine).

The Kv1.3 inhibitor component may comprise one of the following sequences:

```
                                         (SEQ ID NO. 1)
QMDMRCSASVECKQKCLKAIGSIFGKCMNKKCKCYPR (SEQ ID NO. 2)
QMDMRCSASVECKQKCLKAIGRGFGKCMNKKCKCYPR (SEQ ID NO. 3)
NMDMRCSASVECKQKCLKAIGSIFGKCMNKKCKCYPR (SEQ ID NO. 4)
NMDMRCSASVECKQKCLKAIGRGFGKCMNKKCKCYPR (SEQ ID NO. 5)
MDMRCSASVECKQKCLKAIGSIFGKCMNKKCKCYPR (SEQ ID NO. 6)
DMRCSASVECKQKCLKAIGSIFGKCMNKKCKCYPR (SEQ ID NO. 7)
NMDMRCSASVECKQKCLKAIGSIFGKCMNKKCKCYPR (SEQ ID NO. 8)
NIDMRCSASVECKQKCLKAIGSIFGKCMNKKCKCYPR (SEQ ID NO. 9)
NMDVRCSASVECKQKCLKAIGSIFGKCMNKKCKCYPR (SEQ ID NO. 10)
NMDMRCSASVECKQKCKDAIGSIFGKCMNKKCKCYPR (SEQ ID NO. 12)
NMEMRCSASVECKQKCLKAIGSIFGKCMNKKCKCYPR (SEQ ID NO. 14)
N[Nle]DMRCSASVECKQKCLKAIGSIFGKCMNKKCKCYPR

NMD[Nle]RCSASVECKQKCLKAIGSIFGKCMNKKCKCYPR

NMDMRCSASVECKQKCLKAIGSIFGKC[Nle]NKKCKCYPR
```

-continued
```
                                        (SEQ ID NO. 17)
NMDMRCSASVECKVKCLKAIGSIFGKCMNKKCKCYPR (SEQ ID NO. 18)
NMDMRCSASVECKQLCLKAIGSIFGKCMNKKCKCYPR (SEQ ID NO. 19)
NMDMRCSASVECKQKCKKAIGSIFGKCMNKKCKCYPR (SEQ ID NO. 20)
NMDMRCSASVECKQKCLDAIGSIFGKCMNKKCKCYPR (SEQ ID NO. 21)
NMDMRCSASVECKQKCLKAIRSIFGKCMNKKCKCYPR (SEQ ID NO. 22)
NMDMRCSASVECKQKCLKAIESIFGKCMNKKCKCYPR (SEQ ID NO. 25)
NMDMRCKASVECKQKCLKAIGSIFGKCMNKKCKCYPR (SEQ ID NO. 26)
NMDMRCSISVECKQKCLKAIGSIFGKCMNKKCKCYPR (SEQ ID NO. 27)
NMDMRCSASRECKQKCLKAIGSIFGKCMNKKCKCYPR (SEQ ID NO. 28)
NMDMRCSASVQCKQKCLKAIGSIFGKCMNKKCKCYPR (SEQ ID NO. 29)
NMDMRCSASVECLQKCLKAIGSIFGKCMNKKCKCYPR (SEQ ID NO. 30)
NMDMRCSASVECAQKCLKAIGSIFGKCMNKKCKCYPR (SEQ ID NO. 31)
NMDMRCSASVECKEKCLKAIGSIFGKCMNKKCKCYPR (SEQ ID NO. 32)
NMDMRCSASVECKLKCLKAIGSIFGKCMNKKCKCYPR (SEQ ID NO. 33)
NMDMRCSASVECKQKCLKAIHSIFGKCMNKKCKCYPR (SEQ ID NO. 34)
NMDMRCSASVECKQKCLKAIGSKFGKCMNKKCKCYPR (SEQ ID NO. 35)
NMDMRCSASVECKQKCLKAIGSRFGKCMNKKCKCYPR (SEQ ID NO. 36)
NMDMRCSASVECKQKCLKAIGSIFGKCMNGKCKCYPR (SEQ ID NO. 37)
NMDMRCSASVECKQKCLKAIGSIFGKCMNKKCHCYPR (SEQ ID NO. 38)
NMDMRCSASVECKQKCLKAIGSIFGKCMNKKCVCYPR (SEQ ID NO. 39)
N[Nle]D[Nle]RCSASVECKQKCLKAIGSIFGKCMNKKCKCYPR (SEQ ID NO. 40)
N[Nle]D[Nle]RCSASVECKQKCLKAIGSIFGKC[Nle]NKKCKCYPR (SEQ ID NO. 41)
P[Nle]D[Nle]RCSASVECKQKCLKAIGSIFGKC[Nle]NKKCKCYPR (SEQ ID NO. 42)
N[Nle]D[Nle]RCRASVECKQKCLKAIGSIFGKC[Nle]NKKCKCYPR (SEQ ID NO. 43)
N[Nle]D[Nle]RCSASVECEQKCLKAIGSIFGKC[Nle]NKKCKCYPR (SEQ ID NO. 44)
N[Nle]D[Nle]RCSASVECQQKCLKAIGSIFGKC[Nle]NKKCKCYPR (SEQ ID NO. 45)
N[Nle]D[Nle]RCSASVECKKKCLKAIGSIFGKC[Nle]NKKCKCYPR
```

-continued (SEQ ID NO. 46)
N[Nle]S[Nle]RCSASVECKQKCLKAIGSIFGKC[Nle]NKKCKCYPR (SEQ ID NO. 47)
N[Nle]D[Nle]RCSHSVECKQKCLKAIGSIFGKC[Nle]NKKCKCYPR (SEQ ID NO. 48)
N[Nle]D[Nle]RCSASVECKQSCLKAIGSIFGKC[Nle]NKKCKCYPR (SEQ ID NO. 49)
N[Nle]D[Nle]RCSASVECKQKCKAIGSIFGKC[Nle]NKKCKCYPR (SEQ ID NO. 50)
NMDMRCSASVECKQKCYKAIGSIFGKCMNKKCKCYPR (SEQ ID NO. 51)
NMDMRCSASVECKQKCRKAIGSIFGKCMNKKCKCYPR (SEQ ID NO. 52)
NMDMRCSASVECKQKCLAAIGSIFGKCMNKKCKCYPR (SEQ ID NO. 53)
NMDMRCSASVECKQKCLYAIGSIFGKCMNKKCKCYPR (SEQ ID NO. 54)
NMDMRCSASVECKQKCLAIGSIFGKCMNKKCKCYPR (SEQ ID NO. 55)
NMDMRCSASVECKQKCLKYIGSIFGKCMNKKCKCYPR (SEQ ID NO. 56)
NMDMRCSASVECKQKCLKRIGSIFGKCMNKKCKCYPR (SEQ ID NO. 57)
NMDMRCSASVECKQKCLKIGSIFGKCMNKKCKCYPR (SEQ ID NO. 58)
NMDMRCSASVECKQKCLKAYGSIFGKCMNKKCKCYPR (SEQ ID NO. 59)
NMDMRCSASVECKQKCLKAEGSIFGKCMNKKCKCYPR (SEQ ID NO. 60)
NMDMRCSASVECKQKCLKARGSIFGKCMNKKCKCYPR (SEQ ID NO. 61)
NMDMRCSASVECKQKCLKAGSIFGKCMNKKCKCYPR (SEQ ID NO. 62)
N[Nle]D[Nle]RCSASVECKQKCLKAIGSPFGKC[Nle]NKKCKCYPR (SEQ ID NO. 63)
N[Nle]D[Nle]RCSASKECKQKCLKAIGSIFGKC[Nle]NKKCKCYPR (SEQ ID NO. 64)
H[Nle]D[Nle]RCSASVECKQKCLKAIGSIFGKC[Nle]NKKCKCYPR (SEQ ID NO. 65)
Y[Nle]D[Nle]RCSASVECKQKCLKAIGSIFGKC[Nle]NKKCKCYPR (SEQ ID NO. 66)
S[Nle]D[Nle]RCSASVECKQKCLKAIGSIFGKC[Nle]NKKCKCYPR (SEQ ID NO. 67)
V[Nle]D[Nle]RCSASVECKQKCLKAIGSIFGKC[Nle]NKKCKCYPR (SEQ ID NO. 68)
S[Nle]D[Nle]RCSA[Abu]VECKQKCLKAIGSIFGKCMNKKCKCYPR (SEQ ID NO. 69)
S[Nle]D[Nle]RCSASVECKQKCLKAIGSIFG[homo-Lys]CMNKKCKCYPR (SEQ ID NO. 70)
S[Nle]D[Nle]RCSASVECKQKCLKAIGSIFGKCMNKKCKC[F(4-NH$_2$)]PR (SEQ ID NO. 71)
S[Nle]D[Nle]RCSASVECGQKCLKAIGSIFGKCMNKKCKCYPR (SEQ ID NO. 72)
S[Nle]D[Nle]RCSASVECVQKCLKAIGSIFGKCMNKKCKCYPR (SEQ ID NO. 73)
S[Nle]D[Nle]RCSASVECK[2-Amino-5-carboxypentanoyl]KCLKAIGSIFGKCMNKKCKCYPR (SEQ ID NO. 74)
S[Nle]D[Nle]RCSASVECKQKCLKAIGSIFGKCMNKKCKCYQ (SEQ ID NO. 75)
S[Nle]D[Nle]RCSASVECKQKCLKAIGSIFGKCMNKKCRCYPR (SEQ ID NO. 76)
S[Nle]DERCSASVECKQKCLKAIGSIFGKCMNKKCKCYPR (SEQ ID NO. 77)
S[Nle]D[Nle]RCSASVECKQKCLGAIGSIFGKCMNKKCKCYPR (SEQ ID NO. 78)
S[Nle]D[Nle]RCSASVECKQKCLVAIGSIFGKCMNKKCKCYPR (SEQ ID NO. 79)
S[Nle]D[Nle]RCSASVECAQSCLKAIGSIFGKCMNKKCKCYPR (SEQ ID NO. 80)
S[Nle]D[Nle]RCSASVECAQKCLAAIGSIFGKCMNKKCKCYPR (SEQ ID NO. 81)
S[Nle]D[Nle]RCSASVECAQLCLAAIGSIFGKCMNKKCKCYPR (SEQ ID NO. 82)
S[Nle]D[Nle]RCSASVECKQKCLKAIGSIFGKC[Nle]NKKCKCYPR (SEQ ID NO. 83)
P[Nle]D[Nle]RCSASVECKQKCLKAIGCIFGKC[Nle]NKKCKCYPC (SEQ ID NO. 84)
S[Nle]D[Nle]RCSASVECKEKCLQAIGSIFGKC[Nle]NKKCKCYPR (SEQ ID NO. 85)
P[Nle]D[Nle]RCSASVECKEKCL[homo-Gln]AlGSIFGKC[Nle]NKKCKCYPR (SEQ ID NO. 86)
CSASVECKQKCLKAIGCIFGKC[Nle]NKKCKCYPC (SEQ ID NO. 87)
S[Nle]D[Nle]RCSASVECKQKCLAAIGCIFGKC[Nle]NKKCKCYPC (SEQ ID NO. 88)
P[Nle]D[Nle]RCSASVECKQKCLKAIGCIFGKC[Nle]NKKCKCYPC (SEQ ID NO. 89)
S[Nle]D[Nle]RCSALVECKQKCLKAIGSIFGKCMNKKCKCYPR (SEQ ID NO. 90)
S[Nle]D[Nle]RCSAVVECKQKCLKAIGSIFGKCMNKKCKC(3)YPR (SEQ ID NO. 91)
S[Nle]D[Nle]RCSASVECKQKCLKAIGSIFGKCMNKKCKC[F(4-F)]PR (SEQ ID NO. 92)
S[Nle]D[Nle]RCSASVECKQKCLKAIGSIFGKCMNKKCKC[F(4-NO$_2$)]PR (SEQ ID NO. 93)
S[Nle]D[Nle]RCSASVECKQKCLKAIGSIFGKCMNKKCKC[F(4-CH$_3$)]PR -continued (SEQ ID NO. 94)
[Nle]D[Nle]RCSASVECKQKCLKAIGSIFGKC[Nle]NKKCKCYPR (SEQ ID NO. 95)
NID[Nle]RCSASVECKQKCLKAIGSIFGKC[Nle]NKKCKCYPR (SEQ ID NO. 96)
PIE[Nle]RCSASVECKQKCLKAIGSIFGKC[Nle]NKKCKCYPR (SEQ ID NO. 97)
P[Nle]E[Nle]RCSASVECKQKCLAAIGSIFGKC[Nle]NKKCKCYPR (SEQ ID NO. 98)
P[Nle]E[Nle]RCSASVECKQKCLAAIGSIFGKC[Nle]NKKCKCYPR (SEQ ID NO. 99)
P[Nle]E[Nle]RCSASVECKQKCLLAIGSIFGKC[Nle]NKKCKCYPR (SEQ ID NO. 100)
PIDERCSASVECKQKCLAAIGSIFGKC[Nle]NKKCKCYPR (SEQ ID NO. 101)
PIE[Nle]RCSASVECKQKCLAAIGSIFGKC[Nle]NKKCKCYPR (SEQ ID NO. 102)
P[Nle]D[Nle]RCSASVECAQKCLAAIGSIFGKCMNKKCKCYPR (SEQ ID NO. 103)
P[Nle]E[Nle]RCSASVECAQKCLAAIGSIFGKC[Nle]NKKCKCYPR (SEQ ID NO. 104)
CSASVECKQKCLKAIGSIFGKC[Nle]NKKCKCYPR (SEQ ID NO. 105)
CSASVECKQKCLKAIGSIFGKC[Nle]NKKCKCYPR (SEQ ID NO. 106)
RCSASVECKQKCLKAIGSIFGKC[Nle]NKKCKCYPR (SEQ ID NO. 107)
SKCSASVECKQKCLKAIGSIFGKC[Nle]NKKCKCYPR (SEQ ID NO. 108)
LRCSASVECKQKCLKAIGSIFGKC[Nle]NKKCKCYPR (SEQ ID NO. 109)
CSASVECKQKCLKAIGSIFGKC[Nle]NKKCKCYPS (SEQ ID NO. 110)
CSASVECKQKCLKAIGSIFGKC[Nle]NKKCKCYS (SEQ ID NO. 111)
CSASVECKQKCLKAIGSIFGKC[Nle]NKKCKCYG-NH2

(SEQ ID NO. 112)
CSASVECKQKCLKAIGSIFGKC[Nle]NKKCKCY-NH2

(SEQ ID NO. 113)
RCSASVECKQKCLKAIGSIFGKC[Nle]NKKCKCYPR (SEQ ID NO. 114)
LRCSASVECKQKCLKAIGSIFGKC[Nle]NKKCKCYPR (SEQ ID NO. 115)
LRCSASVECKQKCLAAIGSIFGKC[Nle]NKKCKCYPR (SEQ ID NO. 116)
LRCSASVECKQKCLAAIGSIFGKCMNKKCKCYPR (SEQ ID NO. 117)
CSASVECKQKCLKAIGSIFGKCMNKKCKCYPR (SEQ ID NO. 118)
P[Nle]E[Nle]RCSASVECKEKCLAAIGSIFGKC[Nle]NKKCKCYPR (SEQ ID NO. 119)
p[Nle]E[Nle]RCSASVECKQKCLAAIGSIFGKC[Nle]NKKCKCYPR (SEQ ID NO. 120)
P[Nle]E[Nle]RCSASVECKQKCLAAIGSIFGKC[Nle]NKKCKCYR (SEQ ID NO. 121)
[Nle]E[Nle]RCSASVECKQKCLAAIGSIFGKC[Nle]NKKCKCYPR (SEQ ID NO. 122)
P[Nle]E[Nle]RCSASVECKQKCLAAIGSIFGKC[Nle]NKKCKCYPRR (SEQ ID NO. 123)
P[Nle]E[Nle]RCSASVECKQKCLAAIGSIFGKC[Nle]NKKCKCYPRY (SEQ ID NO. 124)
P[Nle]E[Nle]RCSASVECKQKCLAAIGSIFGKC[Nle]NKKCKCYPRL (SEQ ID NO. 125)
P[Nle]E[Nle]RCSASVECKQKCLAAIGSIFGKC[Nle]NKKCKCYPRH (SEQ ID NO. 126)
P[Nle]E[Nle]RCSASVECKQKCLAAIGSIFGKC[Nle]NKKCKCYPRE (SEQ ID NO. 127)
P[Nle]E[Nle]RCSASVECKQKCLAAIGSIFGKC[Nle]NKKCKCYPRKS (SEQ ID NO. 128)
P[Nle]E[Nle]RCSASVECKQKCLAAIGSIFGKC[Nle]NKKCKCYPRFE (SEQ ID NO. 129)
P[Nle]E[Nle]RCSASVECKQKCLAAIGSIFGKC[Nle]NKKCKCYPRHR (SEQ ID NO. 130)
P[Nle]E[Nle]RCSASVECKQKCLAAIGSIFGKC[Nle]NKKCKCYPRAK (SEQ ID NO. 131)
P[Nle]E[Nle]RCSASVECKQKCLAAIGSIFGKC[Nle]NKKCKCYP-[(4-amino-5-hydroxypentyl)guanidine]

(SEQ ID NO. 132)
P[Nle]E[Nle]RCSASVECKQKCLAAIGSIFGKC[Nle]NKKCKCYPR-[4-amino-5-hydroxypentanamide]

(SEQ ID NO. 133)
P[Nle]E[Nle]RCSASVECKQKCLAAIGSIFGKC[Nle]NKKCKCYPRST (SEQ ID NO. 134)
P[Nle]E[Nle]RCSASVECKQKCLAAIGSIFGKC[Nle]NKKCKCYPRRY (SEQ ID NO. 135)
P[Nle]E[Nle]RCSSSVECKQKCLAAIGSIFGKC[Nle]NKKCKCYPR (SEQ ID NO. 136)
P[Nle]E[Nle]RCSLSVECKQKCLAAIGSIFGKC[Nle]NKKCKCYPR (SEQ ID NO. 137)
P[Nle]E[Nle]RCSAPVECKQKCLAAIGSIFGKC[Nle]NKKCKCYPR (SEQ ID NO. 138)
P[Nle]E[Nle]RCSASPECKQKCLAAIGSIFGKC[Nle]NKKCKCYPR (SEQ ID NO. 139)
P[Nle]E[Nle]RCSASQECKQKCLAAIGSIFGKC[Nle]NKKCKCYPR (SEQ ID NO. 140)
P[Nle]E[Nle]RCSASVECLQKCLAAIGSIFGKC[Nle]NKKCKCYPR (SEQ ID NO. 141)
P[Nle]E[Nle]RCSASVECKQPCLAAIGSIFGKC[Nle]NKKCKCYPR (SEQ ID NO. 142)
P[Nle]E[Nle]RCEASVECKQKCLAAIGSIFGKC[Nle]NKKCKCYPR (SEQ ID NO. 143)
P[Nle]E[Nle]RCFASVECKQKCLAAIGSIFGKC[Nle]NKKCKCYPR (SEQ ID NO. 144)
P[Nle]E[Nle]RCSYSVECKQKCLAAIGSIFGKC[Nle]NKKCKCYPR (SEQ ID NO. 145)
P[Nle]E[Nle]RCSAFVECKQKCLAAIGSIFGKC[Nle]NKKCKCYPR

Ion channel blockers may comprise or consist of any of the following sequences:

(SEQ ID NO. 1)
QMDMRCSASVECKQKCLKAIGSIFGKCMNKKCKCYPR (SEQ ID NO. 2)
QMDMRCSASVECKQKCLKAIGRGFGKCMNKKCKCYPR (SEQ ID NO. 3)
NMDMRCSASVECKQKCLKAIGSIFGKCMNKKCKCYPR (SEQ ID NO. 4)
NMDMRCSASVECKQKCLKAIGRGFGKCMNKKCKCYPR (SEQ ID NO. 5)
MDMRCSASVECKQKCLKAIGSIFGKCMNKKCKCYPR (SEQ ID NO. 6)
DMRCSASVECKQKCLKAIGSIFGKCMNKKCKCYPR (SEQ ID NO. 7)
NMDMRCSASVECKQKCLKAIGSIFGKCMNKKCKCYPR (SEQ ID NO. 8)
NIDMRCSASVECKQKCLKAIGSIFGKCMNKKCKCYPR (SEQ ID NO. 9)
NMDVRCSASVECKQKCLKAIGSIFGKCMNKKCKCYPR (SEQ ID NO. 10)
NMDMRCSASVECKQKCKDAIGSIFGKCMNKKCKCYPR (SEQ ID NO. 11)
GGNMDMRCSASVECKQKCLKAIGSIFGKCMNKKCKCYPR (SEQ ID NO. 12)
NMEMRCSASVECKQKCLKAIGSIFGKCMNKKCKCYPR (SEQ ID NO. 13)
SGNMDMRCSASVECKQKCLKAIGSIFGKCMNKKCKCYPR (SEQ ID NO. 14)
N[Nle]DMRCSASVECKQKCLKAIGSIFGKCMNKKCKCYPR (SEQ ID NO. 15)
NMD[Nle]RCSASVECKQKCLKAIGSIFGKCMNKKCKCYPR (SEQ ID NO. 16)
NMDMRCSASVECKQKCLKAIGSIFGKC[Nle]NKKCKCYPR (SEQ ID NO. 17)
NMDMRCSASVECKVKCLKAIGSIFGKCMNKKCKCYPR (SEQ ID NO. 18)
NMDMRCSASVECKQLCLKAIGSIFGKCMNKKCKCYPR (SEQ ID NO. 19)
NMDMRCSASVECKQKCKKAIGSIFGKCMNKKCKCYPR (SEQ ID NO. 20)
NMDMRCSASVECKQKCLDAIGSIFGKCMNKKCKCYPR (SEQ ID NO. 21)
NMDMRCSASVECKQKCLKAIRSIFGKCMNKKCKCYPR (SEQ ID NO. 22)
NMDMRCSASVECKQKCLKAIESIFGKCMNKKCKCYPR (SEQ ID NO. 23)
NMDMRCSASVECKQKCLKAIGSIFGKCMNKKCKCYPRRRTA (SEQ ID NO. 24)
NMDMRCSASVECKQKCLKAIGSIFGKCMNKKCKCYPRHRRK (SEQ ID NO. 25)
NMDMRCKASVECKQKCLKAIGSIFGKCMNKKCKCYPR (SEQ ID NO. 26)
NMDMRCSISVECKQKCLKAIGSIFGKCMNKKCKCYPR

-continued

NMDMRCSASRECKQKCLKAIGSIFGKCMNKKCKCYPR (SEQ ID NO. 27)

NMDMRCSASVQCKQKCLKAIGSIFGKCMNKKCKCYPR (SEQ ID NO. 28)

NMDMRCSASVECLQKCLKAIGSIFGKCMNKKCKCYPR (SEQ ID NO. 29)

NMDMRCSASVECAQKCLKAIGSIFGKCMNKKCKCYPR (SEQ ID NO. 30)

NMDMRCSASVECKEKCLKAIGSIFGKCMNKKCKCYPR (SEQ ID NO. 31)

NMDMRCSASVECKLKCLKAIGSIFGKCMNKKCKCYPR (SEQ ID NO. 32)

NMDMRCSASVECKQKCLKAIHSIFGKCMNKKCKCYPR (SEQ ID NO. 33)

NMDMRCSASVECKQKCLKAIGSKFGKCMNKKCKCYPR (SEQ ID NO. 34)

NMDMRCSASVECKQKCLKAIGSRFGKCMNKKCKCYPR (SEQ ID NO. 35)

NMDMRCSASVECKQKCLKAIGSIFGKCMNGKCKCYPR (SEQ ID NO. 36)

NMDMRCSASVECKQKCLKAIGSIFGKCMNKKCHCYPR (SEQ ID NO. 37)

NMDMRCSASVECKQKCLKAIGSIFGKCMNKKCVCYPR (SEQ ID NO. 38)

N[Nle]D[Nle]RCSASVECKQKCLKAIGSIFGKCMNKKCKCYPR (SEQ ID NO. 39)

N[Nle]D[Nle]RCSASVECKQKCLKAIGSIFGKC[Nle]NKKCKCYPR (SEQ ID NO. 40)

P[Nle]D[Nle]RCSASVECKQKCLKAIGSIFGKC[Nle]NKKCKCYPR (SEQ ID NO. 41)

N[Nle]D[Nle]RCRASVECKQKCLKAIGSIFGKC[Nle]NKKCKCYPR (SEQ ID NO. 42)

N[Nle]D[Nle]RCSASVECEQKCLKAIGSIFGKC[Nle]NKKCKCYPR (SEQ ID NO. 43)

N[Nle]D[Nle]RCSASVECQQKCLKAIGSIFGKC[Nle]NKKCKCYPR (SEQ ID NO. 44)

N[Nle]D[Nle]RCSASVECKKKCLKAIGSIFGKC[Nle]NKKCKCYPR (SEQ ID NO. 45)

N[Nle]S[Nle]RCSASVECKQKCLKAIGSIFGKC[Nle]NKKCKCYPR (SEQ ID NO. 46)

N[Nle]D[Nle]RCSHSVECKQKCLKAIGSIFGKC[Nle]NKKCKCYPR (SEQ ID NO. 47)

N[Nle]D[Nle]RCSASVECKQSCLKAIGSIFGKC[Nle]NKKCKCYPR (SEQ ID NO. 48)

N[Nle]D[Nle]RCSASVECKQKCKAIGSIFGKC[Nle]NKKCKCYPR (SEQ ID NO. 49)

NMDMRCSASVECKQKCYKAIGSIFGKCMNKKCKCYPR (SEQ ID NO. 50)

NMDMRCSASVECKQKCRKAIGSIFGKCMNKKCKCYPR (SEQ ID NO. 51)

NMDMRCSASVECKQKCLAAIGSIFGKCMNKKCKCYPR (SEQ ID NO. 52)

NMDMRCSASVECKQKCLYAIGSIFGKCMNKKCKCYPR (SEQ ID NO. 53)

-continued

NMDMRCSASVECKQKCLAIGSIFGKCMNKKCKCYPR (SEQ ID NO. 54)

NMDMRCSASVECKQKCLKYIGSIFGKCMNKKCKCYPR (SEQ ID NO. 55)

NMDMRCSASVECKQKCLKRIGSIFGKCMNKKCKCYPR (SEQ ID NO. 56)

NMDMRCSASVECKQKCLKIGSIFGKCMNKKCKCYPR (SEQ ID NO. 57)

NMDMRCSASVECKQKCLKAYGSIFGKCMNKKCKCYPR (SEQ ID NO. 58)

NMDMRCSASVECKQKCLKAEGSIFGKCMNKKCKCYPR (SEQ ID NO. 59)

NMDMRCSASVECKQKCLKARGSIFGKCMNKKCKCYPR (SEQ ID NO. 60)

NMDMRCSASVECKQKCLKAGSIFGKCMNKKCKCYPR (SEQ ID NO. 61)

N[Nle]D[Nle]RCSASVECKQKCLKAIGSPFGKC[Nle]NKKCKCYPR (SEQ ID NO. 62)

N[Nle]D[Nle]RCSASKECKQKCLKAIGSIFGKC[Nle]NKKCKCYPR (SEQ ID NO. 63)

H[Nle]D[Nle]RCSASVECKQKCLKAIGSIFGKC[Nle]NKKCKCYPR (SEQ ID NO. 64)

Y[Nle]D[Nle]RCSASVECKQKCLKAIGSIFGKC[Nle]NKKCKCYPR (SEQ ID NO. 65)

S[Nle]D[Nle]RCSASVECKQKCLKAIGSIFGKC[Nle]NKKCKCYPR (SEQ ID NO. 66)

V[Nle]D[Nle]RCSASVECKQKCLKAIGSIFGKC[Nle]NKKCKCYPR (SEQ ID NO. 67)

S[Nle]D[Nle]RCSA[Abu]VECKQKCLKAIGSIFGKCMNKKCKCYPR (SEQ ID NO. 68)

S[Nle]D[Nle]RCSASVECKQKCLKAIGSIFG[homo-Lys]CMNKKCKCYPR (SEQ ID NO. 69)

S[Nle]D[Nle]RCSASVECKQKCLKAIGSIFGKCMNKKCKC[F(4-NH2)]PR (SEQ ID NO. 70)

S[Nle]D[Nle]RCSASVECGQKCLKAIGSIFGKCMNKKCKCYPR (SEQ ID NO. 71)

S[Nle]D[Nle]RCSASVECVQKCLKAIGSIFGKCMNKKCKCYPR (SEQ ID NO. 72)

S[Nle]D[Nle]RCSASVECK[2-Amino-5-carboxypentanoyl]KCLKAIGSIFGKCMNKKCKCYPR (SEQ ID NO. 73)

S[Nle]D[Nle]RCSASVECKQKCLKAIGSIFGKCMNKKCKCYQ (SEQ ID NO. 74)

S[Nle]D[Nle]RCSASVECKQKCLKAIGSIFGKCMNKKCRCYPR (SEQ ID NO. 75)

S[Nle]DERCSASVECKQKCLKAIGSIFGKCMNKKCKCYPR (SEQ ID NO. 76)

S[Nle]D[Nle]RCSASVECKQKCLGAIGSIFGKCMNKKCKCYPR (SEQ ID NO. 77)

S[Nle]D[Nle]RCSASVECKQKCLVAIGSIFGKCMNKKCKCYPR (SEQ ID NO. 78)

S[Nle]D[Nle]RCSASVECAQSCLKAIGSIFGKCMNKKCKCYPR (SEQ ID NO. 79)

```
                                                        (SEQ ID NO. 80)
S[Nle]D[Nle]RCSASVECAQKCLAAIGSIFGKCMNKKCKCYPR (SEQ ID NO. 81)
S[Nle]D[Nle]RCSASVECAQLCLAAIGSIFGKCMNKKCKCYPR (SEQ ID NO. 82)
S[Nle]D[Nle]RCSASVECKQKCLKAIGSIFGKC[Nle]NKKCKCYPR (SEQ ID NO. 83)
P[Nle]D[Nle]RCSASVECKQKCLKAIGCIFGKC[Nle]NKKCKCYPC (SEQ ID NO. 84)
S[Nle]D[Nle]RCSASVECKEKCLQAIGSIFGKC[Nle]NKKCKCYPR (SEQ ID NO. 85)
P[Nle]D[Nle]RCSASVECKEKCL[homo-Gln]AIGSIFGKC[Nle]NKKCKCYPR (SEQ ID NO. 86)
CSASVECKQKCLKAIGCIFGKC[Nle]NKKCKCYPC (SEQ ID NO. 87)
S[Nle]D[Nle]RCSASVECKQKCLAAIGCIFGKC[Nle]NKKCKCYPC (SEQ ID NO. 88)
P[Nle]D[Nle]RCSASVECKQKCLKAIGCIFGKC[Nle]NKKCKCYPC (SEQ ID NO. 89)
S[Nle]D[Nle]RCSALVECKQKCLKAIGSIFGKCMNKKCKCYPR (SEQ ID NO. 90)
S[Nle]D[Nle]RCSAVVECKQKCLKAIGSIFGKCMNKKCKCYPR (SEQ ID NO. 91)
S[Nle]D[Nle]RCSASVECKQKCLKAIGSIFGKCMNKKCKC[F(4-F)]PR (SEQ ID NO. 92)
S[Nle]D[Nle]RCSASVECKQKCLKAIGSIFGKCMNKKCKC[F(4-NO$_2$)]PR (SEQ ID NO. 93)
S[Nle]D[Nle]RCSASVECKQKCLKAIGSIFGKCMNKKCKC[F(4-CH$_3$)]PR (SEQ ID NO. 94)
[Nle]D[Nle]RCSASVECKQKCLKAIGSIFGKC[Nle]NKKCKCYPR (SEQ ID NO. 95)
NID[Nle]RCSASVECKQKCLKAIGSIFGKC[Nle]NKKCKCYPR (SEQ ID NO. 96)
PIE[Nle]RCSASVECKQKCLKAIGSIFGKC[Nle]NKKCKCYPR (SEQ ID NO. 97)
P[Nle]E[Nle]RCSASVECKQKCLAAIGSIFGKC[Nle]NKKCKCYPR (SEQ ID NO. 98)
P[Nle]E[Nle]RCSASVECKQKCLAAIGSIFGKC[Nle]NKKCKCYPR (SEQ ID NO. 99)
P[Nle]E[Nle]RCSASVECKQKCLLAIGSIFGKC[Nle]NKKCKCYPR (SEQ ID NO. 100)
PIDERCSASVECKQKCLAAIGSIFGKC[Nle]NKKCKCYPR (SEQ ID NO. 101)
PIE[Nle]RCSASVECKQKCLAAIGSIFGKC[Nle]NKKCKCYPR (SEQ ID NO. 102)
P[Nle]D[Nle]RCSASVECAQKCLAAIGSIFGKCMNKKCKCYPR (SEQ ID NO. 103)
P[Nle]E[Nle]RCSASVECAQKCLAAIGSIFGKC[Nle]NKKCKCYPR (SEQ ID NO. 104)
CSASVECKQKCLKAIGSIFGKC[Nle]NKKCKCYPR (SEQ ID NO. 105)
CSASVECKQKCLKAIGSIFGKC[Nle]NKKCKCYPR (SEQ ID NO. 106)
RCSASVECKQKCLKAIGSIFGKC[Nle]NKKCKCYPR
```

-continued

```
                                              (SEQ ID NO. 107)
SKCSASVECKQKCLKAIGSIFGKC[Nle]NKKCKCYPR (SEQ ID NO. 108)
LRCSASVECKQKCLKAIGSIFGKC[Nle]NKKCKCYPR (SEQ ID NO. 109)
CSASVECKQKCLKAIGSIFGKC[Nle]NKKCKCYPS (SEQ ID NO. 110)
CSASVECKQKCLKAIGSIFGKC[Nle]NKKCKCYS (SEQ ID NO. 111)
CSASVECKQKCLKAIGSIFGKC[Nle]NKKCKCYG-NH2

(SEQ ID NO. 112)
CSASVECKQKCLKAIGSIFGKC[Nle]NKKCKCY-NH2

(SEQ ID NO. 113)
RCSASVECKQKCLKAIGSIFGKC[Nle]NKKCKCYPR (SEQ ID NO. 114)
LRCSASVECKQKCLKAIGSIFGKC[Nle]NKKCKCYPR (SEQ ID NO. 115)
LRCSASVECKQKCLAAIGSIFGKC[Nle]NKKCKCYPR (SEQ ID NO. 116)
LRCSASVECKQKCLAAIGSIFGKCMNKKCKCYPR (SEQ ID NO. 117)
CSASVECKQKCLKAIGSIFGKCMNKKCKCYPR (SEQ ID NO. 118)
P[Nle]E[Nle]RCSASVECKEKCLAAIGSIFGKC[Nle]NKKCKCYPR (SEQ ID NO. 119)
p[Nle]E[Nle]RCSASVECKQKCLAAIGSIFGKC[Nle]NKKCKCYPR (SEQ ID NO. 120)
P[Nle]E[Nle]RCSASVECKQKCLAAIGSIFGKC[Nle]NKKCKCYR (SEQ ID NO. 121)
[Nle]E[Nle]RCSASVECKQKCLAAIGSIFGKC[Nle]NKKCKCYPR (SEQ ID NO. 122)
P[Nle]E[Nle]RCSASVECKQKCLAAIGSIFGKC[Nle]NKKCKCYPRR (SEQ ID NO. 123)
P[Nle]E[Nle]RCSASVECKQKCLAAIGSIFGKC[Nle]NKKCKCYPRY (SEQ ID NO. 124)
P[Nle]E[Nle]RCSASVECKQKCLAAIGSIFGKC[Nle]NKKCKCYPRL (SEQ ID NO. 125)
P[Nle]E[Nle]RCSASVECKQKCLAAIGSIFGKC[Nle]NKKCKCYPRH (SEQ ID NO. 126)
P[Nle]E[Nle]RCSASVECKQKCLAAIGSIFGKC[Nle]NKKCKCYPRE (SEQ ID NO. 127)
P[Nle]E[Nle]RCSASVECKQKCLAAIGSIFGKC[Nle]NKKCKCYPRKS (SEQ ID NO. 128)
P[Nle]E[Nle]RCSASVECKQKCLAAIGSIFGKC[Nle]NKKCKCYPRFE (SEQ ID NO. 129)
P[Nle]E[Nle]RCSASVECKQKCLAAIGSIFGKC[Nle]NKKCKCYPRHR (SEQ ID NO. 130)
P[Nle]E[Nle]RCSASVECKQKCLAAIGSIFGKC[Nle]NKKCKCYPRAK (SEQ ID NO. 131)
P[Nle]E[Nle]RCSASVECKQKCLAAIGSIFGKC[Nle]NKKCKCYP-[(4-amino-
5-hydroxypentyl)guanidine]
```

(SEQ ID NO. 132)
P[Nle]E[Nle]RCSASVECKQKCLAAIGSIFGKC[Nle]NKKCKCYPR-[4-amino-5-hydroxypentanamide]

(SEQ ID NO. 133)
P[Nle]E[Nle]RCSASVECKQKCLAAIGSIFGKC[Nle]NKKCKCYPRST (SEQ ID NO. 134)
P[Nle]E[Nle]RCSASVECKQKCLAAIGSIFGKC[Nle]NKKCKCYPRRY (SEQ ID NO. 135)
P[Nle]E[Nle]RCSSSVECKQKCLAAIGSIFGKC[Nle]NKKCKCYPR (SEQ ID NO. 136)
P[Nle]E[Nle]RCSLSVECKQKCLAAIGSIFGKC[Nle]NKKCKCYPR (SEQ ID NO. 137)
P[Nle]E[Nle]RCSAPVECKQKCLAAIGSIFGKC[Nle]NKKCKCYPR (SEQ ID NO. 138)
P[Nle]E[Nle]RCSASPECKQKCLAAIGSIFGKC[Nle]NKKCKCYPR (SEQ ID NO. 139)
P[Nle]E[Nle]RCSASQECKQKCLAAIGSIFGKC[Nle]NKKCKCYPR (SEQ ID NO. 140)
P[Nle]E[Nle]RCSASVECLQKCLAAIGSIFGKC[Nle]NKKCKCYPR (SEQ ID NO. 141)
P[Nle]E[Nle]RCSASVECKQPCLAAIGSIFGKC[Nle]NKKCKCYPR (SEQ ID NO. 142)
P[Nle]E[NlORCEASVECKQKCLAAIGSIFGKC[Nle]NKKCKCYPR (SEQ ID NO. 143)
P[Nle]E[Nle]RCFASVECKQKCLAAIGSIFGKC[Nle]NKKCKCYPR (SEQ ID NO. 144)
P[Nle]E[Nle]RCSYSVECKQKCLAAIGSIFGKC[Nle]NKKCKCYPR (SEQ ID NO. 145)
P[Nle]E[Nle]RCSAFVECKQKCLAAIGSIFGKC[Nle]NKKCKCYPR

In some embodiments, the ion channel blocker does not have the sequence:

(SEQ ID NO. 1)
QMDMRCSASVECKQKCLKAIGSIFGKCMNKKCKCYPR or (SEQ ID NO. 2)
QMDMRCSASVECKQKCLKAIGRGFGKCMNKKCKCYPR.

In some embodiments, $R^1$ is H and $R^2$ is $NH_2$ or OH. In some embodiments, it may be desirable that $R^2$ is OH.

Ion channel blockers include the following:

(Cpd. 1)
(SEQ ID NO. 1)
H-QMDMRCSASVECKQKCLKAIGSIFGKCMNKKCKCYPR-OH (Cpd. 2)
(SEQ ID NO. 2)
H-QMDMRCSASVECKQKCLKAIGRGFGKCMNKKCKCYPR-OH (Cpd. 3)
(SEQ ID NO. 3)
H-NMDMRCSASVECKQKCLKAIGSIFGKCMNKKCKCYPR-OH (Cpd. 4)
(SEQ ID NO. 4)
H-NMDMRCSASVECKQKCLKAIGRGFGKCMNKKCKCYPR-OH (Cpd. 5)
(SEQ ID NO. 5)
H-MDMRCSASVECKQKCLKAIGSIFGKCMNKKCKCYPR-OH (Cpd. 6)
(SEQ ID NO. 6)
H-DMRCSASVECKQKCLKAIGSIFGKCMNKKCKCYPR-OH

-continued (Cpd. 7)
(SEQ ID NO. 7)
H-NMDMRCSASVECKQKCLKAIGSIFGKCMNKKCKCYPR-NH$_2$ (Cpd. 8)
(SEQ ID NO. 8)
H-NIDMRCSASVECKQKCLKAIGSIFGKCMNKKCKCYPR-OH (Cpd. 9)
(SEQ ID NO. 9)
H-NMDVRCSASVECKQKCLKAIGSIFGKCMNKKCKCYPR-OH (Cpd. 10)
(SEQ ID NO. 10)
H-NMDMRCSASVECKQKCKDAIGSIFGKCMNKKCKCYPR-OH (Cpd. 11)
(SEQ ID NO. 11)
H-GGNMDMRCSASVECKQKCLKAIGSIFGKCMNKKCKCYPR-OH (Cpd. 12)
(SEQ ID NO. 12)
H-NMEMRCSASVECKQKCLKAIGSIFGKCMNKKCKCYPR-OH (Cpd. 13)
(SEQ ID NO. 13)
H-SGNMDMRCSASVECKQKCLKAIGSIFGKCMNKKCKCYPR-OH (Cpd. 14)
(SEQ ID NO. 14)
H-N[Nle]DMRCSASVECKQKCLKAIGSIFGKCMNKKCKCYPR-NH$_2$ (Cpd. 15)
(SEQ ID NO. 15)
H-NMD[Nle]RCSASVECKQKCLKAIGSIFGKCMNKKCKCYPR-NH$_2$ (Cpd. 16)
(SEQ ID NO. 16)
H-NMDMRCSASVECKQKCLKAIGSIFGKC[Nle]NKKCKCYPR-NH$_2$ (Cpd. 17)
(SEQ ID NO. 17)
H-NMDMRCSASVECKVKCLKAIGSIFGKCMNKKCKCYPR-NH$_2$ (Cpd. 18)
(SEQ ID NO. 18)
H-NMDMRCSASVECKQLCLKAIGSIFGKCMNKKCKCYPR-NH$_2$ (Cpd. 19)
(SEQ ID NO. 19)
H-NMDMRCSASVECKQKCKKAIGSIFGKCMNKKCKCYPR-NH$_2$ (Cpd. 20)
(SEQ ID NO. 20)
H-NMDMRCSASVECKQKCLDAIGSIFGKCMNKKCKCYPR-NH$_2$ (Cpd. 21)
(SEQ ID NO. 21)
H-NMDMRCSASVECKQKCLKAIRSIFGKCMNKKCKCYPR-NH$_2$ (Cpd. 22)
(SEQ ID NO. 22)
H-NMDMRCSASVECKQKCLKAIESIFGKCMNKKCKCYPR-NH$_2$ (Cpd. 23)
(SEQ ID NO. 23)
H-NMDMRCSASVECKQKCLKAIGSIFGKCMNKKCKCYPRRRTA-NH$_2$ (Cpd. 24)
(SEQ ID NO. 24)
H-NMDMRCSASVECKQKCLKAIGSIFGKCMNKKCKCYPRHRRK-NH$_2$ (Cpd. 25)
(SEQ ID NO. 25)
H-NMDMRCKASVECKQKCLKAIGSIFGKCMNKKCKCYPR-NH$_2$ (Cpd. 26)
(SEQ ID NO. 26)
H-NMDMRCSISVECKQKCLKAIGSIFGKCMNKKCKCYPR-NH$_2$ -continued (Cpd. 27)
(SEQ ID NO. 27)
H-NMDMRCSASRECKQKCLKAIGSIFGKCMNKKCKCYPR-NH$_2$ (Cpd. 28)
(SEQ ID NO. 28)
H-NMDMRCSASVQCKQKCLKAIGSIFGKCMNKKCKCYPR-NH$_2$ (Cpd. 29)
(SEQ ID NO. 29)
H-NMDMRCSASVECLQKCLKAIGSIFGKCMNKKCKCYPR-NH$_2$ (Cpd. 30)
(SEQ ID NO. 30)
H-NMDMRCSASVECAQKCLKAIGSIFGKCMNKKCKCYPR-NH$_2$ (Cpd. 31)
(SEQ ID NO. 31)
H-NMDMRCSASVECKEKCLKAIGSIFGKCMNKKCKCYPR-NH$_2$ (Cpd. 32)
(SEQ ID NO. 32)
H-NMDMRCSASVECKLKCLKAIGSIFGKCMNKKCKCYPR-NH$_2$ (Cpd. 33)
(SEQ ID NO. 33)
H-NMDMRCSASVECKQKCLKAIHSIFGKCMNKKCKCYPR-NH$_2$ (Cpd. 34)
(SEQ ID NO. 34)
H-NMDMRCSASVECKQKCLKAIGSKFGKCMNKKCKCYPR-NH$_2$ (Cpd. 35)
(SEQ ID NO. 35)
H-NMDMRCSASVECKQKCLKAIGSRFGKCMNKKCKCYPR-NH$_2$ (Cpd. 36)
(SEQ ID NO. 36)
H-NMDMRCSASVECKQKCLKAIGSIFGKCMNGKCKCYPR-NH$_2$ (Cpd. 37)
(SEQ ID NO. 37)
H-NMDMRCSASVECKQKCLKAIGSIFGKCMNKKCHCYPR-NH$_2$ (Cpd. 38)
(SEQ ID NO 38)
H-NMDMRCSASVECKQKCLKAIGSIFGKCMNKKCVCYPR-NH$_2$ (Cpd. 39)
(SEQ ID NO. 39)
H-N[Nle]D[Nle]RCSASVECKQKCLKAIGSIFGKCMNKKCKCYPR-NH$_2$ (Cpd. 40)
(SEQ ID NO. 40)
H-N[Nle]D[Nle]RCSASVECKQKCLKAIGSIFGKC[Nle]NKKCKCYPR-NH$_2$ (Cpd. 41)
(SEQ ID NO. 41)
H-P[Nle]D[Nle]RCSASVECKQKCLKAIGSIFGKC[Nle]NKKCKCYPR-NH$_2$ (Cpd. 42)
(SEQ ID NO. 42)
H-N[Nle]D[Nle]RCRASVECKQKCLKAIGSIFGKC[Nle]NKKCKCYPR-NH$_2$ (Cpd. 43)
(SEQ ID NO. 43)
H-N[Nle]D[Nle]RCSASVECEQKCLKAIGSIFGKC[Nle]NKKCKCYPR-NH$_2$ (Cpd. 44)
(SEQ ID NO. 44)
H-N[Nle]D[Nle]RCSASVECQQKCLKAIGSIFGKC[Nle]NKKCKCYPR-NH$_2$ (Cpd. 45)
(SEQ ID NO. 45)
H-N[Nle]D[Nle]RCSASVECKKKCLKAIGSIFGKC[Nle]NKKCKCYPR-NH$_2$ (Cpd. 46)
(SEQ ID NO. 46)
H-N[Nle]S[Nle]RCSASVECKQKCLKAIGSIFGKC[Nle]NKKCKCYPR-NH$_2$ -continued (Cpd. 47)
(SEQ ID NO. 47)
H-N[Nle]D[Nle]RCSHSVECKQKCLKAIGSIFGKC[Nle]NKKCKCYPR-NH$_2$ (Cpd. 48)
(SEQ ID NO. 48)
H-N[Nle]D[Nle]RCSASVECKQSCLKAIGSIFGKC[Nle]NKKCKCYPR-NH$_2$ (Cpd. 49)
(SEQ ID NO. 49)
H-N[Nle]D[Nle]RCSASVECKQKCKAIGSIFGKC[Nle]NKKCKCYPR-NH$_2$ (Cpd. 50)
(SEQ ID NO. 50)
H-NMDMRCSASVECKQKCYKAIGSIFGKCMNKKCKCYPR-NH$_2$ (Cpd. 51)
(SEQ ID NO. 51)
H-NMDMRCSASVECKQKCRKAIGSIFGKCMNKKCKCYPR-NH$_2$ (Cpd. 52)
(SEQ ID NO. 52)
H-NMDMRCSASVECKQKCLAAIGSIFGKCMNKKCKCYPR-NH$_2$ (Cpd. 53)
(SEQ ID NO. 53)
H-NMDMRCSASVECKQKCLYAIGSIFGKCMNKKCKCYPR-NH$_2$ (Cpd. 54)
(SEQ ID NO. 54)
H-NMDMRCSASVECKQKCLAIGSIFGKCMNKKCKCYPR-NH$_2$ (Cpd. 55)
(SEQ ID NO. 55)
H-NMDMRCSASVECKQKCLKYIGSIFGKCMNKKCKCYPR-NH$_2$ (Cpd. 56)
(SEQ ID NO. 56)
H-NMDMRCSASVECKQKCLKRIGSIFGKCMNKKCKCYPR-NH$_2$ (Cpd. 57)
(SEQ ID NO. 57)
H-NMDMRCSASVECKQKCLKIGSIFGKCMNKKCKCYPR-NH$_2$ (Cpd. 58)
(SEQ ID NO. 58)
H-NMDMRCSASVECKQKCLKAYGSIFGKCMNKKCKCYPR-NH$_2$ (Cpd. 59)
(SEQ ID NO. 59)
H-NMDMRCSASVECKQKCLKAEGSIFGKCMNKKCKCYPR-NH$_2$ (Cpd. 60)
(SEQ ID NO. 60)
H-NMDMRCSASVECKQKCLKARGSIFGKCMNKKCKCYPR-NH$_2$ (Cpd. 61)
(SEQ ID NO. 61)
H-NMDMRCSASVECKQKCLKAGSIFGKCMNKKCKCYPR-NH$_2$ (Cpd. 62)
(SEQ ID NO. 62)
H-N[Nle]D[Nle]RCSASVECKQKCLKAIGSPFGKC[Nle]NKKCKCYPR-NH$_2$ (Cpd. 63)
(SEQ ID NO. 63)
H-N[Nle]D[Nle]RCSASKECKQKCLKAIGSIFGKC[Nle]NKKCKCYPR-NH$_2$ (Cpd. 64)
(SEQ ID NO. 64)
H-H[Nle]D[Nle]RCSASVECKQKCLKAIGSIFGKC[Nle]NKKCKCYPR-NH$_2$ (Cpd. 65)
(SEQ ID NO. 65)
H-Y[Nle]D[Nle]RCSASVECKQKCLKAIGSIFGKC[Nle]NKKCKCYPR-NH$_2$ (Cpd. 66)
(SEQ ID NO. 66)
H-S[Nle]D[Nle]RCSASVECKQKCLKAIGSIFGKC[Nle]NKKCKCYPR-NH$_2$ -continued (Cpd. 67)
(SEQ ID NO. 67)
H-V[Nle]D[Nle]RCSASVECKQKCLKAIGSIFGKC[Nle]NKKCKCYPR-NH$_2$ (Cpd. 68)
(SEQ ID NO. 68)
H-S[Nle]D[Nle]RCSA[Abu]VECKQKCLKAIGSIFGKCMNKKCKCYPR-NH$_2$ (Cpd. 69)
(SEQ ID NO. 69)
H-S[Nle]D[Nle]RCSASVECKQKCLKAIGSIFG[homo-Lys]CMNKKCKCYPR-NH$_2$ (Cpd. 70)
(SEQ ID NO. 70)
H-S[Nle]D[Nle]RCSASVECKQKCLKAIGSIFGKCMNKKCKC[F(4-NH2)]PR-NH$_2$ (Cpd. 71)
(SEQ ID NO. 71)
H-S[Nle]D[Nle]RCSASVECGQKCLKAIGSIFGKCMNKKCKCYPR-NH$_2$ (Cpd. 72)
(SEQ ID NO. 72)
H-S[Nle]D[Nle]RCSASVECVQKCLKAIGSIFGKCMNKKCKCYPR-NH$_2$ (Cpd. 73)
(SEQ ID NO. 73)
H-S[Nle]D[Nle]RCSASVECK[2-Amino-5-carboxypentanoyl]KCLKAIGSIFGKCMNKKCKCYPR-NH$_2$ (Cpd. 74)
(SEQ ID NO. 74)
H-S[Nle]D[Nle]RCSASVECKQKCLKAIGSIFGKCMNKKCKCYQ-NH$_2$ (Cpd. 75)
(SEQ ID NO. 75)
H-S[Nle]D[Nle]RCSASVECKQKCLKAIGSIFGKCMNKKCIRCYPR-NH$_2$ (Cpd. 76)
(SEQ ID NO. 76)
H-S[Nle]DERCSASVECKQKCLKAIGSIFGKCMNKKCKCYPR-NH$_2$ (Cpd. 77)
(SEQ ID NO. 77)
H-S[Nle]D[Nle]RCSASVECKQKCLGAIGSIFGKCMNKKCKCYPR-NH$_2$ (Cpd. 78)
(SEQ ID NO. 78)
H-S[Nle]D[Nle]RCSASVECKQKCLVAIGSIFGKCMNKKCKCYPR-NH$_2$ (Cpd. 79)
(SEQ ID NO. 79)
H-S[Nle]D[Nle]RCSASVECAQSCLKAIGSIFGKCMNKKCKCYPR-NH$_2$ (Cpd. 80)
(SEQ ID NO. 80)
H-S[Nle]D[Nle]RCSASVECAQKCLAAIGSIFGKCMNKKCKCYPR-NH$_2$ (Cpd. 81)
(SEQ ID NO. 81)
H-S[Nle]D[Nle]RCSASVECAQLCLAAIGSIFGKCMNKKCKCYPR-NH$_2$ (Cpd. 82)
(SEQ ID NO. 82)
H-S[Nle]D[Nle]RCSASVECKQKCLKAIGSIFGKC[Nle]NKKCKCYPR-OH (Cpd. 83)
(SEQ ID NO. 83)
H-P[Nle]D[Nle]RCSASVECKQKCLKAIGCIFGKC[Nle]NKKCKCYPC-NH$_2$ (Cpd. 84)
(SEQ ID NO. 84)
H-S[Nle]D[Nle]RCSASVECKEKCLQAIGSIFGKC[Nle]NKKCKCYPR-NH$_2$ (Cpd. 85)
(SEQ ID NO. 85)
H-P[Nle]D[Nle]RCSASVECKEKCL[homo-Gln]AlGSIFGKC[Nle]NKKCKCYPR-NH$_2$ (Cpd. 86)
(SEQ ID NO. 86)
H-CSASVECKQKCLKAIGCIFGKC[Nle]NKKCKCYPC-NH$_2$ -continued (Cpd. 87)
(SEQ ID NO. 87)
H-S[Nle]D[Nle]RCSASVECKQKCLAAIGCIFGKC[Nle]NKKCKCYPC-NH$_2$ (Cpd. 88)
(SEQ ID NO. 88)
H-P[Nle]D[Nle]RCSASVECKQKCLKAIGCIFGKC[Nle]NKKCKCYPC-OH (Cpd. 89)
(SEQ ID NO. 89)
H-S[Nle]D[Nle]RCSALVECKQKCLKAIGSIFGKCMNKKCKCYPR-NH$_2$ (Cpd. 90)
(SEQ ID NO. 90)
H-S[Nle]D[Nle]RCSAVVECKQKCLKAIGSIFGKCMNKKCKCYPR-NH$_2$ (Cpd. 91)
(SEQ ID NO. 91)
H-S[Nle]D[Nle]RCSASVECKQKCLKAIGSIFGKCMNKKCKC[F(4-F)]PR-NH$_2$ (Cpd. 92)
(SEQ ID NO. 92)
H-S[Nle]D[Nle]RCSASVECKQKCLKAIGSIFGKCMNKKCKC[F(4-NO$_2$)PR-NH$_2$ (Cpd. 93)
(SEQ ID NO. 93)
H-S[Nle]D[Nle]RCSASVECKQKCLKAIGSIFGKCMNKKCKC[F(4-CH$_3$)]PR-NH$_2$ (Cpd. 94)
(SEQ ID NO. 94)
H-[Nle]D[Nle]RCSASVECKQKCLKAIGSIFGKC[Nle]NKKCKCYPR-OH (Cpd. 95)
(SEQ ID NO. 95)
H-NID[Nle]RCSASVECKQKCLKAIGSIFGKC[Nle]NKKCKCYPR-OH (Cpd. 96)
(SEQ ID NO. 96)
H-PIE[Nle]RCSASVECKQKCLKAIGSIFGKC[Nle]NKKCKCYPR-OH (Cpd. 97)
(SEQ ID NO. 97)
H-P[Nle]E[Nle]RCSASVECKQKCLAAIGSIFGKC[Nle]NKKCKCYPR-OH (Cpd. 98)
(SEQ ID NO. 98)
H-P[Nle]E[Nle]RCSASVECKQKCLAAIGSIFGKC[Nle]NKKCKCYPR-NH$_2$ (Cpd. 99)
(SEQ ID NO. 99)
H-P[Nle]E[Nle]RCSASVECKQKCLLAIGSIFGKC[Nle]NKKCKCYPR-OH (Cpd. 100)
(SEQ ID NO. 100)
H-PIDERCSASVECKQKCLAAIGSIFGKC[Nle]NKKCKCYPR-OH (Cpd. 101)
(SEQ ID NO. 101)
H-PIE[Nle]RCSASVECKQKCLAAIGSIFGKC[Nle]NKKCKCYPR-OH (Cpd. 102)
(SEQ ID NO. 102)
H-P[Nle]D[Nle]RCSASVECAQKCLAAIGSIFGKCMNKKCKCYPR-OH (Cpd. 103)
(SEQ ID NO. 103)
H-P[Nle]E[Nle]RCSASVECAQKCLAAIGSIFGKC[Nle]NKKCKCYPR-OH (Cpd. 104)
(SEQ ID NO. 104)
H-CSASVECKQKCLKAIGSIFGKC[Nle]NKKCKCYPR-NH$_2$ (Cpd. 105)
(SEQ ID NO. 105)
Ac-CSASVECKQKCLKAIGSIFGKC[Nle]NKKCKCYPR-NH$_2$ (Cpd. 106)
(SEQ ID NO. 106)
H-RCSASVECKQKCLKAIGSIFGKC[Nle]NKKCKCYPR-NH$_2$ -continued (Cpd. 107)
(SEQ ID NO. 107)
Ac-SKCSASVECKQKCLKAIGSIFGKC[Nle]NKKCKCYPR-NH$_2$ (Cpd. 108)
(SEQ ID NO. 108)
Ac-LRCSASVECKQKCLKAIGSIFGKC[Nle]NKKCKCYPR-NH$_2$ (Cpd. 109)
(SEQ ID NO. 109)
Ac-CSASVECKQKCLKAIGSIFGKC[Nle]NKKCKCYPS-NH$_2$ (Cpd. 110)
(SEQ ID NO. 110)
Ac-CSASVECKQKCLKAIGSIFGKC[Nle]NKKCKCYS-NH$_2$ (Cpd. 111)
(SEQ ID NO. 111)
Ac-CSASVECKQKCLKAIGSIFGKC[Nle]NKKCKCYG-NH$_2$ (Cpd. 112)
(SEQ ID NO. 112)
Ac-CSASVECKQKCLKAIGSIFGKC[Nle]NKKCKCY-NH$_2$ (Cpd. 113)
(SEQ ID NO. 113)
Ac-RCSASVECKQKCLKAIGSIFGKC[Nle]NKKCKCYPR-OH (Cpd. 114)
(SEQ ID NO. 114)
H-LRCSASVECKQKCLKAIGSIFGKC[Nle]NKKCKCYPR-OH (Cpd. 115)
(SEQ ID NO. 115)
Ac-LRCSASVECKQKCLAAIGSIFGKC[Nle]NKKCKCYPR-OH (Cpd. 116)
(SEQ ID NO. 116)
Ac-LRCSASVECKQKCLAAIGSIFGKCMNKKCKCYPR-OH (Cpd. 117)
(SEQ ID NO. 117)
H-CSASVECKQKCLKAIGSIFGKCMNKKCKCYPR-OH (Cpd. 118)
(SEQ ID NO. 118)
H-P[Nle]E[Nle]RCSASVECKEKCLAAIGSIFGKC[Nle]NKKCKCYPR-OH (Cpd. 119)
(SEQ ID NO. 119)
H-p[Nle]E[Nle]RCSASVECKQKCLAAIGSIFGKC[Nle]NKKCKCYPR-OH (Cpd. 120)
(SEQ ID NO. 120)
H-P[Nle]E[Nle]RCSASVECKQKCLAAIGSIFGKC[Nle]NKKCKCYR-OH (Cpd. 121)
(SEQ ID NO. 121)
H-[Nle]E[Nle]RCSASVECKQKCLAAIGSIFGKC[Nle]NKKCKCYPR-OH (Cpd. 122)
(SEQ ID NO. 122)
H-P[Nle]E[Nle]RCSASVECKQKCLAAIGSIFGKC[Nle]NKKCKCYPRR-OH (Cpd. 123)
(SEQ ID NO. 123)
H-P[Nle]E[Nle]RCSASVECKQKCLAAIGSIFGKC[Nle]NKKCKCYPRY-OH (Cpd. 124)
(SEQ ID NO. 124)
H-P[Nle]E[Nle]RCSASVECKQKCLAAIGSIFGKC[Nle]NKKCKCYPRL-OH (Cpd. 125)
(SEQ ID NO. 125)
H-P[Nle]E[Nle]RCSASVECKQKCLAAIGSIFGKC[Nle]NKKCKCYPRH-OH (Cpd. 126)
(SEQ ID NO. 126)
H-P[Nle]E[Nle]RCSASVECKQKCLAAIGSIFGKC[Nle]NKKCKCYPRE-OH -continued (Cpd. 127)
(SEQ ID NO. 127)
H-P[Nle]E[Nle]RCSASVECKQKCLAAIGSIFGKC[Nle]NKKCKCYPRKS-OH (Cpd. 128)
(SEQ ID NO. 128)
H-P[Nle]E[Nle]RCSASVECKQKCLAAIGSIFGKC[Nle]NKKCKCYPRFE-OH (Cpd. 129)
(SEQ ID NO. 129)
H-P[Nle]E[Nle]RCSASVECKQKCLAAIGSIFGKC[Nle]NKKCKCYPRHR-OH (Cpd. 130)
(SEQ ID NO. 130)
H-P[Nle]E[Nle]RCSASVECKQKCLAAIGSIFGKC[Nle]NKKCKCYPRAK-OH (Cpd. 131)
(SEQ ID NO. 131)
H-P[Nle]E[Nle]RCSASVECKQKCLAAIGSIFGKC[Nle]NKKCKCYP-[(4-amino-5-hydroxypentyl)guanidine]

(Cpd. 132)
(SEQ ID NO. 132)
H-P[Nle]E[Nle]RCSASVECKQKCLAAIGSIFGKC[Nle]NKKCKCYPR-[4-amino-5-hydroxypentanamide]

(Cpd. 133)
(SEQ ID NO. 133)
H-P[Nle]E[Nle]RCSASVECKQKCLAAIGSIFGKC[Nle]NKKCKCYPRST-OH (Cpd. 134)
(SEQ ID NO. 134)
H-P[Nle]E[Nle]RCSASVECKQKCLAAIGSIFGKC[Nle]NKKCKCYPRRY-OH (Cpd. 135)
(SEQ ID NO. 135)
H-P[Nle]E[Nle]RCSSSVECKQKCLAAIGSIFGKC[Nle]NKKCKCYPR-OH (Cpd. 136)
(SEQ ID NO. 136)
H-P[Nle]E[Nle]RCSLSVECKQKCLAAIGSIFGKC[Nle]NKKCKCYPR-OH (Cpd. 137)
(SEQ ID NO. 137)
H-P[Nle]E[Nle]RCSAPVECKQKCLAAIGSIFGKC[Nle]NKKCKCYPR-OH (Cpd. 138)
(SEQ ID NO. 138)
H-P[Nle]E[Nle]RCSASPECKQKCLAAIGSIFGKC[Nle]NKKCKCYPR-OH (Cpd. 139)
(SEQ ID NO. 139)
H-P[Nle]E[Nle]RCSASQECKQKCLAAIGSIFGKC[Nle]NKKCKCYPR-OH (Cpd. 140)
(SEQ ID NO. 140)
H-P[Nle]E[Nle]RCSASVECLQKCLAAIGSIFGKC[Nle]NKKCKCYPR-OH (Cpd. 141)
(SEQ ID NO. 141)
H-P[Nle]E[Nle]RCSASVECKQPCLAAIGSIFGKC[Nle]NKKCKCYPR-OH (Cpd. 142)
(SEQ ID NO. 142)
H-P[Nle]E[Nle]RCEASVECKQKCLAAIGSIFGKC[Nle]NKKCKCYPR-OH (Cpd. 143)
(SEQ ID NO. 143)
H-P[Nle]E[Nle]RCFASVECKQKCLAAIGSIFGKC[Nle]NKKCKCYPR-OH (Cpd. 144)
(SEQ ID NO. 144)
H-P[Nle]E[Nle]RCSYSVECKQKCLAAIGSIFGKC[Nle]NKKCKCYPR-OH (Cpd. 145)
(SEQ ID NO. 145)
H-P[Nle]E[Nle]RCSAFVECKQKCLAAIGSIFGKC[Nle]NKKCKCYPR-OH

In an embodiment, the ion channel blocker of the invention is:

(Cpd. 97)
(SEQ ID NO. 97)
H-P[Nle]E[Nle]RCSASVECKQKCLAAIGSIFGKC[Nle]
NKKCKCYPR-OH.

In some embodiments, the ion channel blocker is not:

(Cpd. 1)
(SEQ ID NO. 1)
H-QMDMRCSASVECKQKCLKAIGSIFGKCMNKKCKCYPR-OH
or (Cpd. 2)
(SEQ ID NO. 2)
H-QMDMRCSASVECKQKCLKAIGRGFGKCMNKKCKCYPR-OH.

The invention further provides a nucleic acid encoding an ion channel blocker, a Kv1.3 inhibitor, or a peptide $Z^1$—X—$Z^2$ as described.

The invention also provides an expression vector comprising a nucleic acid of the invention.

The invention further comprises a host cell comprising a nucleic acid or an expression vector of the invention, and capable of expressing an ion channel blocker, a Kv1.3 inhibitor, or a peptide $Z^1$—X—$Z^2$ as described. The host cell may be capable of secreting the ion channel blocker, a Kv1.3 inhibitor, or a peptide $Z^1$—X—$Z^2$ as described.

The invention further provides a method of synthesising an ion channel blocker of the invention, the method comprising:
(a) synthesising the ion channel blocker by means of solid-phase or liquid-phase peptide synthesis methodology and recovering the peptide thus obtained;
(b) expressing the ion channel blocker from a nucleic acid construct that encodes the ion channel blocker and recovering the expression product; or
(c) expressing a precursor peptide from a nucleic acid construct that encodes the precursor peptide sequence, recovering the expression product, and modifying the precursor peptide to yield the ion channel blocker.

The invention further provides a pharmaceutical composition comprising an ion channel blocker of the invention or a pharmaceutically acceptable salt thereof, in admixture with a pharmaceutically acceptable carrier.

The invention further provides an ion channel blocker of the invention or a pharmaceutically acceptable salt thereof for use in a method of medical treatment.

The invention further provides an ion channel blocker of the invention or a pharmaceutically acceptable salt thereof for use in a method of inhibiting or reducing inflammation, especially in the treatment of an inflammatory condition or disorder, including autoimmune disorders.

An inflammatory condition or disorder may be any condition or disorder in which reduction of inflammation is desirable, e.g. where inflammation contributes to symptoms or pathogenesis.

Such conditions include autoimmune diseases, allergy and hypersensitivity, allograft rejection and graft versus host disease.

Specific conditions include hay fever, asthma, anaphylaxis, allergic rhinitis, urticaria, eczema, alopecia areata, dermatomyositis, inclusion body myositis, polymyositis, ankylosing spondylitis, vasculitis, arthritis (including rheumatoid arthritis, osteoarthritis, psoriatic arthritis), Sjogren's syndrome, systemic lupus erythematosus (SLE, or simply "lupus"), and uveitis, inflammatory fibrosis (e.g. scleroderma, lung fibrosis, cirrhosis), chronic obstructive pulmonary disease (COPD), hepatitis, chronic inflammatory demyelinating polyneuropathy, inflammatory bowel disease, colitis (including Crohn's disease and ulcerative colitis), erythema, thyroiditis, psoriasis, atopic dermatitis, allergic contact dermatitis, scleroderma, glomerulonephritis, inflammatory bone resorption, multiple sclerosis, type 1 diabetes, transplant rejection and graft-versus-host disease.

The invention further provides an ion channel blocker of the invention or a pharmaceutically acceptable salt thereof for use in a method of inhibiting weight gain, promoting weight loss, reducing excess body weight or treating obesity (e.g. by control of appetite, feeding, food intake, calorie intake, and/or energy expenditure), or in the treatment of obesity linked inflammation, obesity linked gallbladder disease or obesity induced sleep apnoea.

An effect on body weight may be therapeutic or cosmetic.

The invention further provides an ion channel blocker of the invention or a pharmaceutically acceptable salt thereof for use in treatment of a condition caused by or associated with impaired glucose control, such as metabolic syndrome, insulin resistance, glucose intolerance, pre-diabetes, increased fasting glucose or type 2 diabetes.

The invention further provides an ion channel blocker of the invention or a pharmaceutically acceptable salt thereof for use in treatment of a smooth muscle proliferative disorder such as restenosis, e.g. in patients following vascular surgery (e.g. angioplasty).

The invention further provides an ion channel blocker of the invention or a pharmaceutically acceptable salt thereof for use in the treatment of a neuroinflammatory or neurodegenerative disorder, such as Alzheimer's disease, multiple sclerosis (MS), Parkinson's disease or amyotrophic lateral sclerosis (ALS) (e.g. following viral infection).

The invention further provides an ion channel blocker of the invention or a pharmaceutically acceptable salt thereof for use in treatment of cancer, e.g. breast cancer, prostate cancer or lymphoma, such as non-Hodgkin lymphoma (NHL). NHL includes T-cell NHL and B-cell NHL.

Forms of B-cell NHL include diffuse large B-cell lymphoma, follicular lymphoma, Burkitt lymphoma, immunoblastic large cell lymphoma, precursor B-lymphoblastic lymphoma and mantle cell lymphoma. Forms of T-cell NHL include mycosis fungoides, anaplastic large cell lymphoma, peripheral T-cell lymphoma, precursor T-lymphoblastic lymphoma, and Sézary syndrome.

The invention further provides use of an ion channel blocker of the invention or a pharmaceutically acceptable salt thereof in the preparation of a medicament for inhibiting or reducing inflammation, especially in the treatment of an inflammatory condition or disorder, including autoimmune disorders. Further details of such conditions are set out above.

The invention further provides use of an ion channel blocker of the invention or a pharmaceutically acceptable salt thereof in the preparation of a medicament for use in inhibiting weight gain, promoting weight loss, reducing excess body weight or treating obesity (e.g. by control of appetite, feeding, food intake, calorie intake, and/or energy expenditure), or in the treatment of obesity linked inflammation, obesity linked gallbladder disease or obesity induced sleep apnoea.

The invention further provides use of an ion channel blocker of the invention or a pharmaceutically acceptable salt thereof in the preparation of a medicament for treatment of a condition caused by or associated with impaired glucose control, such as metabolic syndrome, insulin resistance, glucose intolerance, pre-diabetes, increased fasting glucose or type 2 diabetes.

The invention further provides use of an ion channel blocker of the invention or a pharmaceutically acceptable salt thereof in the preparation of a medicament for treatment of a smooth muscle proliferative disorder such as restenosis, e.g. in patients following vascular surgery (e.g. angioplasty).

The invention further provides use of an ion channel blocker of the invention or a pharmaceutically acceptable salt thereof in the preparation of a medicament for treatment of a neuroinflammatory or neurodegenerative disorder, such as Alzheimer's disease, multiple sclerosis (MS), Parkinson's disease or amyotrophic lateral sclerosis (ALS) (e.g. following viral infection).

The invention further provides use of an ion channel blocker of the invention or a pharmaceutically acceptable salt thereof in the preparation of a medicament for treatment of cancer, e.g. breast cancer, prostate cancer or lymphoma, such as non-Hodgkin lymphoma (NHL).

The invention further provides a method of inhibiting or reducing inflammation (especially in the treatment of an inflammatory condition or disorder, including autoimmune disorders) comprising administering an ion channel blocker of the invention or a pharmaceutically acceptable salt thereof to a subject in need thereof. Further details of such conditions are set out above.

The invention further provides a method of inhibiting weight gain, promoting weight loss, reducing excess body weight or treating obesity (e.g. by control of appetite, feeding, food intake, calorie intake, and/or energy expenditure), or treating obesity linked inflammation, obesity linked gallbladder disease or obesity induced sleep apnea, comprising administering an ion channel blocker of the invention or a pharmaceutically acceptable salt thereof to a subject in need thereof.

The invention further provides a method of treating a condition caused by or associated with impaired glucose control, such as metabolic syndrome, insulin resistance, glucose intolerance, pre-diabetes, increased fasting glucose or type 2 diabetes, comprising administering an ion channel blocker of the invention or a pharmaceutically acceptable salt thereof to a subject in need thereof.

The invention further provides a method of treating a smooth muscle proliferative disorder such as restenosis, e.g. in patients following vascular surgery (e.g. angioplasty), comprising administering an ion channel blocker of the invention or a pharmaceutically acceptable salt thereof to a subject in need thereof.

The invention further provides a method of treating a neuroinflammatory or neurodegenerative disorder, such as Alzheimer's disease, multiple sclerosis (MS), Parkinson's disease or amyotrophic lateral sclerosis (ALS) (e.g. following viral infection), comprising administering an ion channel blocker of the invention or a pharmaceutically acceptable salt thereof to a subject in need thereof.

The invention further provides a method of treating cancer, e.g. breast cancer, prostate cancer or lymphoma, such as non-Hodgkin lymphoma, comprising administering an ion channel blocker of the invention or a pharmaceutically acceptable salt thereof to a subject in need thereof.

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All patents, published patent applications and non-patent publications referred to in this application are specifically incorporated by reference herein. In case of conflict, the present specification, including its specific definitions, will control.

Each embodiment of the invention described herein may be taken alone or in combination with one or more other embodiments of the invention.

Unless specified otherwise, the following definitions are provided for specific terms which are used in the present written description.

Throughout this specification, the word "comprise", and grammatical variants thereof, such as "comprises" or "comprising", will be understood to imply the inclusion of a stated integer or component, or group of integers or components, but not the exclusion of any other integer or component, or group of integers or components.

The singular forms "a," "an," and "the" include the plurals unless the context clearly dictates otherwise.

The term "including" is used to mean "including but not limited to". "Including" and "including but not limited to" may be used interchangeably.

The terms "patient", "subject" and "individual" may be used interchangeably. A subject may be a mammal, including a human or a non-human mammal, such as a non-human primate (e.g. ape, Old World monkey or New World monkey), livestock animal (e.g. bovine or porcine), companion animal (e.g. canine or feline) or laboratory animal such as a rodent (e.g. mouse or rat).

Throughout the present description and claims the conventional three-letter and one-letter codes for naturally occurring amino acids are used, i.e.

A (Ala), G (Gly), L (Leu), I (Ile), V (Val), F (Phe), W (Trp), S (Ser), T (Thr), Y (Tyr), N (Asn), Q (Gln), D (Asp), E (Glu), K (Lys), R (Arg), H (His), M (Met), C (Cys) and P (Pro);

as well as generally accepted codes for other α-amino acids, such as norleucine (Nle), sarcosine (Sar), α-aminoisobutyric acid (Aib), 2,3-diaminopropanoic acid (Dap), 2,4-diaminobutanoic acid (Dab), 2,5-diaminopentanoic acid (ornithine; Orn) alpha-aminobutyric acid (Abu, also known as homo-alanine), hK, hLys or homo-Lys (homo-lysine), hQ, hGln or homo-Gln (homo-glutamine, also known as 6-oxolysine, carbarmoylnorvaline, 6-amino-6-oxonorleucine or 5-(aminocarbonyl)norvaline), F(4-F) (4-fluoro-phenylalanine), F(4-NH$_2$) (4-amino-phenylalanine), F(4-NO$_2$) (4-nitro-phenylalanine), F(4-CH$_3$) (4-methyl-phenylalanine).

The designation [2-Amino-5-carboxypentanoyl] indicates a peptide residue of 2-amino-5-carboxypentanoic acid:

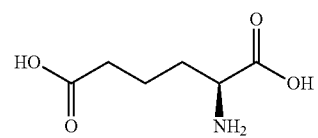 [SMILES: N[C@@H](CCCC(=O)O)C(=O)O]

which thus has a side chain similar to that of glutamic acid, but with an additional methylene group.

Such other α-amino acids may be shown in square brackets "[ ]" (e.g. "[Nle]") when used in a general formula or sequence in the present specification, especially when the rest of the formula or sequence is shown using the single letter code. The 20 "naturally occurring" amino acids listed above are those which are encoded by the standard genetic code, and may also be referred to as "proteinogenic" amino acids.

Unless otherwise specified, amino acid residues in peptides of the invention are of the L-configuration. However, D-configuration amino acids may be incorporated. In the present context, an amino acid code written with a small letter represents the D-configuration of said amino acid, e.g. "k" represents the D-configuration of lysine (K).

A "H" (or "Hy-") moiety at the N-terminus of the sequence in question indicates a hydrogen atom [i.e. $R^1$=hydrogen], corresponding to the presence of a free primary or secondary amino group at the N-terminus, while an "—OH" or an "—NH$_2$" moiety at the C-terminus of the sequence [i.e. $R^2$=OH or NH$_2$] indicates the presence of a carboxy (COOH) group or an amido (CONH$_2$) group at the C-terminus of the molecule. A "CH$_2$OH" moiety at the C-terminus [i.e. $R^2$=CH$_2$OH] indicates the presence of a hydroxyl group linked to an alkyl group at the C-terminus of the molecule. The CH$_2$OH moiety can be comprised in (4-amino-5-hydroxypentyl)guanidine or 4-amino-5-hydroxypentanamide. Designations of other $R^1$ and $R^2$ groups should be interpreted accordingly.

KV1.3 Blockers

The term Kv1.3 is used to refer to potassium voltage-gated channel subfamily A member 3, also referred to as KCNA3, HPCN3, HGK5, HuKIII and HLK3. "Subfamily A" may also be referred to as "shaker-related subfamily". The human amino acid sequence is provided under UniProt accession number P22001, version P22001.3 (Q5VWN2).

The Kv1.3 channel is expressed on T and B lymphocytes and has been implicated in T cell activation. A number of groups are pursuing development of Kv1.3 blockers for the inhibition of immune responses as well as for various other indications. However, the Kv1.3 channel is part of a complex family of related ion channels, also including the Kv1.1, Kv1.2 and Kv1.6 channels, which have different physiological roles. Consequently it is desirable for Kv1.3 inhibitors to be as selective as possible for Kv1.3 in preference to other ion channels, especially other voltage-gated potassium channels, such as Kv1.1, Kv1.2, Kv1.4, Kv1.5, Kv1.6, Kv1.7 and Kv1.8.

The term "ion channel blocker" is used simply to denote a compound having inhibitor (or blocking) activity against an ion channel, i.e. capable of inhibiting or eliminating ion flow through the respective ion channel, typically by binding to the ion channel. Similarly, the terms "Kv1.3 inhibitor" and "Kv1.3 inhibitor component" refer to a peptide capable of inhibiting or eliminating ion flow through a Kv1.3 ion channel, typically by binding to the Kv1.3 channel. However, the terms "blocker" and "inhibitor" should not be taken to imply any particular mechanism of action, or any particular mode of interaction with the ion channel itself.

The ion channel blocker (and the Kv1.3 inhibitor component in isolation) of the invention has inhibitor or blocker activity at the Kv1.3 ion channel, i.e. it is capable of inhibiting ion flow through the Kv1.3 channel.

$IC_{50}$ values may be used as a measure of inhibitor (or blocker) activity or potency. An $IC_{50}$ value is a measure of the concentration of an inhibitor required to achieve half of that compound's maximal inhibition of ion channel activity in a given assay. A compound which has a lower $IC_{50}$ at a particular ion channel than a reference compound can be considered to be a more active inhibitor, or a more potent inhibitor, than the reference compound. The terms "activity" and "potency" are used interchangeably.

$IC_{50}$ values may be determined using any appropriate assay, such as fluorescence-based assays measuring ion flux (e.g. thallium ion flux) and patch clamp assays. They may be performed as described in the Examples below. Patch clamp assays may be preferred, e.g. using the QPatch® system.

The ion channel blocker (or Kv1.3 inhibitor) of the invention may have an $IC_{50}$ below 10 nM, but ideally the $IC_{50}$ is below 5 nM, below 2 nM or below 1 nM. In some cases it may be as low as 0.5 nM, 0.1 nM, or even lower.

Ion channel blockers of the invention may include the compounds 1-5, 7, 11-42, 44-48, 50-53, 55-60, 62-68, 70-73, 75-81, 83-88, 90-98, 101, 104-108, 116, 122, 129, 131, 132, 134 and 137 as described herein. These compounds are shown in Example 2 herein to have an $IC_{50}$ of 0.3 nM or less.

Ion channel blockers of the invention may include the compounds 7, 14-35, 37, 39, 40-48, 50-53, 55-60, 62-68, 70-73, 75-80, 83-97, 90, 91, 93-98, 101, 104-108, 116, 129 and 131 as described herein. These compounds are shown in Example 2 herein to have an $IC_{50}$ of 0.2 nM or less.

Ion channel blockers of the invention may include the compounds 7, 15-17, 19-28, 30-35, 37, 39-42, 44, 46-48, 51-53, 55-60, 62-67, 70, 71, 73, 75-80, 83-85, 87, 91, 93, 96-98, 104, 106, 107, 108 and 129 as described herein. These compounds are shown in Example 2 herein to have an $IC_{50}$ of 0.15 nM or less.

Ion channel blockers of the invention may include the compounds 1, 3, 17, 19, 21, 23, 26-33, 37, 41-43, 46-49, 52, 62, 63, 66-68, 70-73, 75, 76, 78, 82-84, 87, 91, 94, 97-102, 105-108, 115 and 116 as described herein. These compounds are shown in Example 5 herein to have an $IC_{50}$ of 1 nM or less for inhibiting activation of T cells in rat whole blood.

The ion channel blockers of the invention are selective for Kv1.3. In an embodiment the ion channel blockers of the invention are selective over Kv1.1, Kv1.2, Kv1.4, Kv1.5, Kv1.6, Kv1.7 and Kv1.8. In particular, the ion channel blockers of the invention are selective for Kv1.3 over one or more of Kv1.1, Kv1.2 and Kv1.6.

For example, they may be:
selective for Kv1.3 over Kv1.1;
selective for Kv1.3 over Kv1.2;
selective for Kv1.3 over Kv1.6;
selective for Kv1.3 over Kv1.1 and Kv1.2;
selective for Kv1.3 over Kv1.1 and Kv1.6;
selective for Kv1.3 over Kv1.2 and Kv1.6; or
selective for Kv1.3 over Kv1.1, Kv1.2 and Kv1.6.

Typically, the ion channel blockers are selective for Kv1.3 over Kv1.1.

They may additionally be selective for Kv1.3 over Kv1.2 and/or Kv1.6.

By "selective" in this context is meant that the ion channel blockers have higher inhibitor activity against Kv1.3 than against the respective ones of Kv1.1, Kv1.2 and Kv1.6. Thus, their $IC_{50}$ against Kv1.3 is typically lower than against the respective other ion channel or channels.

Selectivity for Kv1.3 over another ion channel X may therefore be expressed as a ratio of the respective $IC_{50}$ values, e.g. as $IC_{50}[X]/IC_{50}[Kv1.3]$.

The ion channel blockers of the invention may therefore have a selectivity for Kv1.3 over Kv1.1 of at least 10, at least 100, at least 1000, or at least 10000, and may be up to 100000 or even higher. Typically, they have a selectivity for Kv1.3 over Kv1.1 of at least 100, or at least 1000.

Ion channel blockers of the invention may include compounds 1-3, 5, 8, 12, 16-23, 25-31, 34-37, 40-42, 45-49, 52-54, 56, 58, 62, 63, 70, 71, 76, 79, 83, 94-98, 101, 103-108 and 117 as described herein. These compounds are shown in Example 3 herein to have selectivity for Kv1.3 over Kv1.1 of at least 1000.

Ion channel blockers of the invention may include compounds 3, 12, 16, 18-22, 25-28, 30, 31, 35, 37, 40-42, 52, 53, 62, 70, 71, 76, 79, 94, 95, 98 and 105 as described herein. These compounds are shown in Example 3 herein to have selectivity for Kv1.3 over Kv1.1 of at least 10000.

The ion channel blockers of the invention may therefore have a selectivity for Kv1.3 over Kv1.2 of at least 10, at least 100, at least 1000, or at least 10000, and may be up to 100000 or even higher. Typically, they have a selectivity for Kv1.3 over Kv1.2 of at least 10, and preferably at least 50 or at least 100 or at least 1000.

Ion channel blockers of the invention may include compounds 1-3, 5, 8, 16-23, 25-31, 34-37, 40-42, 45-49, 52-54, 56, 58, 62, 63, 70, 71, 76, 79, 83, 94-98, 101, 103-108 and 117 as described herein. These compounds are shown in Example 3 herein to have selectivity for Kv1.3 over Kv1.2 of at least 50.

Ion channel blockers of the invention may include compounds 1, 3, 5, 8, 12, 18, 25, 29, 30, 36, 37, 41, 46-48, 52, 62, 70, 71, 79, 83, 94-98, 101, 103-106 and 117 as described herein. These compounds are shown in Example 3 herein to have selectivity for Kv1.3 over Kv1.2 of at least 700.

Ion channel blockers of the invention may include compounds 1, 3, 12, 18, 29, 30, 36, 37, 41, 47, 48, 62, 70, 71, 79, 94-98, 101 and 103-105 as described herein.

These compounds are shown in Example 3 herein to have selectivity for Kv1.3 over Kv1.2 of at least 1000.

The ion channel blockers of the invention may therefore have a selectivity for Kv1.3 over Kv1.6 of at least 10, at least 100, at least 1000, or at least 10000, and may be up to 100000 or even higher. Typically, they have a selectivity for Kv1.3 over Kv1.6 of at least 100, or at least 400, or at least 1000.

Ion channel blockers of the invention may include compounds 1, 2, 3, 5, 8, 12, 16-23, 25-31, 34-37, 40-42, 45-49, 52-54, 56, 58, 62, 63, 70, 71, 76, 79, 83, 94-98, 101, 103-108 and 117 as described herein. These compounds are shown in Example 3 herein to have selectivity for Kv1.3 over Kv1.6 of at least 400.

Ion channel blockers of the invention may include compounds 3, 12, 16, 18, 20, 22, 26, 30, 31, 37, 41, 52, 53, 70, 71, 76, 79, 94, 95, 98 and 105 as described herein. These compounds are shown in Example 3 herein to have selectivity for Kv1.3 over Kv1.6 of at least 10000.

The ion channel blockers of the invention may have greater selectivity than known ion channel blockers such as ShK, Mokatoxin (Moka1), Vm24, Odk2 or Osk1. Thus the ion channel blockers of the invention may have higher selectivity for Kv1.3 over ion channel X, i.e. $IC_{50}[X]/IC_{50}[Kv1.3]$, which is greater than the selectivity of the comparison molecule. The selectivity of the two ion channel blockers will be determined under the same conditions for each ion channel to enable direct comparison. As mentioned above, any appropriate assays may be used, such as fluorescence-based ion flux assays and patch clamp assays.

The ion channel blockers of the invention may have lower absolute inhibitor activity (i.e. higher $IC_{50}$) than known ion channel blockers (such as Odk2 or Osk1) at any or all of Kv1.1, Kv1.2 and/or Kv1.6. However, it may be acceptable for them to have higher absolute inhibitor activity at any or all of these ion channels, as long as their selectivity for Kv1.3 is higher than that of the comparison compound. Typically, though, the compounds of the invention combine high specificity for Kv1.3 with high potency.

Synthesis and Recombinant Expression

The ion channel blockers described herein may be synthesised by means of solid-phase or liquid-phase peptide synthesis methodology. In this context, reference may be made to WO 98/11125 and, among many others, Fields, G. B. et al., 2002, "Principles and practice of solid-phase peptide synthesis". In: Synthetic Peptides (2nd Edition), and the Examples herein.

Alternatively, the ion channel blockers described herein may be synthesised by recombinant techniques, or by a combination of recombinant techniques and peptide chemistry.

For example, an ion channel blocker peptide may be synthesised by a method which comprises (a) synthesising the peptide by means of solid-phase or liquid-phase peptide synthesis methodology and recovering the peptide thus obtained;
(b) expressing the peptide from a nucleic acid construct that encodes the peptide and recovering the expression product; or
(c) expressing a precursor peptide from a nucleic acid construct that encodes the precursor peptide sequence, recovering the expression product, and modifying the precursor peptide to yield an ion channel blocker of the invention.

The precursor peptide may be modified by introduction of one or more non-proteinogenic amino acids (e.g. Nle), introduction of the appropriate terminal groups $R^1$ and $R^2$, etc.

Expression of the peptide or precursor peptide from a nucleic acid encoding the peptide or precursor peptide may be performed in a cell or a cell-free expression system comprising such a nucleic acid. Such expression typically requires that the peptide or precursor peptide is composed entirely of proteinogenic amino acids (i.e. the 20 amino acids encoded by the standard genetic code.)

For recombinant expression, the nucleic acid fragments encoding the precursor peptide will normally be inserted in suitable vectors to form cloning or expression vectors. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment, optionally a nucleic acid sequence encoding a leader peptide enabling secretion (to the extracellular phase or, where applicable, into the periplasm), the nucleic acid fragment encoding the precursor peptide, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the peptide or precursor peptide. Such transformed cells can be cultured cells or cell lines used for propagation of the nucleic acid fragments and vectors, and/or used for recombinant production of the precursor peptides.

Preferred transformed cells are micro-organisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment can be used for small-scale or large-scale preparation of the peptides of the invention.

When producing the peptide or precursor peptide by means of transformed cells, it is convenient, although far from essential, that the expression product is secreted into the culture medium.

Therapeutic Indications

As discussed above, blockers of Kv1.3 have been shown to inhibit proliferation of activated T cells and to have a beneficial effect in various experimental models of disease. Without wishing to be bound by theory, it is believed that cellular efflux of potassium via the Kv1.3 channel is required to sustain calcium influx required for T-cell activation.

Kv1.3 is overexpressed in Gad5/insulin-specific T cells from patients with new onset type 1 diabetes, in myelin-specific T cells from MS patients and in T cells from the synovium of rheumatoid arthritis patients (Beeton et al., Proc Natl Acad Sci USA 103:17414-9, 2006), in breast cancer specimens (Abdul et al., Anticancer Res 23:3347, 2003) and prostate cancer cell lines (Fraser et al., Pflugers Arch 446:559, 2003).

Positive outcomes in animal models with Kv1.3 blockers have been described in hypersensitivity models to ovalbumin and tetanus toxoid (Beeton et al., Mol Pharmacol 67:1369, 2005; Koo et al., Clin Immunol 197:99, 1999), models for multiple sclerosis such as rat adoptive-transfer experimental autoimmune encephalomyelitis (AT-EAE) model (Beeton et al., Proc Natl Acad Sci USA 103:17414-9, 2006), inflammatory bone resorption model (Valverde et al., J Bone Mineral Res 19:155, 2004), models for arthritis (Beeton et al., Proc Natl Acad Sci 103: 17414, 2006; Tarcha et al., J. Pharmacol. Exp. Ther. 342: 642, 2012) and obesity, diabetes and metabolic disorders (Xu et al., Hum Mol Genet 12:551, 2003; Xu et al., Proc Natl Acad Sci 101: 3112, 2004).

Topical application of Kv1.3 blockers has been proposed for the treatment of skin and mucosal inflammation.

Thus, the ion channel blockers described in this specification have considerable potential for use in inhibiting or reducing inflammation, especially in the treatment of an inflammatory condition or disorder, including autoimmune disorders.

An inflammatory condition or disorder may be any condition or disorder in which reduction of inflammation is desirable, e.g. where inflammation contributes to symptoms or pathogenesis.

Such conditions include autoimmune disorders, allergy and hypersensitivity, allograft rejection and graft versus host disease.

More specifically, conditions include hay fever, asthma, anaphylaxis, allergic rhinitis, urticaria, eczema, alopecia areata, dermatomyositis, inclusion body myositis, polymyositis, ankylosing spondylitis, vasculitis, arthritis (including rheumatoid arthritis, osteoarthritis, psoriatic arthritis), Sjogren's syndrome, systemic lupus erythematosus (SLE, or simply "lupus"), and uveitis, inflammatory fibrosis (e.g. scleroderma, lung fibrosis, cirrhosis), chronic obstructive pulmonary disease (COPD), hepatitis, chronic inflammatory demyelinating polyneuropathy, inflammatory bowel disease, colitis (including Crohn's disease and ulcerative colitis), erythema, thyroiditis, psoriasis, atopic dermatitis, allergic contact dermatitis, scleroderma, glomerulonephritis, inflammatory bone resorption, multiple sclerosis, type 1 diabetes, transplant rejection and graft-versus-host disease.

Blockers of Kv1.3 may also have beneficial metabolic effects, e.g. in relation to energy homeostasis, body weight regulation, and glucose control.

The ion channel blockers described here may therefore be used for inhibiting weight gain, promoting weight loss, reducing excess body weight or treating obesity (e.g. by control of appetite, feeding, food intake, calorie intake, and/or energy expenditure), as well as in the treatment of associated disorders and health conditions including obesity linked inflammation, obesity linked gallbladder disease and obesity induced sleep apnoea.

An effect on body weight may be therapeutic or cosmetic.

The ion channel blockers may also be used for the treatment of conditions caused by or associated with impaired glucose control, including metabolic syndrome, insulin resistance, glucose intolerance, pre-diabetes, increased fasting glucose and type 2 diabetes. Some of these conditions can be associated with obesity. Their effects on these conditions may be mediated in whole or in part via an effect on body weight, or may be independent thereof.

Kv1.3 is also expressed in proliferating human and mouse smooth muscle cells. Blockers of Kv1.3 may be effective in smooth muscle proliferative disorders such as restenosis, e.g. in patients following vascular surgery (e.g. angioplasty).

Further evidence suggests that Kv1.3 channels are involved in the activation and/or proliferation of many types of cells, including tumor cells (Bielanska et al., Curr. Cancer Drug Targets 9:904-14, 2009), microglia (Khanna et al., Am. J. Physiol. Cell Physiol. 280: C796-806, 2001) and differentiation of neuronal progenitor cells (Wang et al., J. Neurosci. 30:5020-7, 2010). Kv1.3 blockers may therefore be beneficial in the treatment of neuroinflammatory and neurodegenerative disorders such as Alzheimer's disease, multiple sclerosis (MS), Parkinson's disease and amyotrophic lateral sclerosis (ALS) (e.g. following viral infections), and cancers including breast cancer, prostate cancer, and lymphoma, such as non-Hodgkin lymphoma (NHL). Non-Hodgkin lymphomas include T-cell NHL and B-cell NHL. Forms of B-cell NHL include diffuse large B-cell lymphoma, follicular lymphoma, Burkitt lymphoma, immunoblastic large cell lymphoma, precursor B-lymphoblastic lymphoma and mantle cell lymphoma. Forms of T-cell NHL include mycosis fungoides, anaplastic large cell lymphoma, peripheral T-cell lymphoma, precursor T-lymphoblastic lymphoma and Sézary syndrome.

Pharmaceutical Compositions and Administration

An aspect of the present invention relates to a composition comprising an ion channel blocker of the invention, or a salt thereof, together with a carrier, excipient or vehicle. In certain embodiments, the composition is a pharmaceutical composition, any salt is a pharmaceutically acceptable salt, and the carrier is a pharmaceutically acceptable carrier, excipient or vehicle.

Accordingly, the compounds of the present invention, or salts thereof, especially pharmaceutically acceptable salts thereof, may be formulated as compositions or pharmaceutical compositions prepared for storage or administration, and which comprise a therapeutically effective amount of a compound of the invention, or a salt thereof.

Suitable salts formed with bases include metal salts, such as alkali metal or alkaline earth metal salts, for example sodium, potassium or magnesium salts; ammonia salts and organic amine salts, such as those formed with morpholine, thiomorpholine, piperidine, pyrrolidine, a lower mono-, di- or tri-alkylamine (e.g., ethyl-tert-butyl-, diethyl-, diisopropyl-, triethyl-, tributyl- or dimethylpropylamine), or a lower mono-, di- or tri-(hydroxyalkyl)amine (e.g., mono-, di- or triethanolamine). Internal salts may also be formed. Similarly, when a compound of the present invention contains a basic moiety, salts can be formed using organic or inorganic acids. For example, salts can be formed from the following acids: formic, acetic, propionic, butyric, valeric, caproic, oxalic, lactic, citric, tartaric, succinic, fumaric, maleic, malonic, mandelic, malic, phthalic, hydrochloric, hydrobromic, phosphoric, nitric, sulphuric, benzoic, carbonic, uric, methanesulphonic, naphthalenesulphonic, benzenesulphonic, toluenesulphonic, p-toluenesulphonic (i.e. 4-methylbenzene-sulphonic), camphorsulphonic, 2-aminoethanesulphonic, aminomethylphosphonic and trifluoromethanesulphonic acid (the latter also being denoted triflic acid), as well as other known pharmaceutically acceptable acids. Amino acid addition salts can also be formed with amino acids, such as lysine, glycine, or phenylalanine.

In some embodiments, a pharmaceutical composition of the invention is one wherein the compound is in the form of a pharmaceutically acceptable acid addition salt.

As will be apparent to one skilled in the medical art, a "therapeutically effective amount" of a compound or pharmaceutical composition of the present invention will vary depending upon, inter alia, the age, weight and/or gender of the subject (patient) to be treated. Other factors that may be of relevance include the physical characteristics of the specific patient under consideration, the patient's diet, the nature of any concurrent medication, the particular compound(s) employed, the particular mode of administration, the desired pharmacological effect(s) and the particular therapeutic indication. Because these factors and their relationship in determining this amount are well known in the medical arts, the determination of therapeutically effective dosage levels to achieve the desired therapeutic effect will be within the ambit of the skilled person.

As used herein, the term "a therapeutically effective amount" refers to an amount which reduces symptoms of a given condition or pathology, and preferably which normalizes physiological responses in an individual with that condition or pathology.

Reduction of symptoms or normalization of physiological responses can be determined using methods routine in the art and may vary with a given condition or pathology. In one aspect, a therapeutically effective amount of a compound of the invention, or a pharmaceutical composition, is an amount which restores a measurable physiological parameter to substantially the same value (preferably to within 30%, more preferably to within 20%, and still more preferably to within 10% of the value) of the parameter in an individual without the condition or pathology in question.

In one embodiment of the invention, administration of a compound or pharmaceutical composition of the present invention is commenced at lower dosage levels, with dosage levels being increased until the desired effect of preventing/treating the relevant medical indication is achieved. This would define a therapeutically effective amount. For the compounds of the present invention, alone or as part of a pharmaceutical composition, such human doses of the active compound may be between about 0.01 pmol/kg and 500 µmol/kg body weight, between about 0.01 pmol/kg and 300 µmol/kg body weight, between 0.01 pmol/kg and 100 µmol/kg body weight, between 0.1 pmol/kg and 50 µmol/kg body weight, between 1 pmol/kg and 10 µmol/kg body weight, between 5 pmol/kg and 5 µmol/kg body weight, between 10 pmol/kg and 1 µmol/kg body weight, between 50 pmol/kg and 0.1 µmol/kg body weight, between 100 pmol/kg and 0.01 µmol/kg body weight, between 0.001 µmol/kg and 0.5 µmol/kg body weight, between 0.05 µmol/kg and 0.1 µmol/kg body weight.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

EXAMPLES

Example 1: General Peptide Synthesis

List of abbreviations and suppliers are provided in the table below

| List of abbreviations and suppliers | | | |
|---|---|---|---|
| | Abbreviation | Name | Brand/Supplier |
| Resins | | | |
| | | TentaGel ™ PHB AA(Proct)-Fmoc | Rapp Polymere |
| | | TentaGel ™ SRAM | Rapp Polymere |
| Amino acids | | | |
| | | Pseudoprolines (E.g. QT, AT, FS) | Jupiter Bioscience Ltd. |
| | | Fmoc-L-AA-OH | Senn Chemicals AG |
| Coupling reagents | | | |
| | COMU | (1-Cyano-2-ethoxy-2-oxoethylidenaminooxy)dimethylamino-morpholino-carbenium hexafluorophosphate | Watson International Ltd. |
| | DIC | Diisopropylcarbodiimide | Fluka/Sigma Aldrich Co. |
| | HATU | N-[(dimethylamino)-1 H-1,2,3-triazol[4,5-b]pyridine-1-ylmethylene]-N-methylmethanaminium hexafluorophosphate N-oxide | ChemPep Inc. |
| | HOBt | Hydroxybenzotriazole | Sigma-Aldrich Co. |
| Solvents reagents | | | |
| | Boc₂O | Di-tert-butyl pyrocarbonate | Advanced ChemTech |
| | DCM | Dichloromethane | Prolabo (VWR) |
| | DIPEA | Diisopropylethylamine | Fluka/Sigma Aldrich Co. |

-continued

| Abbreviation | Name | Brand/Supplier |
|---|---|---|
| DMF | N,N-dimethylformamide | Taminco |
| DODT | 3,6-dioxa-1,8-octanedithiol | Sigma-Aldrich Co. |
| Et$_2$O | Diethyl ether | Prolabo (VWR) |
| EtOH | Ethanol | CCS Healthcare AB |
| | Formic acid (HPLC) | Sigma-Aldrich Co. |
| H$_2$O | Water, Milli-Q water | Millipore |
| MeCN | Acetonitrile (HPLC) | Sigma-Aldrich Co. |
| NMP | N-methylpyrrolidone | Sigma-Aldrich Co. |
| | Piperidine | Jubliant Life Sciences Ltd. |
| TFA | Trifluoroacetic acid (HPLC) | Chemicals Raw Materials Ltd. |
| TIS | Triisopropylsilane | Sigma-Aldrich Co. |
| MeOH | Methanol | Sigma-Aldrich Co. |

Apparatus and Synthetic Strategy

Peptides were synthesized batchwise on a peptide synthesiser, such as a CEM Liberty Peptide Synthesizer or a Symphony X Synthesizer, according to solid phase peptide synthetic procedures using 9-fluorenylmethyloxycarbonyl (Fmoc) as N-α-amino protecting group and suitable common protection groups for side-chain functionalities.

As polymeric support based resins, such as e.g. TentaGel™, was used. The synthesizer was loaded with resin that prior to usage was swelled in DMF.

Coupling

CEM Liberty Peptide Synthesizer

A solution of Fmoc-protected amino acid (4 equiv.) was added to the resin together with a coupling reagent solution (4 equiv.) and a solution of base (8 equiv.). The mixture was either heated by the microwave unit to 70-75° C. and coupled for 5 minutes or coupled with no heat for 60 minutes. During the coupling nitrogen was bubbled through the mixture.

Symphony X Synthesizer

The coupling solutions were transferred to the reaction vessels in the following order: amino acid (4 equiv.), HATU (4 equiv.) and DIPEA (8 equiv.). The coupling time was 10 min at room temperature (RT) unless otherwise stated. The resin was washed with DMF (5×0.5 min). In case of repeated couplings the coupling time was in all cases 45 min at RT.

Deprotection

CEM Liberty Peptide Synthesizer

The Fmoc group was deprotected using piperidine in DMF or other suitable solvents. The deprotection solution was added to the reaction vessel and the mixture was heated for 30 sec. reaching approx. 40° C. The reaction vessel was drained and fresh deprotection solution was added and subsequently heated to 70-75° C. for 3 min. After draining the reaction vessel the resin was washed with DMF or other suitable solvents.

Symphony X Synthesizer

Fmoc deprotection was performed for 2.5 minutes using 40% piperidine in DMF and repeated using the same conditions. The resin was washed with DMF (5×0.5 min).

Cleavage

The dried peptide resin was treated with TFA and suitable scavengers for approximately 2 hours. The volume of the filtrate was reduced and the crude peptide was precipitated after addition of diethylether. The crude peptide precipitate was washed several times with diethylether and finally dried.

HPLC Purification of the Crude Peptide

The crude peptide was purified by preparative reverse phase HPLC using a conventional HPLC apparatus, such as a Gilson GX-281 with 331/332 pump combination', for binary gradient application equipped with a column, such as 5×25 cm Gemini NX 5u C18 110A column, and a fraction collector using a flow 20-40 ml/min with a suitable gradient of buffer A (0.1% Formic acid, aq.) or A (0.1% TFA, aq.) and buffer B (0.1% Formic acid, 90% MeCN, aq.) or B (0.1% TFA, 90% MeCN, aq.). Fractions were analyzed by analytical HPLC and MS and selected fractions were pooled and lyophilized. The final product was characterized by HPLC and MS.

Disulphide Formation

The crude or partially purified linear peptide with six cysteines was dissolved in a buffer such as sodium hydrogen carbonate (NaHCO$_3$) or ammonium acetate (NH$_4$Ac) to give a final concentration of approximate 0.1 mg/ml or 25 µM. The pH of the buffer was adjusted to pH 8.0 and the solution was stirred at room temperature under magnetic stirring and open access to the atmosphere. The progress of the reaction was determined by HPLC and was usually evaluated to be complete overnight. The solution was quenched by reducing the pH of the solution by an organic acid such as acetic acid or trifluoroacetic acid (pH<4). The solution was filtered and loaded directly on a prep-HPLC column for purification.

Analytical HPLC

Final purities were determined by analytic HPLC (Agilent 1100/1200 series) equipped with auto sampler, degasser, 20 µl flow cell and Chromeleon software. The HPLC was operated with a flow of 1.2 ml/min at 40° C. using an analytical column, such as Kinetex 2.6 µm XB-C18 100A 100×4.6 mm column. The compound was detected and quantified at 215 nm. Buffers A (0.1% TFA, aq.) and buffer B (0.1% TFA, 90% MeCN, aq.).

Mass Spectroscopy

Final MS analysis was performed on a conventional mass spectrometer, e.g. Waters Xevo G2 Tof, equipped with electrospray detector with lock-mass calibration and MassLynx software. It was operated in positive mode using direct injection and a cone voltage of 15V (1 TOF), 30 V (2 TOF) or 45 V (3 TOF) as specified on the chromatogram. Precision was 5 ppm with a typical resolution of 15,000-20,000.

Compounds synthesized are shown in Table 1.

TABLE 1

| Cmpnd No. | Sequence |
|---|---|
| 1 | H-QMDMRCSASVECKQKCLKAIGSIFGKCMNKKCKCYPR-OH (SEQ ID NO. 1) |
| 2 | H-QMDMRCSASVECKQKCLKAIGRGFGKCMNKKCKCYPR-OH (SEQ ID NO. 2) |

TABLE 1-continued

| Cmpnd No. | Sequence |
|---|---|
| 3 | H-NMDMRCSASVECKQKCLKAIGSIFGKCMNKKCKCYPR-OH (SEQ ID NO. 3) |
| 4 | H-NMDMRCSASVECKQKCLKAIGRGFGKCMNKKCKCYPR-OH (SEQ ID NO. 4) |
| 5 | H-MDMRCSASVECKQKCLKAIGSIFGKCMNKKCKCYPR-OH (SEQ ID NO. 5) |
| 6 | H-DMRCSASVECKQKCLKAIGSIFGKCMNKKCKCYPR-OH (SEQ ID NO. 6) |
| 7 | H-NMDMRCSASVECKQKCLKAIGSIFGKCMNKKCKCYPR-NH$_2$ (SEQ ID NO. 7) |
| 8 | H-NIDMRCSASVECKQKCLKAIGSIFGKCMNKKCKCYPR-OH (SEQ ID NO. 8) |
| 9 | H-NMDVRCSASVECKQKCLKAIGSIFGKCMNKKCKCYPR-OH (SEQ ID NO. 9) |
| 10 | H-NMDMRCSASVECKQKCKDAIGSIFGKCMNKKCKCYPR-OH (SEQ ID NO. 10) |
| 11 | H-GGNMDMRCSASVECKQKCLKAIGSIFGKCMNKKCKCYPR-OH (SEQ ID NO. 11) |
| 12 | H-NMEMRCSASVECKQKCLKAIGSIFGKCMNKKCKCYPR-OH (SEQ ID NO. 12) |
| 13 | H-SGNMDMRCSASVECKQKCLKAIGSIFGKCMNKKCKCYPR-OH (SEQ ID NO. 13) |
| 14 | H-N[Nle]DMRCSASVECKQKCLKAIGSIFGKCMNKKCKCYPR-NH$_2$ (SEQ ID NO. 14) |
| 15 | H-NMD[Nle]RCSASVECKQKCLKAIGSIFGKCMNKKCKCYPR-NH$_2$ (SEQ ID NO. 15) |
| 16 | H-NMDMRCSASVECKQKCLKAIGSIFGKC[Nle]NKKCKCYPR-NH$_2$ (SEQ ID NO. 16) |
| 17 | H-NMDMRCSASVECKVKCLKAIGSIFGKCMNKKCKCYPR-NH$_2$ (SEQ ID NO. 17) |
| 18 | H-NMDMRCSASVECKQLCLKAIGSIFGKDANKKCKCYPR-NH$_2$ (SEQ ID NO. 18) |
| 19 | H-NMDMRCSASVECKQKCKKAIGSIFGKCMNKKCKCYPR-NH$_2$ (SEQ ID NO. 19) |
| 20 | H-NMDMRCSASVECKQKCLDAIGSIFGKDANKKCKCYPR-NH$_2$ (SEQ ID NO. 20) |
| 21 | H-NMDMRCSASVECKQKCLKAIRSIFGKCMNKKCKCYPR-NH$_2$ (SEQ ID NO. 21) |
| 22 | H-NMDMRCSASVECKQKCLKAIESIFGKDANKKCKCYPR-NH$_2$ (SEQ ID NO. 22) |
| 23 | H-NMDMRCSASVECKQKCLKAIGSIFGKDANKKCKCYPRRRTA-NH$_2$ (SEQ ID NO. 23) |
| 24 | H-NMDMRCSASVECKQKCLKAIGSIFGKCMNKKCKCYPRHRRK-NH$_2$ (SEQ ID NO. 24) |
| 25 | H-NMDMRCKASVECKQKCLKAIGSIFGKDANKKCKCYPR-NH$_2$ (SEQ ID NO. 25) |
| 26 | H-NMDMRCSISVECKQKCLKAIGSIFGKCMNKKCKCYPR-NH$_2$ (SEQ ID NO. 26) |
| 27 | H-NMDMRCSASRECKQKCLKAIGSIFGKCMNKKCKCYPR-NH$_2$ (SEQ ID NO. 27) |

TABLE 1-continued

| Cmpnd No. | Sequence |
|---|---|
| 28 | H-NMDMRCSASVC2CKQKCLKAIGSIFGKCMNKKCKCYPR-NH$_2$ (SEQ ID NO. 28) |
| 29 | H-NMDMRCSASVECLQKCLKAIGSIFGKDANKKCKCYPR-NH$_2$ (SEQ ID NO. 29) |
| 30 | H-NMDMRCSASVECAQKCLKAIGSIFGKDANKKCKCYPR-NH$_2$ (SEQ ID NO. 30) |
| 31 | H-NMDMRCSASVECKEKCLKAIGSIFGKDANKKCKCYPR-NH$_2$ (SEQ ID NO. 31) |
| 32 | H-NMDMRCSASVECKLKQLKAIGSIFGKCMNKKCKCYPR-NH$_2$ (SEQ ID NO. 32) |
| 33 | H-NMDMRCSASVECKQKCLKAIHSIFGKCMNKKCKCYPR-NH$_2$ (SEQ ID NO. 33) |
| 34 | H-NMDMRCSASVECKQKCLKAIGSKFGKDANKKCKCYPR-NH$_2$ (SEQ ID NO. 34) |
| 35 | H-NMDMRCSASVECKQKCLKAIGSRFGKDANKKCKCYPR-NH$_2$ (SEQ ID NO. 35) |
| 36 | H-NMDMRCSASVECKQKCLKAIGSIFGKCMNGKCKCYPR-NH$_2$ (SEQ ID NO. 36) |
| 37 | H-NMDMRCSASVECKQKCLKAIGSIFGKCMNKKCHCYPR-NH$_2$ (SEQ ID NO. 37) |
| 38 | H-NMDMRCSASVECKQKCLKAIGSIFGKCMNKKCVCYPR-NH$_2$ (SEQ ID NO. 38) |
| 39 | H-N[Nle]D[Nle]RCSASVECKQKCLKAIGSIFGKCMNKKCKCYPR-NH$_2$ (SEQ ID NO. 39) |
| 40 | H-N[Nle]D[Nle]RCSASVECKQKCLKAIGSIFGKC[Nle]NKKCKCYPR-NH$_2$ (SEQ ID NO. 40) |
| 41 | H-P[Nle]D[Nle]RCSASVECKQKCLKAIGSIFGKC[Nle]NKKCKCYPR-NH$_2$ (SEQ ID NO. 41) |
| 42 | H-N[Nle]D[Nle]RCRASVECKQKCLKAIGSIFGKC[Nle]NKKCKCYPR-NH$_2$ (SEQ ID NO. 42) |
| 43 | H-N[Nle]D[Nle]RCSASVECEQKCLKAIGSIFGKC[Nle]NKKCKCYPR-NH$_2$ (SEQ ID NO. 43) |
| 44 | H-N[Nle]D[Nle]RCSASVECQQKCLKAIGSIFGKC[Nle]NKKCKCYPR-NH$_2$ (SEQ ID NO. 44) |
| 45 | H-N[Nle]D[Nle]RCSASVECKKKCLKAIGSIFGKC[Nle]NKKCKCYPR-NH$_2$ (SEQ ID NO. 45) |
| 46 | H-N[Nle]S[Nle]RCSASVECKQKCLKAIGSIFGKC[Nle]NKKCKCYPR-NH$_2$ (SEQ ID NO. 46) |
| 47 | H-N[Nle]D[Nle]RCSHSVECKQKCLKAIGSIFGKC[Nle]NKKCKCYPR-NH$_2$ (SEQ ID NO. 47) |
| 48 | H-N[Nle]D[Nle]RCSASVECKQSCLKAIGSIFGKC[Nle]NKKCKCYPR-NH$_2$ (SEQ ID NO. 48) |
| 49 | H-N[Nle]D[Nle]RCSASVECKQKCKAIGSIFGKC[Nle]NKKCKCYPR-NH$_2$ (SEQ ID NO. 49) |
| 50 | H-NMDMRCSASVECKQKCYKAIGSIFGKCMNKKCKCYPR-NH$_2$ (SEQ ID NO. 50) |
| 51 | H-NMDMRCSASVECKQKCIRKAIGSIFGKCMNKKCKCYPR-NH$_2$ (SEQ ID NO. 51) |
| 52 | H-NMDMRCSASVECKQKCLAAIGSIFGKCMNKKCKCYPR-NH$_2$ (SEQ ID NO. 52) |

TABLE 1-continued

| Cmpnd No. | Sequence |
|---|---|
| 53 | H-NMDMRCSASVECKQKCLYAIGSIFGKCMNKKCKCYPR-NH$_2$ (SEQ ID NO. 53) |
| 54 | H-NMDMRCSASVECKQKCLAIGSIFGKCMNKKCKCYPR-NH$_2$ (SEQ ID NO. 54) |
| 55 | H-NMDMRCSASVECKQKCLKYIGSIFGKCMNKKCKCYPR-NH$_2$ (SEQ ID NO. 55) |
| 56 | H-NMDMRCSASVECKQKCLKRIGSIFGKCMNKKCKCYPR-NH$_2$ (SEQ ID NO. 56) |
| 57 | H-NMDMRCSASVECKQKCLKIGSIFGKCMNKKCKCYPR-NH$_2$ (SEQ ID NO. 57) |
| 58 | H-NMDMRCSASVECKQKCLKAYGSIFGKCMNKKCKCYPR-NH$_2$ (SEQ ID NO. 58) |
| 59 | H-NMDMRCSASVECKQKCLKAEGSIFGKCMNKKCKCYPR-NH$_2$ (SEQ ID NO. 59) |
| 60 | H-NMDMRCSASVECKQKCLKARGSIFGKCMNKKCKCYPR-NH$_2$ (SEQ ID NO. 60) |
| 61 | H-NMDMRCSASVECKQKCLKAGSIFGKCMNKKCKCYPR-NH$_2$ (SEQ ID NO. 61) |
| 62 | H-N[Nle]D[Nle]RCSASVECKQKCLKAIGSPFGKC[Nle]NKKCKCYPR-NH$_2$ (SEQ ID NO. 62) |
| 63 | H-N[Nle]D[Nle]RCSASKECKQKCLKAIGSIFGKC[Nle]NKKCKCYPR-NH$_2$ (SEQ ID NO. 63) |
| 64 | H-H[Nle]D[Nle]RCSASVECKQKCLKAIGSIFGKC[Nle]NKKCKCYPR-NH$_2$ (SEQ ID NO. 64) |
| 65 | H-Y[Nle]D[Nle]RCSASVECKQKCLKAIGSIFGKC[Nle]NKKCKCYPR-NH$_2$ (SEQ ID NO. 65) |
| 66 | H-S[Nle]D[Nle]RCSASVECKQKCLKAIGSIFGKC[Nle]NKKCKCYPR-NH$_2$ (SEQ ID NO. 66) |
| 67 | H-V[Nle]D[Nle]RCSASVECKQKCLKAIGSIFGKC[Nle]NKKCKCYPR-NH$_2$ (SEQ ID NO. 67) |
| 68 | H-S[Nle]D[Nle]RCSA[Abu]VECKQKCLKAIGSIFGKCMNKKCKCYPR-NH$_2$ (SEQ ID NO. 68) |
| 69 | H-S[Nle]D[Nle]RCSASVECKQKCLKAIGSIFG[homo-Lys]CMNKKCKCYPR-NH$_2$ (SEQ ID NO. 69) |
| 70 | H-S[Nle]D[Nle]RCSASVECKQKCLKAIGSIFGKCMNKKCKC[F(4-NH$_2$)]PR-NH$_2$ (SEQ ID NO. 70) |
| 71 | H-S[Nle]D[Nle]RCSASVECGQKCLKAIGSIFGKCMNKKCKCYPR-NH$_2$ (SEQ ID NO. 71) |
| 72 | H-S[Nle]D[Nle]RCSASVECVQKCLKAIGSIFGKCMNKKCKCYPR-NH$_2$ (SEQ ID NO. 72) |
| 73 | H-S[Nle]D[Nle]RCSASVECK[2-Amino-5-carboxypentanoyl]KCLKAIGSIFGKCMNKKCKCYPR-NH$_2$ (SEQ ID NO. 73) |
| 74 | H-S[Nle]D[Nle]RCSASVECKQKCLKAIGSIFGKCMNKKCKCYQ-NH$_2$ (SEQ ID NO. 74) |
| 75 | H-S[Nle]D[Nle]RCSASVECKQKCLKAIGSIFGKCMNKKCIRCYPR-NH$_2$ (SEQ ID NO. 75) |
| 76 | H-S[Nle]DERCSASVECKQKCLKAIGSIFGKCMNKKCKCYPR-NH$_2$ (SEQ ID NO. 76) |

TABLE 1-continued

| Cmpnd No. | Sequence |
|---|---|
| 77 | H-S[Nle]D[Nle]RCSASVECKQKCLGAIGSIFGKCMNKKCKCYPR-NH$_2$ (SEQ ID NO. 77) |
| 78 | H-S[Nle]D[Nle]RCSASVECKQKCLVAIGSIFGKCMNKKCKCYPR-NH$_2$ (SEQ ID NO. 78) |
| 79 | H-S[Nle]D[Nle]RCSASVECAQSCLKAIGSIFGKCMNKKCKCYPR-NH$_2$ (SEQ ID NO. 79) |
| 80 | H-S[Nle]D[Nle]RCSASVECAQKCLAAIGSIFGKCMNKKCKCYPR-NH$_2$ (SEQ ID NO. 80) |
| 81 | H-S[Nle]D[Nle]RCSASVECAQLCLAAIGSIFGKCMNKKCKCYPR-NH$_2$ (SEQ ID NO. 81) |
| 82 | H-S[Nle]D[Nle]RCSASVECKQKCLKAIGSIFGKC[Nle]NKKCKCYPR-OH (SEQ ID NO. 82) |
| 83 | H-P[Nle]D[Nle]RCSASVECKQKCLKAIGCIFGKC[Nle]NKKCKCYPC-NH$_2$ (SEQ ID NO. 83) |
| 84 | H-S[Nle]D[Nle]RCSASVECKEKCLQAIGSIFGKC[Nle]NKKCKCYPR-NH$_2$ (SEQ ID NO. 84) |
| 85 | H-P[Nle]D[Nle]RCSASVECKEKCL[homo-Gln]AlGSIFGKC[Nle]NKKCKCYPR-NH$_2$ (SEQ ID NO. 85) |
| 86 | H-CSASVECKQKCLKAIGCIFGKC[Nle]NKKCKCYPC-NH$_2$ (SEQ ID NO. 86) |
| 87 | H-S[Nle]D[Nle]RCSASVECKQKCLAAIGCIFGKC[Nle]NKKCKCYPC-NH$_2$ (SEQ ID NO. 87) |
| 88 | H-P[Nle]D[Nle]RCSASVECKQKCLKAIGCIFGKC[Nle]NKKCKCYPC-OH (SEQ ID NO. 88) |
| 89 | H-S[Nle]D[Nle]RCSALVECKQKCLKAIGSIFGKCMNKKCKCYPR-NH$_2$ (SEQ ID NO. 89) |
| 90 | H-S[Nle]D[Nle]RCSAVVECKQKCLKAIGSIFGKCMNKKCKCYPR-NH$_2$ (SEQ ID NO. 90) |
| 91 | H-S[Nle]D[Nle]RCSASVECKQKCLKAIGSIFGKCMNKKCKC[F(4-F)]PR-NH$_2$ (SEQ ID NO. 91) |
| 92 | H-S[Nle]D[Nle]RCSASVECKQKCLKAIGSIFGKCMNKKCKC[F(4-NO$_2$)]PR-NH$_2$ (SEQ ID NO. 92) |
| 93 | H-S[Nle]D[Nle]RCSASVECKQKCLKAIGSIFGKCMNKKCKC[F(4-CH$_3$)]PR-NH$_2$ (SEQ ID NO. 93) |
| 94 | H-[Nle]D[Nle]RCSASVECKQKCLKAIGSIFGKC[Nle]NKKCKCYPR-OH (SEQ ID NO. 94) |
| 95 | H-NID[Nle]RCSASVECKQKCLKAIGSIFGKC[Nle]NKKCKCYPR-OH (SEQ ID NO. 95) |
| 96 | H-PIE[Nle]RCSASVECKQKCLKAIGSIFGKC[Nle]NKKCKCYPR-OH (SEQ ID NO. 96) |
| 97 | H-P[Nle]E[Nle]RCSASVECKQKCLAAIGSIFGKC[Nle]NKKCKCYPR-OH (SEQ ID NO. 97) |
| 98 | H-P[Nle]E[Nle]RCSASVECKQKCLAAIGSIFGKC[Nle]NKKCKCYPR-NH$_2$ (SEQ ID NO. 98) |
| 99 | H-P[Nle]E[Nle]RCSASVECKQKCLLAIGSIFGKC[Nle]NKKCKCYPR-OH (SEQ ID NO. 99) |
| 100 | H-PIDERCSASVECKQKCLAAIGSIFGKC[Nle]NKKCKCYPR-OH (SEQ ID NO. 100) |

TABLE 1-continued

| Cmpnd No. | Sequence |
|---|---|
| 101 | H-PIE[Nle]RCSASVECKQKCLAAIGSIFGKC[Nle]NKKCKCYPR-OH (SEQ ID NO. 101) |
| 102 | H-P[Nle]D[Nle]RCSASVECAQKCLAAIGSIFGKCMNKKCKCYPR-OH (SEQ ID NO. 102) |
| 103 | H-P[Nle]E[Nle]RCSASVECAQKCLAAIGSIFGKC[Nle]NKKCKCYPR-OH (SEQ ID NO. 103) |
| 104 | H-CSASVECKQKCLKAIGSIFGKC[Nle]NKKCKCYPR-NH$_2$ (SEQ ID NO. 104) |
| 105 | Ac-CSASVECKQKCLKAIGSIFGKC[Nle]NKKCKCYPR-NH$_2$ (SEQ ID NO. 105) |
| 106 | H-RCSASVECKQKCLKAIGSIFGKC[Nle]NKKCKCYPR-NH$_2$ (SEQ ID NO. 106) |
| 107 | Ac-SKCSASVECKQKCLKAIGSIFGKC[Nle]NKKCKCYPR-NH$_2$ (SEQ ID NO. 107) |
| 108 | Ac-LRCSASVECKQKCLKAIGSIFGKC[Nle]NKKCKCYPR-NH$_2$ (SEQ ID NO. 108) |
| 109 | Ac-CSASVECKQKCLKAIGSIFGKC[Nle]NKKCKCYPS-NH$_2$ (SEQ ID NO. 109) |
| 110 | Ac-CSASVECKQKCLKAIGSIFGKC[Nle]NKKCKCYS-NH$_2$ (SEQ ID NO. 110) |
| 111 | Ac-CSASVECKQKCLKAIGSIFGKC[Nle]NKKCKCYG-NH$_2$ (SEQ ID NO. 111) |
| 112 | Ac-CSASVECKQKCLKAIGSIFGKC[Nle]NKKCKCY-NH$_2$ (SEQ ID NO. 112) |
| 113 | Ac-RCSASVECKQKCLKAIGSIFGKC[Nle]NKKCKCYPR-OH (SEQ ID NO. 113) |
| 114 | H-LRCSASVECKQKCLKAIGSIFGKC[Nle]NKKCKCYPR-OH (SEQ ID NO. 114) |
| 115 | Ac-LRCSASVECKQKCLKAIGSIFGKC[Nle]NKKCKCYPR-OH (SEQ ID NO. 115) |
| 116 | Ac-LRCSASVECKQKCLAAIGSIFGKCMNKKCKCYPR-OH (SEQ ID NO. 116) |
| 117 | H-CSASVECKQKCLKAIGSIFGKCMNKKCKCYPR-OH (SEQ ID NO. 117) |
| 118 | H-P[Nle]E[Nle]RCSASVECKEKCLAAIGSIFGKC[Nle]NKKCKCYPR-OH (SEQ ID NO. 118) |
| 119 | H-p[Nle]E[Nle]RCSASVECKQKCLAAIGSIFGKC[Nle]NKKCKCYPR-OH (SEQ ID NO. 119) |
| 120 | H-P[Nle]E[Nle]RCSASVECKQKCLAAIGSIFGKC[Nle]NKKCKCYR-OH (SEQ ID NO. 120) |
| 121 | H-[Nle]E[Nle]RCSASVECKQKCLAAIGSIFGKC[Nle]NKKCKCYPR-OH (SEQ ID NO. 121) |
| 122 | H-P[Nle]E[Nle]RCSASVECKQKCLAAIGSIFGKC[Nle]NKKCKCYPRR-OH (SEQ ID NO. 122) |
| 123 | H-P[Nle]E[Nle]RCSASVECKQKCLAAIGSIFGKC[Nle]NKKCKCYPRY-OH (SEQ ID NO. 123) |
| 124 | H-P[Nle]E[Nle]RCSASVECKQKCLAAIGSIFGKC[Nle]NKKCKCYPRL-OH (SEQ ID NO. 124) |
| 125 | H-P[Nle]E[Nle]RCSASVECKQKCLAAIGSIFGKC[Nle]NKKCKCYPRH-OH (SEQ ID NO. 125) |

TABLE 1-continued

| Cmpnd No. | Sequence |
|---|---|
| 126 | H-P[Nle]E[Nle]RCSASVECKQKCLAAIGSIFGKC[Nle]NKKCKCYPRE-OH (SEQ ID NO. 126) |
| 127 | H-P[Nle]E[Nle]RCSASVECKQKCLAAIGSIFGKC[Nle]NKKCKCYPRKS-OH (SEQ ID NO. 127) |
| 128 | H-P[Nle]E[Nle]RCSASVECKQKCLAAIGSIFGKC[Nle]NKKCKCYPRFE-OH (SEQ ID NO. 128) |
| 129 | H-P[Nle]E[Nle]RCSASVECKQKCLAAIGSIFGKC[Nle]NKKCKCYPRHR-OH (SEQ ID NO. 129) |
| 130 | H-P[Nle]E[Nle]RCSASVECKQKCLAAIGSIFGKC[Nle]NKKCKCYPRAK-OH (SEQ ID NO. 130) |
| 131 | H-P[Nle]E[Nle]RCSASVECKQKCLAAIGSIFGKC[Nle]NKKCKCYP-[(4-amino-5-hydroxypentyl)guanidine] (SEQ ID NO. 131) |
| 132 | H-P[Nle]E[Nle]RCSASVECKQKCLAAIGSIFGKC[Nle]NKKCKCYPR-[4-amino-5-hydroxypentanamide] (SEQ ID NO. 132) |
| 133 | H-P[Nle]E[Nle]RCSASVECKQKCLAAIGSIFGKC[Nle]NKKCKCYPRST-OH (SEQ ID NO. 133) |
| 134 | H-P[Nle]E[Nle]RCSASVECKQKCLAAIGSIFGKC[Nle]NKKCKCYPRRY-OH (SEQ ID NO. 134) |
| 135 | H-P[Nle]E[Nle]RCSSSVECKQKCLAAIGSIFGKC[Nle]NKKCKCYPR-OH (SEQ ID NO. 135) |
| 136 | H-P[Nle]E[Nle]RCSLSVECKQKCLAAIGSIFGKC[Nle]NKKCKCYPR-OH (SEQ ID NO. 136) |
| 137 | H-P[Nle]E[Nle]RCSAPVECKQKCLAAIGSIFGKC[Nle]NKKCKCYPR-OH (SEQ ID NO. 137) |
| 138 | H-P[Nle]E[Nle]RCSASPECKQKCLAAIGSIFGKC[Nle]NKKCKCYPR-OH (SEQ ID NO. 138) |
| 139 | H-P[Nle]E[Nle]RCSASQECKQKCLAAIGSIFGKC[Nle]NKKCKCYPR-OH (SEQ ID NO. 139) |
| 140 | H-P[Nle]E[Nle]RCSASVECLQKCLAAIGSIFGKC[Nle]NKKCKCYPR-OH (SEQ ID NO. 140) |
| 141 | H-P[Nle]E[Nle]RCSASVECKQPCLAAIGSIFGKC[Nle]NKKCKCYPR-OH (SEQ ID NO. 141) |
| 142 | H-P[Nle]E[Nle]RCEASVECKQKCLAAIGSIFGKC[Nle]NKKCKCYPR-OH (SEQ ID NO. 142) |
| 143 | H-P[Nle]E[Nle]RCFASVECKQKCLAAIGSIFGKC[Nle]NKKCKCYPR-OH (SEQ ID NO. 143) |
| 144 | H-P[Nle]E[Nle]RCSYSVECKQKCLAAIGSIFGKC[Nle]NKKCKCYPR-OH (SEQ ID NO. 144) |
| 145 | H-P[Nle]E[Nle]RCSAFVECKQKCLAAIGSIFGKC[Nle]NKKCKCYPR-OH (SEQ ID NO. 145) |

The following compounds were also synthesised for use as controls:

```
ShK
                                   (SEQ ID NO: 177)
H-RSCIDTIPKSRCTAFQCKHSMKYRLSFCRKTCGTC-OH

ShK186
                                   (SEQ ID NO: 178)
H-[phosphotyrosyl)][8-Amino-3,6-dioxaoctanoyl]
RSCIDTIPKSRCTAFQCKHSMKYRLSFCRKTCGTC-NH2

Moka1
                                   (SEQ ID NO: 179)
H-INVKCSLPQQCIKPCKDAGMRFGKCMNKKCRCYS-OH Vm24
                                   (SEQ ID NO: 180)
H-AAAISCVGSPECPPKCRAQGCKNGKCMNRKCKCYYC-NH2
```

Example 2: Kv1.3 Blocker Activity in FLIPR Thallium Assay

A human Kv1.3 voltage-gated K+ channel cell line was purchased from Perkin Elmer (TDS-AX-010-C-1). The cell line is based on CHO-DUKX cells stably transfected with the human Kv1.3 voltage-gated K+ channel.

The cell line was grown in MEMα with nucleotides, GlutaMAX (Gibco Cat #32571028), 10% Foetal Bovine Serum (FBS), 0.4 mg/ml Geneticin, 100 units/ml Penicillin, and 100 µg/ml Streptomycin and seeded at 10.000 cells/well in black poly-D-lysine-coated 96 well plates.

The FluxOR™ Potassium Ion Channel Assay (Invitrogen Cat #F10016) was used to quantitate flux of thallium ions into the cells as a response to Kv1.3 activation with a stimulus buffer causing depolarization of the cell membrane, generating a fluorescent signal, proportional to channel activity. The assay was performed as described by the assay kit manufacturer. Fluorescence responses were recorded and quantified using the FLIPR® Tetra High Throughput Screening System (Molecular Devices, Inc.).

Data from test compounds eliciting an inhibition of thallium flux into the cell were normalised relative to the positive (ShK) and negative control (vehicle) to calculate the $IC_{50}$ from the concentration response curve. Results are shown in Table 2. $IC_{50}$ can be regarded as a measure of potency of inhibition for the respective compound. The $IC_{50}$ value is a measure of the concentration of an inhibitor required to achieve half of that compound's maximal inhibition of ion channel activity in a given assay. A compound which has a lower $IC_{50}$ at a particular ion channel than a reference compound can be considered to be a more active inhibitor, or a more potent inhibitor, than the reference compound.

TABLE 2

| Compound | IC50 (nM) |
| --- | --- |
| 1 | 0.24 |
| 2 | 0.25 |
| 3 | 0.30 |
| 4 | 0.29 |
| 5 | 0.25 |
| 6 | 0.34 |
| 7 | 0.12 |
| 8 | 0.47 |
| 9 | 0.53 |
| 10 | 0.57 |

TABLE 2-continued

| Compound | IC50 (nM) |
| --- | --- |
| 11 | 0.3 |
| 12 | 0.23 |
| 13 | 0.26 |
| 14 | 0.16 |
| 15 | 0.12 |
| 16 | 0.14 |
| 17 | 0.14 |
| 18 | 0.19 |
| 19 | 0.12 |
| 20 | 0.13 |
| 21 | 0.12 |
| 22 | 0.11 |
| 23 | 0.055 |
| 24 | 0.073 |
| 25 | 0.085 |
| 26 | 0.092 |
| 27 | 0.065 |
| 28 | 0.064 |
| 29 | 0.18 |
| 30 | 0.09 |
| 31 | 0.075 |
| 32 | 0.12 |
| 33 | 0.14 |
| 34 | 0.11 |
| 35 | 0.077 |
| 36 | 0.24 |
| 37 | 0.14 |
| 38 | 0.46 |
| 39 | 0.11 |
| 40 | 0.1 |
| 41 | 0.15 |
| 42 | 0.087 |
| 43 | 0.5 |
| 44 | 0.13 |
| 45 | 0.16 |
| 46 | 0.11 |
| 47 | 0.12 |
| 48 | 0.14 |
| 49 | 0.36 |
| 50 | 0.16 |
| 51 | 0.11 |
| 52 | 0.11 |
| 53 | 0.12 |
| 54 | 0.46 |
| 55 | 0.12 |
| 56 | 0.087 |
| 57 | 0.11 |
| 58 | 0.11 |
| 59 | 0.035 |
| 60 | 0.035 |
| 61 | 0.40 |
| 62 | 0.13 |
| 63 | 0.13 |
| 64 | 0.12 |
| 65 | 0.12 |
| 66 | 0.12 |
| 67 | 0.12 |
| 68 | 0.20 |
| 69 | 0.58 |
| 70 | 0.13 |
| 71 | 0.10 |
| 72 | 0.19 |
| 73 | 0.11 |
| 74 | 0.36 |
| 75 | 0.10 |
| 76 | 0.093 |
| 77 | 0.13 |
| 78 | 0.12 |
| 79 | 0.13 |
| 80 | 0.15 |
| 81 | 0.22 |
| 82 | 0.49 |
| 83 | 0.12 |
| 84 | 0.084 |
| 85 | 0.15 |
| 86 | 0.20 |
| 87 | 0.10 |
| 88 | 0.27 |

TABLE 2-continued

| Compound | IC50 (nM) |
|---|---|
| 89 | 2.7 |
| 90 | 0.19 |
| 91 | 0.10 |
| 92 | 0.49 |
| 93 | 0.13 |
| 94 | 0.16 |
| 95 | 0.16 |
| 96 | 0.15 |
| 97 | 0.15 |
| 98 | 0.11 |
| 99 | 0.34 |
| 100 | 0.85 |
| 101 | 0.18 |
| 102 | 0.45 |
| 103 | 0.38 |
| 104 | 0.12 |
| 105 | 0.16 |
| 106 | 0.092 |
| 107 | 0.084 |
| 108 | 0.1 |
| 109 | 0.96 |
| 110 | 2.3 |
| 111 | 2.1 |
| 112 | 1.7 |
| 113 | 0.34 |
| 114 | 0.39 |
| 115 | 0.31 |
| 116 | 0.18 |
| 117 | 1.5 |
| 118 | 1.39 |
| 119 | 0.63 |
| 120 | 0.894 |
| 121 | 0.451 |
| 122 | 0.226 |
| 123 | 1.04 |
| 124 | 1.47 |
| 125 | 0.383 |
| 126 | 6.49 |
| 127 | 0.562 |
| 128 | 7.18 |
| 129 | 0.143 |
| 130 | 0.529 |
| 131 | 0.156 |
| 132 | 0.224 |
| 133 | 1.1 |
| 134 | 0.21 |
| 135 | 0.336 |
| 136 | 6.24 |
| 137 | 0.333 |
| 138 | 0.228 |
| 139 | 0.453 |
| 140 | 3.57 |
| 141 | 1.07 |
| 142 | 1.5 |
| 143 | 0.316 |
| 144 | 0.739 |
| 145 | 8.26 |

Example 3: Kv1.3 Selectivity in Patch Clamp Assay

Chinese Hamster Ovary (CHO) cell lines stably expressing exogenous human α-subunits of each potassium ion channel were grown and passaged under standard culture conditions.

The automated, chip-based planar patch clamp device QPatch® was used to quantitate the ionic currents. All recordings were made in the conventional whole-cell configuration after establishment of gigaohm seals. External recording solution contained (150 mM NaCl, 10 mM KCl, 10 mM HEPES, 1 mM $MgCl_2$, 3 mM $CaCl_2$, 10 mM Glucose, pH adjusted to 7.4 with NaOH) and Internal recording solution (20 mM KCl, 120 mM KF, 10 mM HEPES, 10 mM EGTA, 5 mM NaATP, pH adjusted to 7.2 with KOH). During experiments 0.1% (v/v) BSA was included as a vehicle in all external recording solutions. Currents were elicited from a holding potential of −80 mV using a voltage protocol, which shifted the voltage to 30 mV for 500 ms every 15 s. Concentration-response relationships were established by cumulatively applying seven escalating concentrations of test sample to an individual cell with a recording period of 2 min per compound application.

The efficacy was determined as the mean charge for the last three sweeps at the end of each concentration application period from the cursor positions. The percent inhibition for each test dose application period was calculated as the reduction in mean cursor value (charge) relative to the cursor value measured at the end of the vehicle period and used to calculate the $IC_{50}$ from the concentration response curve. Results are shown in Table 3.

TABLE 3

| Compound | Potency $IC_{50}$ (nM) | | | | Selectivity | | |
|---|---|---|---|---|---|---|---|
| | Kv1.1 | Kv1.2 | Kv1.3 | Kv1.6 | Kv1.1/Kv1.3 | Kv1.2/Kv1.3 | Kv1.6/Kv1.3 |
| 1 | >3000 | 518 | 0.38 | >3000 | >7900 | 1364 | >7900 |
| 2 | >3000 | 97 | 1.50 | 1810 | >2000 | 65 | 1204 |
| 3 | >3000 | 409 | 0.27 | >3000 | >11300 | 1540 | >11300 |
| 5 | >3000 | 285 | 0.38 | >3000 | >7900 | 747 | >7900 |
| 8 | >3000 | 376 | 0.44 | >3000 | >6800 | 857 | >6800 |
| 12 | >3000 | 228 | 0.11 | >3000 | >27600 | 2093 | >27600 |
| 16 | >3000 | 133 | 0.24 | 2460 | >12600 | 561 | 10360 |
| 17 | >3000 | 66 | 0.42 | 912 | >7200 | 159 | 2182 |
| 18 | >3000 | 256 | 0.24 | >3000 | >12700 | 1080 | >12700 |
| 19 | >3000 | 45 | 0.22 | 435 | >13500 | 202 | 1955 |
| 20 | >3000 | 99 | 0.21 | 2527 | >14300 | 471 | 12045 |
| 21 | >3000 | 57 | 0.22 | 626 | >13700 | 259 | 2851 |
| 22 | >3000 | 181 | 0.29 | >3000 | >10200 | 615 | >10200 |
| 23 | 626 | 28 | 0.15 | 215 | 4280 | 191 | 1472 |
| 25 | >3000 | 67 | 0.09 | 363 | >34200 | 761 | 4144 |
| 26 | >3000 | 43 | 0.26 | >3000 | >11800 | 169 | >11800 |
| 27 | >3000 | 11 | 0.12 | 206 | >25900 | 94 | 1778 |
| 28 | >3000 | 16 | 0.20 | 252 | >15200 | 83 | 1272 |
| 29 | >3000 | 874 | 0.40 | >3000 | >7400 | 2163 | >7400 |
| 30 | >3000 | 666 | 0.14 | >3000 | >22000 | 4897 | >22000 |
| 31 | >3000 | 179 | 0.28 | >3000 | >10800 | 648 | >10800 |

TABLE 3-continued

| | Potency IC$_{50}$ (nM) | | | | Selectivity | | |
|---|---|---|---|---|---|---|---|
| Compound | Kv1.1 | Kv1.2 | Kv1.3 | Kv1.6 | Kv1.1/Kv1.3 | Kv1.2/Kv1.3 | Kv1.6/Kv1.3 |
| 32 | | | 0.38 | | | | |
| 34 | >3000 | 100 | 0.42 | 207 | >7100 | 237 | 490 |
| 35 | >3000 | 18 | 0.20 | 192 | >15000 | 88 | 963 |
| 36 | >3000 | 439 | 0.31 | >3000 | >9700 | 1422 | >9700 |
| 37 | >3000 | 338 | 0.19 | >3000 | >16100 | 1816 | >16100 |
| 39 | | | 0.15 | | | | |
| 40 | >3000 | 113 | 0.26 | 1829 | >11600 | 436 | 7073 |
| 41 | >3000 | 939 | 0.18 | >3000 | >17100 | 5362 | >17100 |
| 42 | >3000 | 109 | 0.16 | 316 | >18600 | 674 | 1954 |
| 45 | >3000 | 257 | 0.75 | >3000 | >4000 | 343 | >4000 |
| 46 | >3000 | 302 | 0.32 | 1395 | >9400 | 943 | 4359 |
| 47 | >3000 | 772 | 0.54 | 609 | >5600 | 1438 | 1134 |
| 48 | >3000 | >3000 | 0.37 | >3000 | >8200 | >8200 | >8200 |
| 49 | >3000 | 164 | 1.34 | 946 | >2200 | 123 | 707 |
| 50 | | | 0.27 | | | | |
| 51 | | | 0.25 | | | | |
| 52 | >3000 | 88 | 0.11 | >3000 | >27500 | 803 | >27500 |
| 53 | >3000 | 149 | 0.29 | >3000 | >10300 | 514 | >10300 |
| 54 | >3000 | 291 | 2.41 | >3000 | >1200 | 121 | >1200 |
| 55 | | | 0.12 | | | | |
| 56 | >3000 | 57 | 0.30 | 932 | >9900 | 187 | 3062 |
| 58 | >3000 | 145 | 0.34 | >3000 | >8800 | 426 | >8800 |
| 62 | >3000 | 449 | 0.26 | 2349 | >11600 | 1740 | 9102 |
| 63 | >3000 | 184 | 0.31 | 1231 | >9600 | 587 | 3929 |
| 64 | | | 0.25 | | | | |
| 65 | | | 0.14 | | | | |
| 66 | | | 0.18 | | | | |
| 67 | | | 0.32 | | | | |
| 70 | >3000 | 423 | 0.25 | >3000 | >12200 | 1720 | >12200 |
| 71 | >3000 | 373 | 0.11 | >3000 | >27700 | 3438 | >27700 |
| 75 | | | 0.13 | | | | |
| 76 | >3000 | 122 | 0.28 | >3000 | >10600 | 430 | >10600 |
| 79 | >3000 | 1149 | 0.21 | >3000 | >14600 | 5596 | >14600 |
| 80 | | | 0.16 | | | | |
| 83 | >3000 | 624 | 0.63 | 1222 | >4800 | 995 | 1949 |
| 94 | >3000 | 1859 | 0.17 | >3000 | >17800 | 11034 | >17800 |
| 95 | >3000 | 2063 | 0.27 | >3000 | >11300 | 7756 | >11300 |
| 96 | >3000 | 1758 | 0.39 | >3000 | >7800 | 4561 | >7800 |
| 97 | >3000 | 1117 | 0.33 | >3000 | >9100 | 3384 | >9100 |
| 98 | >3000 | 311 | 0.18 | >3000 | >16200 | 1689 | >16200 |
| 101 | >3000 | 1968 | 0.35 | >3000 | >8600 | 5630 | >8600 |
| 103 | >3000 | >3000 | 0.55 | >3000 | >5500 | 5500 | >5500 |
| 104 | >3000 | >3000 | 0.43 | >3000 | >7000 | >7000 | >7000 |
| 105 | >3000 | 384 | 0.24 | >3000 | >12400 | 1591 | >12400 |
| 106 | >3000 | 280 | 0.40 | 1302 | >7600 | 708 | 3290 |
| 107 | >3000 | 196 | 1.00 | 1451 | >3000 | 196 | 1451 |
| 108 | >3000 | 122 | 0.35 | 2456 | >8700 | 352 | 7096 |
| 117 | >3000 | 1832 | 2.09 | >3000 | >1400 | 878 | >1400 |
| ShK | 0.0021 | 11 | 0.017 | 0.19 | 0.12 | 644 | 11 |
| ShK-186 | 0.31 | 43 | 0.095 | 0.45 | 4.9 | 682 | 7.4 |
| Moka1 | >3000 | 275 | 9.0 | >3000 | >300 | 31 | >300 |
| Vm24 | 0.097 | 4.7 | 0.15 | 21 | 0.65 | 31 | 139 |

Comparison of the data in Examples 2 and 3 shows that a good correlation exists between the IC$_{50}$ values as measured in the two assays.

Example 4a: Inhibitory Activity of Kv1.3 Blockers on Human PBMCs

Human peripheral blood mononuclear cells (PBMCs) were used to assess the effects of Kv1.3 blockers on T-cell activation as determined by IL-2 (cytokine) release after stimulation with anti-CD3.

Human PBMCs were obtained from Precision for Medicine (Frederick, Md.). Cells from 5 donors were used. Plate-bound anti-CD3 was used to stimulate bulk T cells in the PBMC preparations. Briefly, 96-well plates were coated with anti-CD3 antibody for 2 hrs at 37° C., using 50 μL of a 0.5 μg/mL anti-CD3 solution diluted in 1×PBS. Thereafter the plates were washed twice.

Kv1.3 blockers as shown in Table 4a were diluted in medium (RPMI 1640 with Glutamax-I containing 10% v/v Fetal Bovine Serum, 1% v/v penicillin-streptomycin solution) and added in a volume of 100 μL at concentrations ranging from 0.01 μM to 100 nM (tenfold dilutions). Cyclosporin A (1 ug/ml) and Vm24 peptide (100 nM) were used as positive controls. Finally, 1×10$^5$ PBMCs were added to each well in a volume of 100 μL, giving a final volume of 200 μL per well. The plates were incubated for 20-24 hours in a 37° C./5% CO$_2$ incubator. After centrifugation of the plates, 25 μl supernatant was transferred to IL-2 detection plates (MSD Human IL-2 Tissue Culture Kit, cat #K151AHB-2) and IL-2 was measures as described by the manufacturer (Meso Scale Discovery, Rockville, Md., USA).

Results are shown in Table 4a as geometric mean of IC50 values obtained from anti-CD3 stimulated human PBMC assays. All values derive from at least 4 replicates.

TABLE 4a

| Compound | anti-CD3 PBMC/IL-2 IC50 [nM] |
|---|---|
| ShK-186 | 0.07 |
| 16 | 0.05 |
| 17 | 0.4 |
| 20 | 0.1 |
| 35 | 0.1 |

Incubation with anti-CD3 antibody activated hPBMC and addition of Kv1.3 blockers resulted in dose-dependent reduction in the IL-2 secretion. On average the $IC_{50}$ values (as calculated from IL-2 release) of the test compounds were in the range of 0.05 nM to 0.4 nM. This was comparable to the $IC_{50}$ observed with ShK186 ($IC_{50}$ is 0.07 nM) and about 10-100 fold lower than the $IC_{50}$ of Moka1 which was less potent in inhibiting IL-2 secretion.

There is no significant difference between the test compounds and ShK186. ShK186 and test compounds were all significantly lower than Moka1.

Cyclosporine blocked CD3 induced IL-2 release completely in all experiments.

Example 4b: Inhibitory Activity of Kv1.3 Blockers on Human PBMCs

Human peripheral blood mononuclear cells (PBMCs) were used to assess the effects of Kv1.3 blockers on T-cell activation as determined by IL-2 release after stimulation with anti-CD3.

Human PBMCs were obtained from Precision for Medicine (Frederick, Md.). Cells from 5 donors were used. Plate-bound anti-CD3 was used to stimulate bulk T cells in the PBMC preparations. Briefly, 96-well plates were coated with anti-CD3 antibody for app. 16 hours at 5° C., using 50 µl of a 1 µg/ml anti-CD3 solution diluted in PBS. Thereafter the plates were washed twice.

Kv1.3 blockers were subsequently diluted in medium (RPMI 1640 with Glutamax-I containing, 10% v/v Fetal Bovine Serum, 1% v/v penicillin-streptomycin Solution) and added in a volume of 50 µl. The compounds indicated in Table 4b were used at concentrations ranging from 0.3 µM to 1000 nM (half log dilutions, starting concentrations varying). Cyclosporin A (1 µg/ml) and Vm24 peptide (100 nM) were used as positive controls.

Finally, 50.000 PBMCs in the same medium were added to each well in a volume of 50 µl, giving a final volume of 100 µl per well. The plates were incubated for 20-24 hours in a 37° C./5% $CO_2$ incubator. After centrifugation of the plates, 25 µl supernatant was transferred to IL-2 detection plates (MSD Human IL-2 Tissue Culture Kit, cat #K151AHB-2) and IL-2 was measures as described by the manufacturer (Meso Scale Discovery, Rockville, Md., USA).

Results are shown in Table 4b as geometric mean of IC50 values obtained from anti-CD3 stimulated human PBMC assays. All values derive from at least 6 replicates.

TABLE 4b

| Compound | anti-CD3 PBMC/IL-2 IC50 [nM] |
|---|---|
| ShK-186 | 0.04 |
| 3 | 0.06 |
| 1 | 0.09 |
| 41 | 0.03 |

TABLE 4b-continued

| Compound | anti-CD3 PBMC/IL-2 IC50 [nM] |
|---|---|
| 23 | 0.06 |
| 48 | 0.07 |

Incubation with anti-CD3 antibody activated hPBMC and addition of the Compounds of this invention resulted in dose-dependent reduction in the IL-2 secretion. The average $IC_{50}$ values (as calculated from IL-2 release) of the test compounds were in the range of 0.01 nM to 0.09 nM as shown in Table 4b. This was comparable to the $IC_{50}$ observed with ShK186 ($IC_{50}$ is 0.05 nM). This assay was performed using different donors than those used for Example 4a, so identical values for the Shk-186 in the two sets of experiments are not expected.

Cyclosporine blocked anti-CD3 induced IL-2 release completely in all experiments.

Example 5: Inhibitory Activity of Kv1.3 Blockers in Rat Whole Blood

Rat whole blood was used to assess the potency of Kv1.3 blockers on T-cell activation as determined by IL-17A release after stimulation with thapsigargin. Addition of thapsigargin results in activation of a signalling cascade ending up in activation of T cell proliferation and cytokine production where the Kv1.3 ion channel plays a key role, so activity of Kv1.3 blockers in primary cells can be measured in this experimental system.

Rat whole blood was obtained from healthy, naïve Lewis or Sprague-Dawley rats that were terminally bleed from the heart using Sodium Heparin blood sampling tubes for collection. Test compounds were diluted to 4x final testing concentrations in assay buffer (DMEM+GlutaMAX), GlutaMAX is a medium comprising 3.97 mM L-alanine-L-glutamine (Gibco Cat #61965026) supplemented with 25 mM HEPES buffer, 1 mM Sodium Pyruvate, 100 units/ml Penicillin, 100 µg/ml Streptomycin and 0.05% Casein from bovine milk (Sigma-Aldrich)) and 25 µl was added to wells of a 96 well plate. Then 50 µl whole rat blood was added and incubated for minimum 5 minutes at room temperature to allow compound binding. Then 25 µl 40 µM thapsigargin diluted in assay buffer was added to all wells of the assay plates to activate the cells, followed by incubation for 24 Hr at 37° C./5% $CO_2$ in a humidified box. The assay plates were centrifuged for 10 min at 300 g at 4° C. and the supernatants were transferred to new plates. The concentrations of IL-17A released to the supernatants were measured using a Rat IL-17A ELISA Kit (Abcam Cat #ab214028) as recommended by the manufacturer. Samples were diluted 2.5-fold by transferring 20 µl of the supernatants to wells on ELISA plates containing 30 µl buffer 75BS from the detection kit. Data from test compounds eliciting an inhibition of IL-17A were normalised relative to full thapsigargin activation (no blocker added) and no activation controls (addition of assay buffer instead of thapsigargin) to calculate the $IC_{50}$ from the concentration response curve.

Results are shown in Table 5, expressed as $IC_{50}$, with standard deviation ($IC_{50\_}SD$). All values are derived from at least 2 replicates. The biological effects ex vivo show a correlation with the potency of the compounds.

TABLE 5

| CPD NO | IC$_{50}$ | IC$_{50}$_SD |
|---|---|---|
| 1 | 0.17 | 0.036 |
| 3 | 1.0 | 0.31 |
| 17 | 0.88 | 0.32 |
| 18 | 3.2 | 0.017 |
| 19 | 0.56 | 0.2 |
| 20 | 1.2 | 0.72 |
| 21 | 0.82 | 0.81 |
| 22 | 2.8 | 2.5 |
| 23 | 0.57 | 0.24 |
| 26 | 0.61 | 0.33 |
| 27 | 0.68 | 0.47 |
| 28 | 0.53 | 0.21 |
| 29 | 0.76 | 0.23 |
| 30 | 0.41 | 0.021 |
| 31 | 0.86 | 0.31 |
| 32 | 0.75 | 0.24 |
| 33 | 0.70 | 0.40 |
| 34 | 2.1 | 0.89 |
| 35 | 2.5 | 2.1 |
| 36 | 1.2 | 0.7 |
| 37 | 0.77 | 0.56 |
| 38 | 2.8 | 1.8 |
| 41 | 0.98 | 0.60 |
| 42 | 0.91 | 0.26 |
| 43 | 0.99 | 0.24 |
| 44 | 1.1 | 0.47 |
| 45 | 1.4 | 0.64 |
| 46 | 0.79 | 0.28 |
| 47 | 0.83 | 0.4 |
| 48 | 0.63 | 0.039 |
| 49 | 1.0 | 0.65 |
| 52 | 0.69 | 0.21 |
| 62 | 0.44 | 0.080 |
| 63 | 0.68 | 0.19 |
| 64 | 1.2 | 0.71 |
| 65 | 1.1 | 0.011 |
| 66 | 0.47 | 0.35 |
| 67 | 0.98 | 0.076 |
| 68 | 0.93 | 0.72 |
| 69 | 2.7 | 0.54 |
| 70 | 0.79 | 0.15 |
| 71 | 0.30 | 0.11 |
| 72 | 0.47 | 0.086 |
| 73 | 0.52 | 0.019 |
| 74 | 1.6 | 1.1 |
| 75 | 0.86 | 0.13 |
| 76 | 0.55 | 0.25 |
| 78 | 0.39 | 0.28 |
| 82 | 0.52 | 0.059 |
| 83 | 0.81 | 0.13 |
| 84 | 0.69 | 0.38 |
| 85 | 1.4 | 1.1 |
| 86 | 1.1 | 1.3 |
| 87 | 0.73 | 0.28 |
| 88 | 1.1 | 1.2 |
| 91 | 0.34 | 0.07 |
| 92 | 1.3 | 1.0 |
| 93 | 0.54 | 0.31 |
| 94 | 0.55 | 0.42 |
| 95 | 1.2 | 0.57 |
| 96 | 1.8 | 1.2 |
| 97 | 0.43 | 0.42 |
| 98 | 0.34 | 0.21 |
| 99 | 0.5 | 0.37 |
| 100 | 0.87 | 0.84 |
| 101 | 0.61 | 0.34 |
| 102 | 0.32 | 0.22 |
| 103 | 1.2 | 1.5 |
| 104 | 1.6 | 0.94 |
| 105 | 0.88 | 0.011 |
| 106 | 0.52 | 0.34 |
| 107 | 0.36 | 0.13 |
| 108 | 0.37 | 0.049 |
| 114 | 2.1 | 2.5 |
| 115 | 0.9 | 0.3 |
| 116 | 0.36 | 0.24 |
| 117 | 1.9 | 1 |

Example 6: Pharmacokinetic Characterisation

Method

Sprague Dawley or Wistar rats (males with a body weight of approximately 250-350 g) were given a single subcutaneous (s.c.) injection of each peptide to be tested.

Following s.c. administration of the selected compounds (dose 70 nmol/kg, dosing volume either 2 or 5 mL/kg), blood samples were drawn at 15 min, 30 min, 45 min, 60 min, 90 min, 2 h, 3 h, 4 h post-dose. At each sampling time point, samples from the rats were drawn by sublingual bleeding or by tail cut. After last sampling the rats were sacrificed by $O_2/CO_2$ anaesthesia. The dosing vehicle was 10 mM phosphate, 0.8% NaCl, 0.05% Polysorbate 20 (pH 6.0).

Plasma samples were analyzed after solid phase extraction (SPE) by liquid chromatography mass spectrometry (LC-MS/MS). Mean plasma concentrations were used for calculation of the pharmacokinetic parameters using the non-compartmental approach in Phoenix WinNonlin 6.4 or a later version. Plasma terminal elimination half-life (T½) was determined as $\ln(2)/\lambda z$ where $\lambda z$ is the magnitude of the slope of the log linear regression of the log concentration versus time profile during the terminal phase. $AUC_{inf}$ is the area under the plasma concentration—time curve extrapolated to infinity ($AUC_{inf}=AUC_{last}+C_{last}/\lambda z$, where $C_{last}$ is the last observed plasma concentration). Cmax is the maximum observed concentration, occurring at Tmax. Results for selected compounds are shown in table 6.

TABLE 6

| Cpd. No. | Dose nmol/kg | AUC$_{INF}$ (hr*nmol/L) | Cmax (nmol/L) | T$_{1/2}$ (hr) |
|---|---|---|---|---|
| 3 | 70 | 83.9 | 36.9 | 0.99 |
| 8 | 70 | 98.3 | 76.9 | 0.62 |
| 30 | 70 | 46.7 | 33.3 | 0.74 |
| 52 | 70 | 48.5 | 31.2 | 0.89 |
| 53 | 70 | 31.1 | 50.0 | 0.87 |
| 95 | 70 | 85.0 | 46.5 | 1.09 |
| 97 | 70 | 112.0 | 52.6 | 1.04 |
| 101 | 70 | 131.8 | 58.6 | 0.91 |
| 103 | 70 | 176.6 | 68.4 | 1.36 |
| 5 | 70 | 72.4 | 48.4 | 0.93 |

Example 7: Effect of Kv1.3 Blocker Treatment in the Keyhole Limpet Hemocyanin (KLH) Ear Inflammation Model in Rats A classical delayed-type hypersensitivity (DTH) reaction was elicited in one ear of rats. Briefly, male Lewis rats aged 8-10 weeks were immunized on day −7 with 200 µL keyhole limpet hemocyanin (KLH) (from Sigma, cat. no. H7017) (4 mg/mL) emulsified in complete Freund's adjuvant (CFA) (Difco, cat. no. 263810) subcutaneously (SC) at the base of the tail. On day 0 the rats were challenged intradermally with 40 µL KLH/NaCl 0.9% (2 mg/mL) in the left ear. After the ear challenge the rats develop a T-cell dependent inflammation in the left KLH challenged ear. The right ear remains uninflamed and serves as control.

The ability of Kv1.3 blocker treatment to reduce the DTH ear swelling response was investigated by comparing the response in rats (n=8-10/gr) treated with vehicle to that of rats treated with a Kv1.3 blocker. Vehicle or Kv1.3 blocker dissolved in vehicle was administered SC (2 mL/kg) 24 hrs prior to KLH ear challenge. The test dose of Kv1.3 blocker was 50, 70 or 100 nmol/kg. Test vehicle was 10 mM phosphate, 0.8% w/v NaCl, 0.05% w/v polysorbate20, pH 6.

Cyclosporine (CsA) was included as positive study control in all experiments. Cyclosporine (Sandimmune Neooral® 100 mg/mL oral solution, Novartis) was administered per os (10 mg/kg) one hour prior to KLH ear challenge and again 6 hours after KLH ear challenge.

As primary read-out of efficacy, the Area Under Curve (AUC) of Δ ear thickness (mm) was calculated for each animal from 0-48 hours post induction of the ear DTH reaction, where the change (D) was calculated as: Left ear thickness-right ear thickness. These results were then used to calculate % inhibition of ear thickness by Kv1.3 blocker treatment: % inhibition: ((1−(individual Δ AUC Kv1.3 blocker/average ΔAUC vehicle group))×100. Results were calculated as % inhibition+/−standard deviation (SD), and are shown in Table 7 and Table 8.

TABLE 7

| Exp | Dose (nmol/kg) | Cpd. 3 | Cpd. 41 | Cpd. 52 | CsA* |
|---|---|---|---|---|---|
| #1 | 70 | 38.8 (+/−9.7) | 46.9 (+/−10.9) | | 71.4(+/−4.8) |
| #2 | 70 | 25.0 (+/−12.5) | 27.7 (+/−11.5) | | 76.8(+/−13.4) |
| #3 | 50 | 37.3 (+/−13.8) | 22.2 (+/−11.1) | | 65.1(+/−4.5) |

TABLE 7-continued

| Exp | Dose (nmol/kg) | Cpd. 3 | Cpd. 41 | Cpd. 52 | CsA* |
|---|---|---|---|---|---|
| #4 | 100 | | 41.9 (+/−12.5) | 25.1 (+/−6.3) | 63.4 (+/−5.9) |

TABLE 8

| Exp. | Dose (nmol/kg) | Cpd.95 | Cpd. 97 | Cpd. 101 | Cpd.103 | CsA |
|---|---|---|---|---|---|---|
| #5 | 100 | 39.6 (+/−8.3) | | | | 67.1 (+/−7.9) |
| #6 | 100 | | 42.5 (+/−14.0) | 44.5 (+/−5.2) | | 55.3 (+/−5.5) |
| #7 | 100 | | | | 48.9 (+/−8.6) | 67.9 (+/−5.4) |
| #8 | 100 | 37.7 (+/−10.0) | | | | 57.8 (+/−2.8) |

The work described in this specification has received funding from the European Communities Seventh Framework Program FP7/2007-2013 under grant agreement Venomics_CA_20111021.

The invention claimed is:

1. An ion channel blocker or pharmaceutically acceptable salt comprising a Kv1.3 inhibitor component, wherein the Kv1.3 inhibitor component comprises one of the sequences:

QMDMRCSASVECKQKCLKAIGSIFGKCMNKKCKCYPR, (SEQ ID NO. 1)

QMDMRCSASVECKQKCLKAIGRGFGKCMNKKCKCYPR, (SEQ ID NO. 2)

NMDMRCSASVECKQKCLKAIGSIFGKCMNKKCKCYPR, (SEQ ID NO. 3)

NMDMRCSASVECKQKCLKAIGRGFGKCMNKKCKCYPR, (SEQ ID NO. 4)

MDMRCSASVECKQKCLKAIGSIFGKCMNKKCKCYPR, (SEQ ID NO. 5)

DMRCSASVECKQKCLKAIGSIFGKCMNKKCKCYPR, (SEQ ID NO. 6)

NMDMRCSASVECKQKCLKAIGSIFGKCMNKKCKCYPR, (SEQ ID NO. 7)

NIDMRCSASVECKQKCLKAIGSIFGKCMNKKCKCYPR, (SEQ ID NO. 8)

```
                                                     (SEQ ID NO. 9)
NMDVRCSASVECKQKCLKAIGSIFGKCMNKKCKCYPR, (SEQ ID NO. 10)
NMDMRCSASVECKQKCKDAIGSIFGKCMNKKCKCYPR, (SEQ ID NO. 11)
GGNMDMRCSASVECKQKCLKAIGSIFGKCMNKKCKCYPR, (SEQ ID NO. 12)
NMEMRCSASVECKQKCLKAIGSIFGKCMNKKCKCYPR, (SEQ ID NO. 13)
SGNMDMRCSASVECKQKCLKAIGSIFGKCMNKKCKCYPR, (SEQ ID NO. 14)
N[Nle]DMRCSASVECKQKCLKAIGSIFGKCMNKKCKCYPR, (SEQ ID NO. 15)
NMD[Nle]RCSASVECKQKCLKAIGSIFGKCMNKKCKCYPR, (SEQ ID NO. 16)
NMDMRCSASVECKQKCLKAIGSIFGKC[Nle]NKKCKCYPR, (SEQ ID NO. 17)
NMDMRCSASVECKVKCLKAIGSIFGKCMNKKCKCYPR, (SEQ ID NO. 18)
NMDMRCSASVECKQLCLKAIGSIFGKCMNKKCKCYPR, (SEQ ID NO. 19)
NMDMRCSASVECKQKCKKAIGSIFGKCMNKKCKCYPR, (SEQ ID NO. 20)
NMDMRCSASVECKQKCLDAIGSIFGKCMNKKCKCYPR, (SEQ ID NO. 21)
NMDMRCSASVECKQKCLKAIRSIFGKCMNKKCKCYPR, (SEQ ID NO. 22)
NMDMRCSASVECKQKCLKAIESIFGKCMNKKCKCYPR, (SEQ ID NO. 23)
NMDMRCSASVECKQKCLKAIGSIFGKCMNKKCKCYPRRRTA, (SEQ ID NO. 24)
NMDMRCSASVECKQKCLKAIGSIFGKCMNKKCKCYPRHRRK, (SEQ ID NO. 25)
NMDMRCKASVECKQKCLKAIGSIFGKCMNKKCKCYPR, (SEQ ID NO. 26)
NMDMRCSISVECKQKCLKAIGSIFGKCMNKKCKCYPR, (SEQ ID NO. 27)
NMDMRCSASRECKQKCLKAIGSIFGKCMNKKCKCYPR, (SEQ ID NO. 28)
NMDMRCSASVQCKQKCLKAIGSIFGKCMNKKCKCYPR, (SEQ ID NO. 29)
NMDMRCSASVECLQKCLKAIGSIFGKCMNKKCKCYPR, (SEQ ID NO. 30)
NMDMRCSASVECAQKCLKAIGSIFGKCMNKKCKCYPR, (SEQ ID NO. 31)
NMDMRCSASVECKEKCLKAIGSIFGKCMNKKCKCYPR, (SEQ ID NO. 32)
NMDMRCSASVECKLKCLKAIGSIFGKCMNKKCKCYPR, (SEQ ID NO. 33)
NMDMRCSASVECKQKCLKAIHSIFGKCMNKKCKCYPR, (SEQ ID NO. 34)
NMDMRCSASVECKQKCLKAIGSKFGKCMNKKCKCYPR, (SEQ ID NO. 35)
NMDMRCSASVECKQKCLKAIGSRFGKCMNKKCKCYPR, (SEQ ID NO. 36)
NMDMRCSASVECKQKCLKAIGSIFGKCMNGKCKCYPR, (SEQ ID NO. 37)
NMDMRCSASVECKQKCLKAIGSIFGKCMNKKCHCYPR, (SEQ ID NO. 38)
NMDMRCSASVECKQKCLKAIGSIFGKCMNKKCVCYPR, (SEQ ID NO. 39)
N[Nle]D[Nle]RCSASVECKQKCLKAIGSIFGKCMNKKCKCYPR, (SEQ ID NO. 40)
N[Nle]D[Nle]RCSASVECKQKCLKAIGSIFGKC[Nle]NKKCKCYPR, (SEQ ID NO. 41)
P[Nle]D[Nle]RCSASVECKQKCLKAIGSIFGKC[Nle]NKKCKCYPR, (SEQ ID NO. 42)
N[Nle]D[Nle]RCRASVECKQKCLKAIGSIFGKC[Nle]NKKCKCYPR, (SEQ ID NO. 43)
N[Nle]D[Nle]RCSASVECEQKCLKAIGSIFGKC[Nle]NKKCKCYPR, (SEQ ID NO. 44)
N[Nle]D[Nle]RCSASVECQQKCLKAIGSIFGKC[Nle]NKKCKCYPR, (SEQ ID NO. 45)
N[Nle]D[Nle]RCSASVECKKKCLKAIGSIFGKC[Nle]NKKCKCYPR, (SEQ ID NO. 46)
N[Nle]S[Nle]RCSASVECKQKCLKAIGSIFGKC[Nle]NKKCKCYPR, (SEQ ID NO. 47)
N[Nle]D[Nle]RCSHSVECKQKCLKAIGSIFGKC[Nle]NKKCKCYPR, (SEQ ID NO. 48)
N[Nle]D[Nle]RCSASVECKQSCLKAIGSIFGKC[Nle]NKKCKCYPR, (SEQ ID NO. 49)
N[Nle]D[Nle]RCSASVECKQKCKAIGSIFGKC[Nle]NKKCKCYPR, (SEQ ID NO. 50)
NMDMRCSASVECKQKCYKAIGSIFGKCMNKKCKCYPR, (SEQ ID NO. 51)
NMDMRCSASVECKQKCRKAIGSIFGKCMNKKCKCYPR, (SEQ ID NO. 52)
NMDMRCSASVECKQKCLAAIGSIFGKCMNKKCKCYPR, (SEQ ID NO. 53)
NMDMRCSASVECKQKCLYAIGSIFGKCMNKKCKCYPR, (SEQ ID NO. 54)
NMDMRCSASVECKQKCLAIGSIFGKCMNKKCKCYPR, (SEQ ID NO. 55)
NMDMRCSASVECKQKCLKYIGSIFGKCMNKKCKCYPR, (SEQ ID NO. 56)
NMDMRCSASVECKQKCLKRIGSIFGKCMNKKCKCYPR, (SEQ ID NO. 57)
NMDMRCSASVECKQKCLKIGSIFGKCMNKKCKCYPR, (SEQ ID NO. 58)
NMDMRCSASVECKQKCLKAYGSIFGKCMNKKCKCYPR, (SEQ ID NO. 59)
NMDMRCSASVECKQKCLKAEGSIFGKCMNKKCKCYPR, (SEQ ID NO. 60)
NMDMRCSASVECKQKCLKARGSIFGKCMNKKCKCYPR, (SEQ ID NO. 61)
NMDMRCSASVECKQKCLKAGSIFGKCMNKKCKCYPR, (SEQ ID NO. 62)
N[Nle]D[Nle]RCSASVECKQKCLKAIGSPFGKC[Nle]NKKCKCYPR,
```

```
                                                    (SEQ ID NO. 63)
N[Nle]D[Nle]RCSASKECKQKCLKAIGSIFGKC[Nle]NKKCKCYPR, (SEQ ID NO. 64)
H[Nle]D[Nle]RCSASVECKQKCLKAIGSIFGKC[Nle]NKKCKCYPR, (SEQ ID NO. 65)
Y[Nle]D[Nle]RCSASVECKQKCLKAIGSIFGKC[Nle]NKKCKCYPR, (SEQ ID NO. 66)
S[Nle]D[Nle]RCSASVECKQKCLKAIGSIFGKC[Nle]NKKCKCYPR, (SEQ ID NO. 67)
s[Nle]D[Nle]RCSASVECKQKCLKAIGSIFGKC[Nle]NKKCKCYPR, (SEQ ID NO. 68)
S[Nle]D[Nle]RCSA[Abu]VECKQKCLKAIGSIFGKCMNKKCKCYPR, (SEQ ID NO. 69)
S[Nle]D[Nle]RCSASVECKQKCLKAIGSIFG[homo-
Lys]CMNKKCKCYPR, (SEQ ID NO. 70)
S[Nle]D[Nle]RCSASVECKQKCLKAIGSIFGKCMNKKCKC[F(4-
NH2)]PR, (SEQ ID NO. 71)
S[Nle]D[Nle]RCSASVECGQKCLKAIGSIFGKCMNKKCKCYPR, (SEQ ID NO. 72)
S[Nle]D[Nle]RCSASVECVQKCLKAIGSIFGKCMNKKCKCYPR, (SEQ ID NO. 73)
S[Nle]D[Nle]RCSASVECK[2-Amino-5-
carboxypentanol]KCLKAIGSIFGKCMNKKCKCYPR, (SEQ ID NO. 74)
S[Nle]D[Nle]RCSASVECKQKCLKAIGSIFGKCMNKKCKCYQ, (SEQ ID NO. 75)
S[Nle]D[Nle]RCSASVECKQKCLKAIGSIFGKCMNKKCRCYPR, (SEQ ID NO. 76)
S[Nle]DERCSASVECKQKCLKAIGSIFGKCMNKKCKCYPR, (SEQ ID NO. 77)
S[Nle]D[Nle]RCSASVECKQKCLGAIGSIFGKCMNKKCKCYPR, (SEQ ID NO. 78)
S[Nle]D[Nle]RCSASVECKQKCLVAIGSIFGKCMNKKCKCYPR, (SEQ ID NO. 79)
S[Nle]D[Nle]RCSASVECAQSCLKAIGSIFGKCMNKKCKCYPR, (SEQ ID NO. 80)
S[Nle]D[Nle]RCSASVECAQKCLAAIGSIFGKCMNKKCKCYPR, (SEQ ID NO. 81)
S[Nle]D[Nle]RCSASVECAQLCLAAIGSIFGKCMNKKCKCYPR, (SEQ ID NO. 82)
S[Nle]D[Nle]RCSASVECKQKCLKAIGSIFGKC[Nle]NKKCKCYPR, (SEQ ID NO. 83)
P[Nle]D[Nle]RCSASVECKQKCLKAIGCIFGKC[Nle]NKKCKCYPC, (SEQ ID NO. 84)
S[Nle]D[Nle]RCSASVECKEKCLQAIGSIFGKC[Nle]NKKCKCYPR, (SEQ ID NO. 85)
P[Nle]D[Nle]RCSASVECKEKCL[homo-
Gln]AIGSIFGKC[Nle]NKKCKCYPR, (SEQ ID NO. 86)
CSASVECKQKCLKAIGCIFGKC[Nle]NKKCKCYPC, (SEQ ID NO. 87)
S[Nle]D[Nle]RCSASVECKQKCLAAIGCIFGKC[Nle]NKKCKCYPC, (SEQ ID NO. 88)
P[Nle]D[Nle]RCSASVECKQKCLKAIGCIFGKC[Nle]NKKCKCYPC, (SEQ ID NO. 89)
S[Nle]D[Nle]RCSALVECKQKCLKAIGSIFGKCMNKKCKCYPR, (SEQ ID NO. 90)
S[Nle]D[Nle]RCSAVVECKQKCLKAIGSIFGKCMNKKCKCYPR, (SEQ ID NO. 91)
S[Nle]D[Nle]RCSASVECKQKCLKAIGSIFGKCMNKKCKC[F(4-
F)]PR, (SEQ ID NO. 92)
S[Nle]D[Nle]RCSASVECKQKCLKAIGSIFGKCMNKKCKC[F(4-
NO2)]PR, (SEQ ID NO. 93)
S[Nle]D[Nle]RCSASVECKQKCLKAIGSIFGKCMNKKCKC[F(4-
CH3)]PR, (SEQ ID NO. 94)
[Nle]D[Nle]RCSASVECKQKCLKAIGSIFGKC[Nle]NKKCKCYPR, (SEQ ID NO. 95)
NID[Nle]RCSASVECKQKCLKAIGSIFGKC[Nle]NKKCKCYPR, (SEQ ID NO. 96)
PIE[Nle]RCSASVECKQKCLKAIGSIFGKC[Nle]NKKCKCYPR, (SEQ ID NO. 97)
P[Nle]E[Nle]RCSASVECKQKCLAAIGSIFGKC[Nle]NKKCKCYPR, (SEQ ID NO. 98)
P[Nle]E[Nle]RCSASVECKQKCLAAIGSIFGKC[Nle]NKKCKCYPR, (SEQ ID NO. 99)
P[Nle]E[Nle]RCSASVECKQKCLLAIGSIFGKC[Nle]NKKCKCYPR, (SEQ ID NO. 100)
PIDERCSASVECKQKCLAAIGSIFGKC[Nle]NKKCKCYPR, (SEQ ID NO. 101)
PIE[Nle]RCSASVECKQKCLAAIGSIFGKC[Nle]NKKCKCYPR, (SEQ ID NO. 102)
P[Nle]D[Nle]RCSASVECAQKCLAAIGSIFGKCMNKKCKCYPR, (SEQ ID NO. 103)
P[Nle]E[Nle]RCSASVECAQKCLAAIGSIFGKC[Nle]NKKCKCYPR, (SEQ ID NO. 104)
CSASVECKQKCLKAIGSIFGKC[Nle]NKKCKCYPR, (SEQ ID NO. 105)
CSASVECKQKCLKAIGSIFGKC[Nle]NKKCKCYPR, (SEQ ID NO. 106)
RCSASVECKQKCLKAIGSIFGKC[Nle]NKKCKCYPR, (SEQ ID NO. 107)
SKCSASVECKQKCLKAIGSIFGKC[Nle]NKKCKCYPR, (SEQ ID NO. 108)
LRCSASVECKQKCLKAIGSIFGKC[Nle]NKKCKCYPR, (SEQ ID NO. 109)
CSASVECKQKCLKAIGSIFGKC[Nle]NKKCKCYPS, (SEQ ID NO. 110)
CSASVECKQKCLKAIGSIFGKC[Nle]NKKCKCYS, (SEQ ID NO. 111)
CSASVECKQKCLKAIGSIFGKC[Nle]NKKCKCYG-NH2,
```

-continued (SEQ ID NO. 112)
CSASVECKQKCLKAIGSIFGKC[Nle]NKKCKCY-NH2, (SEQ ID NO. 113)
RCSASVECKQKCLKAIGSIFGKC[Nle]NKKCKCYPR, (SEQ ID NO. 114)
LRCSASVECKQKCLKAIGSIFGKC[Nle]NKKCKCYPR, (SEQ ID NO. 115)
LRCSASVECKQKCLAAIGSIFGKC[Nle]NKKCKCYPR, (SEQ ID NO. 116)
LRCSASVECKQKCLAAIGSIFGKCMNKKCKCYPR, (SEQ ID NO. 117)
CSASVECKQKCLKAIGSIFGKCMNKKCKCYPR, (SEQ ID NO. 118)
P[Nle]E[Nle]RCSASVECKEKCLAAIGSIFGKC[Nle]NKKCKCYPR, (SEQ ID NO. 119)
p[Nle]E[Nle]RCSASVECKQKCLAAIGSIFGKC[Nle]NKKCKCYPR, (SEQ ID NO. 120)
P[Nle]E[Nle]RCSASVECKQKCLAAIGSIFGKC[Nle]NKKCKCYR, (SEQ ID NO. 121)
P[Nle]E[Nle]RCSASVECKQKCLAAIGSIFGKC[Nle]NKKCKCYPR, (SEQ ID NO. 122)
P[Nle]E[Nle]RCSASVECKQKCLAAIGSIFGKC[Nle]NKKCKCYPRR, (SEQ ID NO. 123)
P[Nle]E[Nle]RCSASVECKQKCLAAIGSIFGKC[Nle]NKKCKCYPRY, (SEQ ID NO. 124)
P[Nle]E[Nle]RCSASVECKQKCLAAIGSIFGKC[Nle]NKKCKCYPRL, (SEQ ID NO. 125)
P[Nle]E[Nle]RCSASVECKQKCLAAIGSIFGKC[Nle]NKKCKCYPRH, (SEQ ID NO. 126)
P[Nle]E[Nle]RCSASVECKQKCLAAIGSIFGKC[Nle]NKKCKCYPRE, (SEQ ID NO. 127)
P[Nle]E[Nle]RCSASVECKQKCLAAIGSIFGKC[NlE]NKKCKCYPRK
S, (SEQ ID NO. 128)
P[Nle]E[Nle]RCSASVECKQKCLAAIGSIFGKC[Nle]NKKCKCYPRFE, (SEQ ID NO. 129)
P[Nle]E[Nle]RCSASVECKQKCLAAIGSIFGKC[Nle]NKKCKCYPRH
R, (SEQ ID NO. 130)
P[Nle]E[Nle]RCSASVECKQKCLAAIGSIFGKC[Nle]NKKCKCYPRA
K, (SEQ ID NO. 131)
P[Nle]E[Nle]RCSASVECKQKCLAAIGSIFGKC[Nle]NKKCKCYP-
[(4-amino-5-hydroxypentyl)guanidine], (SEQ ID NO. 132)
P[Nle]E[Nle]RCSASVECKQKCLAAIGSIFGKC[Nle]NKKCKCYPR-
[4-amino-5-hydroxypentanamide], (SEQ ID NO. 133)
P[Nle]E[Nle]RCSASVECKQKCLAAIGSIFGKC[Nle]NKKCKCYPR
ST, -continued (SEQ ID NO. 134)
P[Nle]E[Nle]RCSASVECKQKCLAAIGSIFGKC[Nle]NKKCKCYPR
RY, (SEQ ID NO. 135)
P[Nle]E[Nle]RCSSSVECKQKCLAAIGSIFGKC[Nle]NKKCKCYPR, (SEQ ID NO. 136)
P[Nle]E[Nle]RCSLSVECKQKCLAAIGSIFGKC[Nle]NKKCKCYPR, (SEQ ID NO. 137)
P[Nle]E[Nle]RCSAPVECKQKCLAAIGSIFGKC[Nle]NKKCKCYPR, (SEQ ID NO. 138)
P[Nle]E[Nle]RCSASPECKQKCLAAIGSIFGKC[Nle]NKKCKCYPR, (SEQ ID NO. 139)
P[Nle]E[Nle]RCSASQECKQKCLAAIGSIFGKC[Nle]NKKCKCYPR, (SEQ ID NO. 140)
P[Nle]E[Nle]RCSASVECLQKCLAAIGSIFGKC[Nle]NKKCKCYPR, (SEQ ID NO. 141)
P[Nle]E[Nle]RCSASVECKQPCLAAIGSIFGKC[Nle]NKKCKCYPR, (SEQ ID NO. 142)
P[Nle]E[Nle]RCEASVECKQKCLAAIGSIFGKC[Nle]NKKCKCYPR, (SEQ ID NO. 143)
P[Nle]E[Nle]RCFASVECKQKCLAAIGSIFGKC[Nle]NKKCKCYPR, (SEQ ID NO. 144)
P[Nle]E[Nle]RCSYSVECKQKCLAAIGSIFGKC[Nle]NKKCKCYPR, or (SEQ ID NO. 145)
P[Nle]E[Nle]RCSAFVECKQKCLAAIGSIFGKC[Nle]NKKCKCYPR.

2. An ion channel blocker or pharmaceutically acceptable salt according to claim 1 consisting of one of the sequences:

(SEQ ID NO. 3)
NMDMRCSASVECKQKCLKAIGSIFGKCMNKKCKCYPR, (SEQ ID NO. 4)
NMDMRCSASVECKQKCLKAIGRGFGKCMNKKCKCYPR, (SEQ ID NO. 5)
MDMRCSASVECKQKCLKAIGSIFGKCMNKKCKCYPR, (SEQ ID NO. 6)
DMRCSASVECKQKCLKAIGSIFGKCMNKKCKCYPR, (SEQ ID NO. 7)
NMDMRCSASVECKQKCLKAIGSIFGKCMNKKCKCYPR, (SEQ ID NO. 8)
NIDMRCSASVECKQKCLKAIGSIFGKCMNKKCKCYPR, (SEQ ID NO. 9)
NMDVRCSASVECKQKCLKAIGSIFGKCMNKKCKCYPR, (SEQ ID NO. 10)
NMDMRCSASVECKQKCKDAIGSIFGKCMNKKCKCYPR, (SEQ ID NO. 12)
NMEMRCSASVECKQKCLKAIGSIFGKCMNKKCKCYPR, (SEQ ID NO. 14)
N[Nle]DMRCSASVECKQKCLKAIGSIFGKCMNKKCKCYPR, (SEQ ID NO. 15)
NMD[Nle]RCSASVECKQKCLKAIGSIFGKCMNKKCKCYPR, (SEQ ID NO. 16)
NMDMRCSASVECKQKCLKAIGSIFGKC[Nle]NKKCKCYPR,

-continued (SEQ ID NO. 17)
NMDMRCSASVECKVKCLKAIGSIFGKCMNKKCKCYPR, (SEQ ID NO. 18)
NMDMRCSASVECKQLCLKAIGSIFGKCMNKKCKCYPR, (SEQ ID NO. 19)
NMDMRCSASVECKQKCKKAIGSIFGKCMNKKCKCYPR, (SEQ ID NO. 20)
NMDMRCSASVECKQKCLDAIGSIFGKCMNKKCKCYPR, (SEQ ID NO. 21)
NMDMRCSASVECKQKCLKAIRSIFGKCMNKKCKCYPR, (SEQ ID NO. 22)
NMDMRCSASVECKQKCLKAIESIFGKCMNKKCKCYPR, (SEQ ID NO. 25)
NMDMRCKASVECKQKCLKAIGSIFGKCMNKKCKCYPR, (SEQ ID NO. 26)
NMDMRCSISVECKQKCLKAIGSIFGKCMNKKCKCYPR, (SEQ ID NO. 27)
NMDMRCSASRECKQKCLKAIGSIFGKCMNKKCKCYPR, (SEQ ID NO. 28)
NMDMRCSASVQCKQKCLKAIGSIFGKCMNKKCKCYPR, (SEQ ID NO. 29)
NMDMRCSASVECLQKCLKAIGSIFGKCMNKKCKCYPR, (SEQ ID NO. 30)
NMDMRCSASVECAQKCLKAIGSIFGKCMNKKCKCYPR, (SEQ ID NO. 31)
NMDMRCSASVECKEKCLKAIGSIFGKCMNKKCKCYPR, (SEQ ID NO. 32)
NMDMRCSASVECKLKCLKAIGSIFGKCMNKKCKCYPR, (SEQ ID NO. 33)
NMDMRCSASVECKQKCLKAIHSIFGKCMNKKCKCYPR, (SEQ ID NO. 34)
NMDMRCSASVECKQKCLKAIGSKFGKCMNKKCKCYPR, (SEQ ID NO. 35)
NMDMRCSASVECKQKCLKAIGSRFGKCMNKKCKCYPR, (SEQ ID NO. 36)
NMDMRCSASVECKQKCLKAIGSIFGKCMNGKCKCYPR, (SEQ ID NO. 37)
NMDMRCSASVECKQKCLKAIGSIFGKCMNKKCHCYPR, (SEQ ID NO. 38)
NMDMRCSASVECKQKCLKAIGSIFGKCMNKKCVCYPR, (SEQ ID NO. 39)
N[Nle]D[Nle]RCSASVECKQKCLKAIGSIFGKCMNKKCKCYPR, (SEQ ID NO. 40)
N[Nle]D[Nle]RCSASVECKQKCLKAIGSIFGKC[Nle]NKKCKCYPR, (SEQ ID NO. 41)
P[Nle]D[Nle]RCSASVECKQKCLKAIGSIFGKC[Nle]NKKCKCYPR, (SEQ ID NO. 42)
N[Nle]D[Nle]RCRASVECKQKCLKAIGSIFGKC[Nle]NKKCKCYPR (SEQ ID NO. 43)
N[Nle]D[Nle]RCSASVECEQKCLKAIGSIFGKC[Nle]NKKCKCYPR, (SEQ ID NO. 44)
N[Nle]D[Nle]RCSASVECQQKCLKAIGSIFGKC[Nle]NKKCKCYPR, (SEQ ID NO. 45)
N[Nle]D[Nle]RCSASVECKKKCLKAIGSIFGKC[Nle]NKKCKCYPR (SEQ ID NO. 46)
N[Nle]S[Nle]RCSASVECKQKCLKAIGSIFGKC[Nle]NKKCKCYPR, (SEQ ID NO. 47)
N[Nle]D[Nle]RCSHSVECKQKCLKAIGSIFGKC[Nle]NKKCKCYPR, (SEQ ID NO. 48)
N[Nle]D[Nle]RCSASVECKQSCLKAIGSIFGKC[Nle]NKKCKCYPR, (SEQ ID NO. 49)
N[Nle]D[Nle]RCSASVECKQKCKAIGSIFGKC[Nle]NKKCKCYPR, (SEQ ID NO. 50)
NMDMRCSASVECKQKCYKAIGSIFGKCMNKKCKCYPR, (SEQ ID NO. 51)
NMDMRCSASVECKQKCRKAIGSIFGKCMNKKCKCYPR, (SEQ ID NO. 52)
NMDMRCSASVECKQKCLAAIGSIFGKCMNKKCKCYPR, (SEQ ID NO. 53)
NMDMRCSASVECKQKCLYAIGSIFGKCMNKKCKCYPR, (SEQ ID NO. 54)
NMDMRCSASVECKQKCLAIGSIFGKCMNKKCKCYPR, (SEQ ID NO. 55)
NMDMRCSASVECKQKCLKYIGSIFGKCMNKKCKCYPR, (SEQ ID NO. 56)
NMDMRCSASVECKQKCLKRIGSIFGKCMNKKCKCYPR, (SEQ ID NO. 57)
NMDMRCSASVECKQKCLKIGSIFGKCMNKKCKCYPR, (SEQ ID NO. 58)
NMDMRCSASVECKQKCLKAYGSIFGKCMNKKCKCYPR, (SEQ ID NO. 59)
NMDMRCSASVECKQKCLKAEGSIFGKCMNKKCKCYPR, (SEQ ID NO. 60)
NMDMRCSASVECKQKCLKARGSIFGKCMNKKCKCYPR, (SEQ ID NO. 61)
NMDMRCSASVECKQKCLKAGSIFGKCMNKKCKCYPR, (SEQ ID NO. 62)
N[Nle]D[Nle]RCSASVECKQKCLKAIGSPFGKC[Nle]NKKCKCYPR, (SEQ ID NO. 63)
N[Nle]D[Nle]RCSASKECKQKCLKAIGSIFGKC[Nle]NKKCKCYPR, (SEQ ID NO. 64)
H[Nle]D[Nle]RCSASVECKQKCLKAIGSIFGKC[Nle]NKKCKCYPR, (SEQ ID NO. 65)
Y[Nle]D[Nle]RCSASVECKQKCLKAIGSIFGKC[Nle]NKKCKCYPR, (SEQ ID NO. 66)
S[Nle]D[Nle]RCSASVECKQKCLKAIGSIFGKC[Nle]NKKCKCYPR, (SEQ ID NO. 67)
V[Nle]D[Nle]RCSASVECKQKCLKAIGSIFGKC[Nle]NKKCKCYPR, (SEQ ID NO. 68)
S[Nle]D[Nle]RCSA[Abu]VECKQKCLKAIGSIFGKCMNKKCKCYPR, (SEQ ID NO. 69)
S[Nle]D[Nle]RCSASVECKQKCLKAIGSIFG[homo-Lys]CMNKKCKCYPR, (SEQ ID NO. 70)
S[Nle]D[Nle]RCSASVECKQKCLKAIGSIFGKCMNKKCKC[F(4-NH$_2$)]PR, (SEQ ID NO. 71)
S[Nle]D[Nle]RCSASVECGQKCLKAIGSIFGKCMNKKCKCYPR, (SEQ ID NO. 72)
S[Nle]D[Nle]RCSASVECVQKCLKAIGSIFGKCMNKKCKCYPR, (SEQ ID NO. 73)
S[Nle]D[Nle]RCSASVECK[2-Amino-5-carboxypentanoyl]KCLKAIGSIFGKCMNKKCKCYPR, (SEQ ID NO. 74)
S[Nle]D[Nle]RCSASVECKQKCLKAIGSIFGKCMNKKCKCYQ, (SEQ ID NO. 75)
S[Nle]D[Nle]RCSASVECKQKCLKAIGSIFGKCMNKKCRCYPR, (SEQ ID NO. 76)
S[Nle]DERCSASVECKQKCLKAIGSIFGKCMNKKCKCYPR, (SEQ ID NO. 77)
S[Nle]D[Nle]RCSASVECKQKCLGAIGSIFGKCMNKKCKCYPR, (SEQ ID NO. 78)
S[Nle]D[Nle]RCSASVECKQKCLVAIGSIFGKCMNKKCKCYPR, (SEQ ID NO. 79)
S[Nle]D[Nle]RCSASVECAQSCLKAIGSIFGKCMNKKCKCYPR, (SEQ ID NO. 80)
S[Nle]D[Nle]RCSASVECAQKCLAAIGSIFGKCMNKKCKCYPR, (SEQ ID NO. 81)
S[Nle]D[Nle]RCSASVECAQLCLAAIGSIFGKCMNKKCKCYPR, (SEQ ID NO. 82)
S[Nle]D[Nle]RCSASVECKQKCLKAIGSIFGKC[Nle]NKKCKCYPR, (SEQ ID NO. 83)
P[Nle]D[Nle]RCSASVECKQKCLKAIGCIFGKC[Nle]NKKCKCYPC, (SEQ ID NO. 84)
S[Nle]D[Nle]RCSASVECKEKCLQAIGSIFGKC[Nle]NKKCKCYPR, (SEQ ID NO. 85)
P[Nle]D[Nle]RCSASVECKEKCL[homo-Gln]AlGSIFGKC[Nle]NKKCKCYPR, (SEQ ID NO. 86)
CSASVECKQKCLKAIGCIFGKC[Nle]NKKCKCYPC, (SEQ ID NO. 87)
S[Nle]D[Nle]RCSASVECKQKCLAAIGCIFGKC[Nle]NKKCKCYPC, (SEQ ID NO. 88)
P[Nle]D[Nle]RCSASVECKQKCLKAIGCIFGKC[Nle]NKKCKCYPC, (SEQ ID NO. 89)
S[Nle]D[Nle]RCSALVECKQKCLKAIGSIFGKCMNKKCKCYPR, (SEQ ID NO. 90)
S[Nle]D[Nle]RCSAVVECKQKCLKAIGSIFGKCMNKKCKC(3)YPR, (SEQ ID NO. 91)
S[Nle]D[Nle]RCSASVECKQKCLKAIGSIFGKCMNKKCKC[F(4-F)]PR, (SEQ ID NO. 92)
S[Nle]D[Nle]RCSASVECKQKCLKAIGSIFGKCMNKKCKC[F(4-NO$_2$)]PR, (SEQ ID NO. 93)
S[Nle]D[Nle]RCSASVECKQKCLKAIGSIFGKCMNKKCKC[F(4-CH$_3$)]PR, (SEQ ID NO. 94)
[Nle]D[Nle]RCSASVECKQKCLKAIGSIFGKC[Nle]NKKCKCYPR, (SEQ ID NO. 95)
NID[Nle]RCSASVECKQKCLKAIGSIFGKC[Nle]NKKCKCYPR, (SEQ ID NO. 96)
PIE[Nle]RCSASVECKQKCLKAIGSIFGKC[Nle]NKKCKCYPR, (SEQ ID NO. 97)
P[Nle]E[Nle]RCSASVECKQKCLAAIGSIFGKC[Nle]NKKCKCYPR, (SEQ ID NO. 98)
P[Nle]E[Nle]RCSASVECKQKCLAAIGSIFGKC[Nle]NKKCKCYPR, (SEQ ID NO. 99)
P[Nle]E[Nle]RCSASVECKQKCLLAIGSIFGKC[Nle]NKKCKCYPR, (SEQ ID NO. 100)
PIDERCSASVECKQKCLAAIGSIFGKC[Nle]NKKCKCYPR, (SEQ ID NO. 101)
PIE[Nle]RCSASVECKQKCLAAIGSIFGKC[Nle]NKKCKCYPR, (SEQ ID NO. 102)
P[Nle]D[Nle]RCSASVECAQKCLAAIGSIFGKCMNKKCKCYPR, (SEQ ID NO. 103)
P[Nle]E[Nle]RCSASVECAQKCLAAIGSIFGKC[Nle]NKKCKCYPR, (SEQ ID NO. 104)
CSASVECKQKCLKAIGSIFGKC[Nle]NKKCKCYPR, (SEQ ID NO. 105)
CSASVECKQKCLKAIGSIFGKC[Nle]NKKCKCYPR, (SEQ ID NO. 106)
RCSASVECKQKCLKAIGSIFGKC[Nle]NKKCKCYPR, (SEQ ID NO. 107)
SKCSASVECKQKCLKAIGSIFGKC[Nle]NKKCKCYPR, (SEQ ID NO. 108)
LRCSASVECKQKCLKAIGSIFGKC[Nle]NKKCKCYPR, (SEQ ID NO. 109)
CSASVECKQKCLKAIGSIFGKC[Nle]NKKCKCYPS, (SEQ ID NO. 110)
CSASVECKQKCLKAIGSIFGKC[Nle]NKKCKCYS, (SEQ ID NO. 111)
CSASVECKQKCLKAIGSIFGKC[Nle]NKKCKCYG-NH2, (SEQ ID NO. 112)
CSASVECKQKCLKAIGSIFGKC[Nle]NKKCKCY-NH2, (SEQ ID NO. 113)
RCSASVECKQKCLKAIGSIFGKC[Nle]NKKCKCYPR, (SEQ ID NO. 114)
LRCSASVECKQKCLKAIGSIFGKC[Nle]NKKCKCYPR, (SEQ ID NO. 115)
LRCSASVECKQKCLAAIGSIFGKC[Nle]NKKCKCYPR, (SEQ ID NO. 116)
LRCSASVECKQKCLAAIGSIFGKCMNKKCKCYPR, (SEQ ID NO. 117)
CSASVECKQKCLKAIGSIFGKCMNKKCKCYPR, (SEQ ID NO. 118)
P[Nle]E[Nle]RCSASVECKEKCLAAIGSIFGKC[Nle]NKKCKCYPR, (SEQ ID NO. 119)
p[Nle]E[Nle]RCSASVECKQKCLAAIGSIFGKC[Nle]NKKCKCYPR, (SEQ ID NO. 120)
P[Nle]E[Nle]RCSASVECKQKCLAAIGSIFGKC[Nle]NKKCKCYR, -continued

```
                                        (SEQ ID NO. 121)
[Nle]E[Nle]RCSASVECKQKCLAAIGSIFGKC[Nle]NKKCKCYPR, (SEQ ID NO. 122)
P[Nle]E[Nle]RCSASVECKQKCLAAIGSIFGKC[Nle]NKKCKCYPRR, (SEQ ID NO. 123)
P[Nle]E[Nle]RCSASVECKQKCLAAIGSIFGKC[Nle]NKKCKCYPRY, (SEQ ID NO. 124)
P[Nle]E[Nle]RCSASVECKQKCLAAIGSIFGKC[Nle]NKKCKCYPRL, (SEQ ID NO. 125)
P[Nle]E[Nle]RCSASVECKQKCLAAIGSIFGKC[Nle]NKKCKCYPRH, (SEQ ID NO. 126)
P[Nle]E[Nle]RCSASVECKQKCLAAIGSIFGKC[Nle]NKKCKCYPRE, (SEQ ID NO. 127)
P[Nle]E[Nle]RCSASVECKQKCLAAIGSIFGKC[Nle]NKKCKCYPRK
S, (SEQ ID NO. 128)
P[Nle]E[Nle]RCSASVECKQKCLAAIGSIFGKC[Nle]NKKCKCYPRFE, (SEQ ID NO. 129)
P[Nle]E[Nle]RCSASVECKQKCLAAIGSIFGKC[Nle]NKKCKCYPRH
R, (SEQ ID NO. 130)
P[Nle]E[Nle]RCSASVECKQKCLAAIGSIFGKC[Nle]NKKCKCYPRA
K, (SEQ ID NO. 131)
P[Nle]E[Nle]RCSASVECKQKCLAAIGSIFGKC[Nle]NKKCKCYP-
[(4-amino-5-hydroxypentyl)guanidine], (SEQ ID NO. 132)
P[Nle]E[Nle]RCSASVECKQKCLAAIGSIFGKC[Nle]NKKCKCYPR-
[4-amino-5-hydroxypentanamide], (SEQ ID NO. 133)
P[Nle]E[Nle]RCSASVECKQKCLAAIGSIFGKC[Nle]NKKCKCYPRS
T, (SEQ ID NO. 134)
P[Nle]E[Nle]RCSASVECKQKCLAAIGSIFGKC[Nle]NKKCKCYPRR
Y, (SEQ ID NO. 135)
P[Nle]E[Nle]RCSSSVECKQKCLAAIGSIFGKC[Nle]NKKCKCYPR, (SEQ ID NO. 136)
P[Nle]E[Nle]RCSAPVECKQKCLAAIGSIFGKC[Nle]NKKCKCYPR, (SEQ ID NO. 137)
P[Nle]E[Nle]RCSAPVECKQKCLAAIGSIFGKC[Nle]NKKCKCYPR, (SEQ ID NO. 138)
P[Nle]E[Nle]RCSASPECKQKCLAAIGSIFGKC[Nle]NKKCKCYPR, (SEQ ID NO. 139)
P[Nle]E[Nle]RCSASQECKQKCLAAIGSIFGKC[Nle]NKKCKCYPR, (SEQ ID NO. 140)
P[Nle]E[Nle]RCSASVECLQKCLAAIGSIFGKC[Nle]NKKCKCYPR, (SEQ ID NO. 141)
P[Nle]E[Nle]RCSASVECKQPCLAAIGSIFGKC[Nle]NKKCKCYPR, (SEQ ID NO. 142)
P[Nle]E[Nle]RCEASVECKQKCLAAIGSIFGKC[Nle]NKKCKCYPR,
```

-continued

```
                                        (SEQ ID NO. 143)
P[Nle]E[Nle]RCFASVECKQKCLAAIGSIFGKC[Nle]NKKCKCYPR, (SEQ ID NO. 144)
P[Nle]E[Nle]RCSYSVECKQKCLAAIGSIFGKC[Nle]NKKCKCYPR, or (SEQ ID NO. 145)
P[Nle]E[Nle]RCSAFVECKQKCLAAIGSIFGKC[Nle]NKKCKCYPR.
```

3. An ion channel blocker or pharmaceutically acceptable salt according to claim 1 selected from:

```
(Cpd. 3)
                                          (SEQ ID NO. 3)
H-NMDMRCSASVECKQKCLKAIGSIFGKCMNKKCKCYPR-OH (Cpd. 4)
                                          (SEQ ID NO. 4)
H-NMDMRCSASVECKQKCLKAIGRGFGKCMNKKCKCYPR-OH (Cpd. 5)
                                          (SEQ ID NO. 5)
H-MDMRCSASVECKQKCLKAIGSIFGKCMNKKCKCYPR-OH (Cpd. 6)
                                          (SEQ ID NO. 6)
H-DMRCSASVECKQKCLKAIGSIFGKCMNKKCKCYPR-OH (Cpd. 7)
                                          (SEQ ID NO. 7)
H-NMDMRCSASVECKQKCLKAIGSIFGKCMNKKCKCYPR-NH$_2$ (Cpd. 8)
                                          (SEQ ID NO. 8)
H-NIDMRCSASVECKQKCLKAIGSIFGKCMNKKCKCYPR-OH (Cpd. 9)
                                          (SEQ ID NO. 9)
H-NMDVRCSASVECKQKCLKAIGSIFGKCMNKKCKCYPR-OH (Cpd. 10)
                                          (SEQ ID NO. 10)
H-NMDMRCSASVECKQKCKDAIGSIFGKCMNKKCKCYPR-OH (Cpd. 11)
                                          (SEQ ID NO. 11)
H-GGNMDMRCSASVECKQKCLKAIGSIFGKCMNKKCKCYPR-OH (Cpd. 12)
                                          (SEQ ID NO. 12)
H-NMEMRCSASVECKQKCLKAIGSIFGKCMNKKCKCYPR-OH (Cpd. 13)
                                          (SEQ ID NO. 13)
H-SGNMDMRCSASVECKQKCLKAIGSIFGKCMNKKCKCYPR-OH (Cpd. 14)
                                          (SEQ ID NO. 14)
H-N[Nle]DMRCSASVECKQKCLKAIGSIFGKCMNKKCKCYPR-NH$_2$ (Cpd. 15)
                                          (SEQ ID NO. 15)
H-NMD[Nle]RCSASVECKQKCLKAIGSIFGKCMNKKCKCYPR-NH$_2$ (Cpd. 16)
                                          (SEQ ID NO. 16)
H-NMDMRCSASVECKQKCLKAIGSIFGKC[Nle]NKKCKCYPR-NH$_2$ (Cpd. 17)
                                          (SEQ ID NO. 17)
H-NMDMRCSASVECKVKCLKAIGSIFGKCMNKKCKCYPR-NH$_2$ (Cpd. 18)
                                          (SEQ ID NO. 18)
H-NMDMRCSASVECKQLCLKAIGSIFGKCMNKKCKCYPR-NH$_2$
```

-continued (Cpd. 19)
(SEQ ID NO. 19)
H-NMDMRCSASVECKQKCKKAIGSIFGKCMNKKCKCYPR-NH2

(Cpd. 20)
(SEQ ID NO. 20)
H-NMDMRCSASVECKQKCLDAIGSIFGKCMNKKCKCYPR-NH2

(Cpd. 21)
(SEQ ID NO. 21)
H-NMDMRCSASVECKQKCLKAIRSIFGKCMNKKCKCYPR-NH2

(Cpd. 22)
(SEQ ID NO. 22)
H-NMDMRCSASVECKQKCLKAIESIFGKCMNKKCKCYPR-NH2

(Cpd. 23)
(SEQ ID NO. 23)
H-NMDMRCSASVECKQKCLKAIGSIFGKCMNKKCKCYPRRRTA-NH2

(Cpd. 24)
(SEQ ID NO. 24)
H-NMDMRCSASVECKQKCLKAIGSIFGKCMNKKCKCYPRHRRK-NH2

(Cpd. 25)
(SEQ ID NO. 25)
H-NMDMRCKASVECKQKCLKAIGSIFGKCMNKKCKCYPR-NH2

(Cpd. 26)
(SEQ ID NO. 26)
H-NMDMRCSISVECKQKCLKAIGSIFGKCMNKKCKCYPR-NH2

(Cpd. 27)
(SEQ ID NO. 27)
H-NMDMRCSASRECKQKCLKAIGSIFGKCMNKKCKCYPR-NH2

(Cpd. 28)
(SEQ ID NO. 28)
H-NMDMRCSASVQCKQKCLKAIGSIFGKCMNKKCKCYPR-NH2

(Cpd. 29)
(SEQ ID NO. 29)
H-NMDMRCSASVECLQKCLKAIGSIFGKCMNKKCKCYPR-NH2

(Cpd. 30)
(SEQ ID NO. 30)
H-NMDMRCSASVECAQKCLKAIGSIFGKCMNKKCKCYPR-NH2

(Cpd. 31)
(SEQ ID NO. 31)
H-NMDMRCSASVECKEKCLKAIGSIFGKCMNKKCKCYPR-NH2

(Cpd. 32)
(SEQ ID NO. 32)
H-NMDMRCSASVECKLKCLKAIGSIFGKCMNKKCKCYPR-NH2

(Cpd. 33)
(SEQ ID NO. 33)
H-NMDMRCSASVECKQKCLKAIHSIFGKCMNKKCKCYPR-NH2

(Cpd. 34)
(SEQ ID NO. 34)
H-NMDMRCSASVECKQKCLKAIGSKFGKCMNKKCKCYPR-NH2

(Cpd. 35)
(SEQ ID NO. 35)
H-NMDMRCSASVECKQKCLKAIGSRFGKCMNKKCKCYPR-NH2

(Cpd. 36)
(SEQ ID NO. 36)
H-NMDMRCSASVECKQKCLKAIGSIFGKCMNGKCKCYPR-NH2

(Cpd. 37)
(SEQ ID NO. 37)
H-NMDMRCSASVECKQKCLKAIGSIFGKCMNKKCHCYPR-NH2

(Cpd. 38)
(SEQ ID NO. 38)
H-NMDMRCSASVECKQKCLKAIGSIFGKCMNKKCVCYPR-NH2

(Cpd. 39)
(SEQ ID NO. 39)
H-N[Nle]D[Nle]RCSASVECKQKCLKAIGSIFGKCMNKKCKCYPR-NH2

(Cpd. 40)
(SEQ ID NO. 40)
H-N[Nle]D[Nle]RCSASVECKQKCLKAIGSIFGK[Nle]NKKCKCYPR-NH2

(Cpd. 41)
(SEQ ID NO. 41)
H-P[Nle]D[Nle]RCSASVECKQKCLKAIGSIFGKC[Nle]NKKCKCYPR-NH2

(Cpd. 42)
(SEQ ID NO. 42)
H-N[Nle]D[Nle]RCRASVECKQKCLKAIGSIFGKC[Nle]NKKCKCYPR-NH2

(Cpd. 43)
(SEQ ID NO. 43)
H-N[Nle]D[Nle]RCSASVECEQKCLKAIGSIFGKC[Nle]NKKCKCYPR-NH2

(Cpd. 44)
(SEQ ID NO. 44)
H-N[Nle]D[Nle]RCSASVECQQKCLKAIGSIFGKC[Nle]NKKCKCYPR-NH2

(Cpd. 45)
(SEQ ID NO. 45)
H-N[Nle]D[Nle]RCSASVECKKKCLKAIGSIFGKC[Nle]NKKCKCYPR-NH2

(Cpd. 46)
(SEQ ID NO. 46)
H-N[Nle]S[Nle]RCSASVECKQKCLKAIGSIFGKC[Nle]NKKCKCYPR-NH2

(Cpd. 47)
(SEQ ID NO. 47)
H-N[Nle]D[Nle]RCSHSVECKQKCLKAIGSIFGKC[Nle]NKKCKCYPR-NH2

(Cpd. 48)
(SEQ ID NO. 48)
H-N[Nle]D[Nle]RCSASVECKQSCLKAIGSIFGKC[Nle]NKKCKCYPR-NH2

(Cpd. 49)
(SEQ ID NO. 49)
H-N[Nle]D[Nle]RCSASVECKQKCKAIGSIFGKC[Nle]NKKCKCYPR-NH2

(Cpd. 50)
(SEQ ID NO. 50)
H-NMDMRCSASVECKQKCYKAIGSIFGKCMNKKCKCYPR-NH2

(Cpd. 51)
(SEQ ID NO. 51)
H-NMDMRCSASVECKQKCRKAIGSIFGKCMNKKCKCYPR-NH2

(Cpd. 52)
(SEQ ID NO. 52)
H-NMDMRCSASVECKQKCLAAIGSIFGKCMNKKCKCYPR-NH2

(Cpd. 53)
(SEQ ID NO. 53)
H-NMDMRCSASVECKQKCLYAIGSIFGKCMNKKCKCYPR-NH2

-continued (Cpd. 54)
(SEQ ID NO. 54)
H-NMDMRCSASVECKQKCLAIGSIFGKCMNKKCKCYPR-NH$_2$ (Cpd. 55)
(SEQ ID NO. 55)
H-NMDMRCSASVECKQKCLKYIGSIFGKCMNKKCKCYPR-NH$_2$ (Cpd. 56)
(SEQ ID NO. 56)
H-NMDMRCSASVECKQKCLKRIGSIFGKCMNKKCKCYPR-NH$_2$ (Cpd. 57)
(SEQ ID NO. 57)
H-NMDMRCSASVECKQKCLKIGSIFGKCMNKKCKCYPR-NH$_2$ (Cpd. 58)
(SEQ ID NO. 58)
H-NMDMRCSASVECKQKCLKAYGSIFGKCMNKKCKCYPR-NH$_2$ (Cpd. 59)
(SEQ ID NO. 59)
H-NMDMRCSASVECKQKCLKAEGSIFGKCMNKKCKCYPR-NH$_2$ (Cpd. 60)
(SEQ ID NO. 60)
H-NMDMRCSASVECKQKCLKARGSIFGKCMNKKCKCYPR-NH$_2$ (Cpd. 61)
(SEQ ID NO. 61)
H-NMDMRCSASVECKQKCLKAGSIFGKCMNKKCKCYPR-NH$_2$ (Cpd. 62)
(SEQ ID NO. 62)
H-N[Nle]D[Nle]RCSASVECKQKCLKAIGSPFGK[Nle]NKKCKCYPR-NH$_2$ (Cpd. 63)
(SEQ ID NO. 63)
H-N[Nle]D[Nle]RCSASKECKQKCLKAIGSIFGKC[Nle]NKKCKCYPR-NH$_2$ (Cpd. 64)
(SEQ ID NO. 64)
H-H[Nle]D[Nle]RCSASVECKQKCLKAIGSIFGKC[Nle]NKKCKCYPR-NH$_2$ (Cpd. 65)
(SEQ ID NO. 65)
H-Y[Nle]D[Nle]RCSASVECKQKCLKAIGSIFGKC[Nle]NKKCKCYPR-NH$_2$ (Cpd. 66)
(SEQ ID NO. 66)
H-S[Nle]D[Nle]RCSASVECKQKCLKAIGSIFGKC[Nle]NKKCKCYPR-NH$_2$ (Cpd. 67)
(SEQ ID NO. 67)
H-V[Nle]D[Nle]RCSASVECKQKCLKAIGSIFGKC[Nle]NKKCKCYPR-NH$_2$ (Cpd. 68)
(SEQ ID NO. 68)
H-S[Nle]D[Nle]RCSA[Abu]VECKQKCLKAIGSIFGKCMNKKCKCYPR-NH$_2$ (Cpd. 69)
(SEQ ID NO. 69)
H-S[Nle]D[Nle]RCSASVECKQKCLKAIGSIFG[homo-Lys]CMNKKCKCYPR-NH$_2$ (Cpd. 70)
(SEQ ID NO. 70)
H-S[Nle]D[Nle]RCSASVECKQKCLKAIGSIFGKCMNKKCKC[F(4-NH2)]PR-NH$_2$ (Cpd. 71)
(SEQ ID NO. 71)
H-S[Nle]D[Nle]RCSASVECGQKCLKAIGSIFGKCMNKKCKCYPR-NH$_2$ (Cpd. 72)
(SEQ ID NO. 72)
H-S[Nle]D[Nle]RCSASVECVQKCLKAIGSIFGKCMNKKCKCYPR-NH$_2$ (Cpd. 73)
(SEQ ID NO. 73)
H-S[Nle]D[Nle]RCSASVECK[2-Amino-5-carboxypentanoyl]KCLKAIGSIFGKCMNKKCKCYPR-NH$_2$ (Cpd. 74)
(SEQ ID NO. 74)
H-S[Nle]D[Nle]RCSASVECKQKCLKAIGSIFGKCMNKKCKCYQ-NH$_2$ (Cpd. 75)
(SEQ ID NO. 75)
H-S[Nle]D[Nle]RCSASVECKQKCLKAIGSIFGKCMNKKCRCYPR-NH$_2$ (Cpd. 76)
(SEQ ID NO. 76)
H-S[Nle]DERCSASVECKQKCLKAIGSIFGKCMNKKCKCYPR-NH$_2$ (Cpd. 77)
(SEQ ID NO. 77)
H-S[Nle]D[Nle]RCSASVECKQKCLGAIGSIFGKCMNKKCKCYPR-NH$_2$ (Cpd. 78)
(SEQ ID NO. 78)
H-S[Nle]D[Nle]RCSASVECKQKCLVAIGSIFGKCMNKKCKCYPR-NH$_2$ (Cpd. 79)
(SEQ ID NO. 79)
H-S[Nle]D[Nle]RCSASVECAQSCLKAIGSIFGKCMNKKCKCYPR-NH$_2$ (Cpd. 80)
(SEQ ID NO. 80)
H-S[Nle]D[Nle]RCSASVECAQKCLAAIGSIFGKCMNKKCKCYPR-NH$_2$ (Cpd. 81)
(SEQ ID NO. 81)
H-S[Nle]D[Nle]RCSASVECAQLCLAAIGSIFGKCMNKKCKCYPR-NH$_2$ (Cpd. 82)
(SEQ ID NO. 82)
H-S[Nle]D[Nle]RCSASVECKQKCLKAIGSIFGKC[Nle]NKKCKCYPR-OH (Cpd. 83)
(SEQ ID NO. 83)
H-P[Nle]D[Nle]RCSASVECKQKCLKAIGCIFGKC[Nle]NKKCKCYPC-NH$_2$ (Cpd. 84)
(SEQ ID NO. 84)
H-S[Nle]D[Nle]RCSASVECKEKCLQAIGSIFGKC[Nle]NKKCKCYPR-NH2

(Cpd. 85)
(SEQ ID NO. 85)
H-P[Nle]D[Nle]RCSASVECKEKCL[homo-Gln]AIGSIFGKC[Nle]NKKCKCYPR-NH2

(Cpd. 86)
(SEQ ID NO. 86)
H-CSASVECKQKCLKAIGCIFGKC[Nle]NKKCKCYPC-NH2

(Cpd. 87)
(SEQ ID NO. 87)
H-S[Nle]D[Nle]RCSASVECKQKCLAAIGCIFGKC[Nle]NKKCKCYPC-NH2

(Cpd. 88)
(SEQ ID NO. 88)
H-P[Nle]D[Nle]RCSASVECKQKCLKAIGCIFGKC[Nle]NKKCKCYPC-OH (Cpd. 89)
(SEQ ID NO. 89)
H-S[Nle]D[Nle]RCSALVECKQKCLKAIGSIFGKCMNKKCKCYPR-NH2

(Cpd. 90)
(SEQ ID NO. 90)
H-S[Nle]D[Nle]RCSAVVECKQKCLKAIGSIFGKCMNKKCKCYPR-NH2

(Cpd. 91)
(SEQ ID NO. 91)
H-S[Nle]D[Nle]RCSASVECKQKCLKAIGSIFGKCMNKKCKC[F(4-F)]PR-NH2

(Cpd. 92)
(SEQ ID NO. 92)
H-S[Nle]D[Nle]RCSASVECKQKCLKAIGSIFGKCMNKKCKC[F(4-NO2)]PR-NH2

(Cpd. 93)
(SEQ ID NO. 93)
H-S[Nle]D[Nle]RCSASVECKQKCLKAIGSIFGKCMNKKCKC[F(4-CH3)]PR-NH2

(Cpd. 94)
(SEQ ID NO. 94)
H-[Nle][Nle]RCSASVECKQKCLKAIGSIFGKC[Nle]NKKCKCYPR-OH (Cpd. 95)
(SEQ ID NO. 95)
H-NID[Nle]RCSASVECKQKCLKAIGSIFGKC[Nle]NKKCKCYPR-OH (Cpd. 96)
(SEQ ID NO. 96)
H-PIE[Nle]RCSASVECKQKCLKAIGSIFGKC[Nle]NKKCKCYPR-OH (Cpd. 97)
(SEQ ID NO. 97)
H-P[Nle]E[Nle]RCSASVECKQKCLKAIGSIFGKC[Nle]NKKCKCYPR-OH (Cpd. 98)
(SEQ ID NO. 98)
H-P[Nle]E[Nle]RCSASVECKQKCLAAIGSIFGKC[Nle]NKKCKCYPR-NH2

(Cpd. 99)
(SEQ ID NO. 99)
H-P[Nle]E[Nle]RCSASVECKQKCLLAIGSIFGKC[Nle]NKKCKCYPR-OH (Cpd. 100)
(SEQ ID NO. 100)
H-PIDERCSASVECKQKCLAAIGSIFGKC[Nle]NKKCKCYPR-OH (Cpd. 101)
(SEQ ID NO. 101)
H-PIE[Nle]RCSASVECKQKCLAAIGSIFGKC[Nle]NKKCKCYPR-OH (Cpd. 102)
(SEQ ID NO. 102)
H-P[Nle]D[Nle]RCSASVECAQKCLAAIGSIFGKCMNKKCKCYPR-OH (Cpd. 103)
(SEQ ID NO. 103)
H-P[Nle]E[Nle]RCSASVECAQKCLAAIGSIFGKC[Nle]NKKCKCYPR-OH (Cpd. 104)
(SEQ ID NO. 104)
H-CSASVECKQKCLKAIGSIFGKC[Nle]NKKCKCYPR-NH2

(Cpd. 105)
(SEQ ID NO. 105)
Ac-CSASVECKQKCLKAIGSIFGKC[Nle]NKKCKCYPR-NH2

(Cpd. 106)
(SEQ ID NO. 106)
H-RCSASVECKQKCLKAIGSIFGKC[Nle]NKKCKCYPR-NH2

(Cpd. 107)
(SEQ ID NO. 107)
Ac-SKCSASVECKQKCLKAIGSIFGKC[Nle]NKKCKCYPR-NH2

(Cpd. 108)
(SEQ ID NO. 108)
Ac-LRCSASVECKQKCLKAIGSIFGKC[Nle]NKKCKCYPR-NH2

(Cpd. 109)
(SEQ ID NO. 109)
Ac-CSASVECKQKCLKAIGSIFGKC[Nle]NKKCKCYPS-NH2

(Cpd. 110)
(SEQ ID NO. 110)
Ac-CSASVECKQKCLKAIGSIFGKC[Nle]NKKCKCYS-NH2

(Cpd. 111)
(SEQ ID NO. 111)
Ac-CSASVECKQKCLKAIGSIFGKC[Nle]NKKCKCYG-NH2

(Cpd. 112)
(SEQ ID NO. 112)
Ac-CSASVECKQKCLKAIGSIFGKC[Nle]NKKCKCY-NH2

(Cpd. 113)
(SEQ ID NO. 113)
Ac-RCSASVECKQKCLKAIGSIFGKC[Nle]NKKCKCYPR-OH (Cpd. 114)
(SEQ ID NO. 114)
H-LRCSASVECKQKCLKAIGSIFGKC[Nle]NKKCKCYPR-OH (Cpd. 115)
(SEQ ID NO. 115)
Ac-LRCSASVECKQKCLAAIGSIFGKC[Nle]NKKCKCYPR-OH

-continued (Cpd. 116)
(SEQ ID NO. 116)
Ac-LRCSASVECKQKCLAAIGSIFGKCMNKKCKCYPR-OH (Cpd. 117)
(SEQ ID NO. 117)
H-CSASVECKQKCLKAIGSIFGKCMNKKCKCYPR-OH (Cpd. 118)
(SEQ ID NO. 118)
H-P[Nle]E[Nle]RCSASVECKEKCLAAIGSIFGKC[Nle]NKKCKCYP
R-OH (Cpd. 119)
(SEQ ID NO. 119)
H-p[Nle]E[Nle]RCSASVECKQKCLAAIGSIFGKC[Nle]NKKCKCYP
R-OH (Cpd. 120)
(SEQ ID NO. 120)
H-P[Nle]E[Nle]RCSASVECKQKCLAAIGSIFGKC[Nle]NKKCKCY
R-OH (Cpd. 121)
(SEQ ID NO. 121)
H[Nle]E[Nle]RCSASVECKQKCLAAIGSIFGKC[Nle]NKKCKCYPR-OH (Cpd. 122)
(SEQ ID NO. 122)
H-P[Nle]E[Nle]RCSASVECKQKCLAAIGSIFGKC[Nle]NKKCKCYP
RR-OH (Cpd. 123)
(SEQ ID NO. 123)
H-P[Nle]E[Nle]RCSASVECKQKCLAAIGSIFGKC[Nle]NKKCKCYP
RY-OH (Cpd. 124)
(SEQ ID NO. 124)
H-P[Nle]E[Nle]RCSASVECKQKCLAAIGSIFGKC[Nle]NKKCKCYP
RL-OH (Cpd. 125)
(SEQ ID NO. 125)
H-P[Nle]E[Nle]RCSASVECKQKCLAAIGSIFGKC[Nle]NKKCKCYP
RH-OH (Cpd. 126)
(SEQ ID NO. 126)
H-P[Nle]E[Nle]RCSASVECKQKCLAAIGSIFGKC[Nle]NKKCKCYP
RE-OH (Cpd. 127)
(SEQ ID NO. 127)
H-P[Nle]E[Nle]RCSASVECKQKCLAAIGSIFGKC[Nle]NKKCKCYP
RKS-OH (Cpd. 128)
(SEQ ID NO. 128)
H-P[Nle]E[Nle]RCSASVECKQKCLAAIGSIFGKC[Nle]NKKCKCYP
RFE-OH (Cpd. 129)
(SEQ ID NO. 129)
H-P[Nle]E[Nle]RCSASVECKQKCLAAIGSIFGKC[Nle]NKKCKCYP
RHR-OH -continued (Cpd. 130)
(SEQ ID NO. 130)
H-P[Nle]E[Nle]RCSASVECKQKCLAAIGSIFGKC[Nle]NKKCKCYP
RAK-OH (Cpd. 131)
(SEQ ID NO. 131)
H-P[Nle]E[Nle]RCSASVECKQKCLAAIGSIFGKC[Nle]NKKCKCY
P-[(4-amino-5-hydroxypentyl)guanidine]

(Cpd. 132)
(SEQ ID NO. 132)
H-P[Nle]E[Nle]RCSASVECKQKCLAAIGSIFGKC[Nle]NKKCKCYP
R-[4-amino-5-hydroxypentanamide]

(Cpd. 133)
(SEQ ID NO. 133)
H-P[Nle]E[Nle]RCSASVECKQKCLAAIGSIFGKC[Nle]NKKCKCYP
RST-OH (Cpd. 134)
(SEQ ID NO. 134)
H-P[Nle]E[Nle]RCSASVECKQKCLAAIGSIFGKC[Nle]NKKCKCYP
RRY-OH (Cpd. 135)
(SEQ ID NO. 135)
H-P[Nle]E[Nle]RCSSSVECKQKCLAAIGSIFGKC[Nle]NKKCKCYP
R-OH (Cpd. 136)
(SEQ ID NO. 136)
H-P[Nle]E[Nle]RCSLSVECKQKCLAAIGSIFGKC[Nle]NKKCKCYP
R-OH (Cpd. 137)
(SEQ ID NO. 137)
H-P[Nle]E[Nle]RCSAPVECKQKCLAAIGSIFGKC[Nle]NKKCKCYP
R-OH (Cpd. 138)
(SEQ ID NO. 138)
H-P[Nle]E[Nle]RCSASPECKQKCLAAIGSIFGKC[Nle]NKKCKCYP
R-OH (Cpd. 139)
(SEQ ID NO. 139)
H-P[Nle]E[Nle]RCSASQECKQKCLAAIGSIFGKC[Nle]NKKCKCYP
R-OH (Cpd. 140)
(SEQ ID NO. 140)
H-P[Nle]E[Nle]RCSASVECLQKCLAAIGSIFGKC[Nle]NKKCKCYP
R-OH (Cpd. 141)
(SEQ ID NO. 141)
H-P[Nle]E[Nle]RCSASVECKQPCLAAIGSIFGKC[Nle]NKKCKCYP,
R-OH (Cpd. 142)
(SEQ ID NO. 142)
H-P[Nle]E[Nle]RCEASVECKQKCLAAIGSIFGKC[Nle]NKKCKCYP
R-OH,

-continued (Cpd. 143)
(SEQ ID NO. 143)
H-P[Nle]E[Nle]RCFASVECKQKCLAAIGSIFGKC[Nle]NKKCKCYPR-OH, (Cpd. 144)
(SEQ ID NO. 144)
H-P[Nle]E[Nle]RCSYSVECKQKCLAAIGSIFGKC[Nle]NKKCKCYPR-OH or (Cpd. 145)
(SEQ ID NO. 145)
H-P[Nle]E[Nle]RCSAFVECKQKCLAAIGSIFGKC[Nle]NKKCKCYPR-OH.

4. A pharmaceutical composition comprising an ion channel blocker or pharmaceutically acceptable salt according to claim 1, 2 or 3, in admixture with a pharmaceutically acceptable carrier.

5. An ion channel blocker or pharmaceutically acceptable salt according to claim 1 which is a fusion protein comprising the Kv1.3 inhibitor component and one or more heterologous polypeptide sequences.

6. An ion channel blocker or pharmaceutically acceptable salt according to claim 5 wherein the Kv1.3 inhibitor component is inserted within a heterologous scaffold polypeptide.

7. An ion channel blocker or pharmaceutically acceptable salt according to claim 1 wherein the ion channel blocker has a maximum length of 200 amino acids.

8. A method of synthesising an ion channel blocker according to claim 1, 2 or 3, the method comprising:
(a) synthesising the ion channel blocker by means of solid-phase or liquid-phase peptide synthesis methodology and recovering the peptide thus obtained;
(b) expressing the ion channel blocker from a nucleic acid construct that encodes the ion channel blocker and recovering the expression product; or
(c) expressing a precursor peptide from a nucleic acid construct that encodes the precursor peptide sequence, recovering the expression product, and modifying the precursor peptide to yield the ion channel blocker.

9. A method for
(i) treating an autoimmune disorder, allergy, hypersensitivity, allograft rejection, or graft versus host disease;
(ii) treating hay fever, asthma, anaphylaxis, allergic rhinitis, urticaria, eczema, alopecia areata, dermatomyositis, inclusion body myositis, polymyositis, ankylosing spondylitis, vasculitis, rheumatoid arthritis, Sjogren's syndrome, systemic lupus erythematosus (SLE), uveitis, inflammatory fibrosis, chronic obstructive pulmonary disease (COPD), hepatitis, chronic inflammatory demyelinating polyneuropathy, inflammatory bowel disease, colitis, erythema, thyroiditis, psoriasis, atopic dermatitis, allergic contact dermatitis, scleroderma, glomerulonephritis, inflammatory bone resorption, multiple sclerosis or transplant rejection;
(iii) inhibiting weight gain, promoting weight loss, or reducing excess body weight;
(iv) treating obesity or obesity linked inflammation, obesity linked gallbladder disease or obesity induced sleep apnoea;
(v) treating metabolic syndrome, insulin resistance, glucose intolerance, pre-diabetes, increased fasting glucose or type 2 diabetes;
(vi) treating a smooth muscle proliferative disorder;
(vii) treating Alzheimer's disease, multiple sclerosis (MS), Parkinson's disease or amyotrophic lateral sclerosis (ALS) or
(viii) treating cancer
in a subject in need thereof, wherein said method comprising administering the ion channel blocker or pharmaceutically acceptable salt of claim 1, 2 or 3 to said subject.

10. A method according to claim 9 wherein:
the smooth muscle proliferative disorder is restenosis.

11. The method according to claim 9 wherein the inflammatory fibrosis is scleroderma, lung fibrosis or cirrhosis.

12. The method according to claim 9 wherein the colitis is Crohn's disease or ulcerative colitis.

13. The method according to claim 9 wherein the lymphoma is non-Hodgkin lymphoma (NHL).

14. The method according to claim 13 wherein the lymphoma is large B-cell lymphoma, follicular lymphoma, Burkitt lymphoma, immunoblastic large cell lymphoma, precursor B-lymphoblastic lymphoma, mantle cell lymphoma, mycosis fungoides, anaplastic large cell lymphoma, peripheral T-cell lymphoma, precursor T-lymphoblastic lymphoma or Sezary syndrome.

* * * * *

UNITED STATES PATENT AND TRADEMARK OFFICE
CERTIFICATE OF CORRECTION

PATENT NO. : 11,780,893 B2
APPLICATION NO. : 17/679925
DATED : October 10, 2023
INVENTOR(S) : Henrik Fischer Munch et al.

It is certified that error appears in the above-identified patent and that said Letters Patent is hereby corrected as shown below:

In the Specification

At Column 17, Line 44, delete "-NH2".

At Column 17, Line 46, delete "-NH2".

At Column 27, Line 10, delete "-NH2".

At Column 27, Line 12, delete "-NH2".

In the Claims

At Column 187, Lines 59-63, below "sequences:" delete "(SEQ ID NO. 1) QMDMRCSASVECKQKCLKAIGSIFGKCMNKKCKCYPR, (SEQ ID NO. 2) QMDMRCSASVECKQKCLKAIGRGFGKCMNKKCKCYPR,".

At Column 189, Lines 6-7, below "(SEQ ID NO. 10)" delete "(SEQ ID NO. 11) GGNMDMRCSASVECKQKCLKAIGSIFGKCMNKKCKCYPR,".

At Column 189, Lines 11-12, below "(SEQ ID NO. 12)" delete "(SEQ ID NO. 13) SGNMDMRCSASVECKQKCLKAIGSIFGKCMNKKCKCYPR,".

At Column 189, Lines 35-38, below "(SEQ ID NO. 22)" delete "(SEQ ID NO. 23) NMDMRCSASVECKQKCLKAIGSIFGKCMNKKCKCYPRRRTA, (SEQ ID NO. 24) NMDMRCSASVECKQKCLKAIGSIFGKCMNKKCKCYPRHRRK,".

At Column 191, Line 13, "s[Nle]" should be -- V[Nle] --.

Signed and Sealed this
Nineteenth Day of November, 2024

Katherine Kelly Vidal
*Director of the United States Patent and Trademark Office*

CERTIFICATE OF CORRECTION (continued)
U.S. Pat. No. 11,780,893 B2

At Column 191, Line 22, "NH2)" should be -- NH$_2$) --.

At Column 191, Line 32, "carboxypentanol]" should be -- carboxypentanoyl] --.

At Column 192, Line 66, delete "-NH2".

At Column 193, Line 2, delete "-NH2".

At Column 193, Line 40, "[NlE]" should be -- [Nle] --.

At Column 194, Line 57, below "(SEQ ID NO. 10)" insert -- (SEQ ID NO. 11) GGNMDMRCSASVECKQKCLKAIGSIFGKCMNKKCKCYPR, --.

At Column 194, Line 59, below "(SEQ ID NO. 12)" insert -- (SEQ ID NO. 13) SGNMDMRCSASVECKQKCLKAIGSIFGKCMNKKCKCYPR, --.

At Column 195, Line 16, below "(SEQ ID NO. 22)" insert -- (SEQ ID NO. 23) NMDMRCSASVECKQKCLKAIGSIFGKCMNKKCKCYPRRRTA,
(SEQ ID NO. 24)
NMDMRCSASVECKQKCLKAIGSIFGKCMNKKCKCYPRHRRK, --.

At Column 197, Line 40, "AlGSIFGKC" should be -- AIGSIFGKC --.

At Column 197, Line 53, "C (3) Y" should be -- CY --.

At Column 198, Line 44, delete "-NH2".

At Column 198, Line 47, delete "-NH2".

At Column 199, Line 51, "SAPV" should be -- SLSV --.

At Column 204, Line 5, "NH2)" should be -- NH$_2$) --.

At Column 205, Line 44, "NO2)" should be -- NO$_2$) --.

At Column 205, Line 49, "CH3)" should be -- CH$_3$) --.

At Column 205, Line 53, "H-[Nle][Nle]" should be -- H-[Nle]D[Nle] --.

At Column 207, Line 16, "H-p[Nle]" should be -- H-P[Nle] --.

At Column 207, Line 25, "H[Nle]" should be -- H-[Nle] --.

At Column 208, Lines 59-61, "P, R-OH" should be -- PR-OH, --.

At Column 210, Line 1, "for" should be -- for: --.

CERTIFICATE OF CORRECTION (continued)
U.S. Pat. No. 11,780,893 B2

At Column 210, Line 26, "(ALS)" should be -- (ALS); --.

At Column 210, Line 27, "cancer" should be -- cancer; --.

At Column 210, Line 45, "Sezary" should be -- Sézary --.